US010772851B2

(12) United States Patent
Neumann et al.

(10) Patent No.: US 10,772,851 B2
(45) Date of Patent: Sep. 15, 2020

(54) TREATMENT AND PREVENTION OF FUNGAL INFECTIONS

(71) Applicants: Aaron Kurt Neumann, Albuquerque, NM (US); Harry Craig Pappas, Albuquerque, NM (US); Matthew Graus, Albuquerque, NM (US); David G. Whitten, Albuquerque, NM (US); Kirk S. Schanze, Helotes, TX (US); Rina Sylejmani, Albuquerque, NM (US)

(72) Inventors: Aaron Kurt Neumann, Albuquerque, NM (US); Harry Craig Pappas, Albuquerque, NM (US); Matthew Graus, Albuquerque, NM (US); David G. Whitten, Albuquerque, NM (US); Kirk S. Schanze, Helotes, TX (US); Rina Sylejmani, Albuquerque, NM (US)

( * ) Notice: Subject to any disclaimer, the term of this patent is extended or adjusted under 35 U.S.C. 154(b) by 55 days.

(21) Appl. No.: 15/886,469

(22) Filed: Feb. 1, 2018

(65) Prior Publication Data

US 2018/0221309 A1    Aug. 9, 2018

Related U.S. Application Data

(60) Provisional application No. 62/454,355, filed on Feb. 3, 2017.

(51) Int. Cl.
*A61K 31/14*     (2006.01)
*A61K 31/75*     (2006.01)
*A61K 31/795*    (2006.01)
*A61P 31/10*     (2006.01)

(52) U.S. Cl.
CPC .............. *A61K 31/14* (2013.01); *A61K 31/75* (2013.01); *A61K 31/795* (2013.01); *A61P 31/10* (2018.01)

(58) Field of Classification Search
None
See application file for complete search history.

(56) References Cited

U.S. PATENT DOCUMENTS

| | | | |
|---|---|---|---|
| 4,251,386 A | 2/1981 | Saeki et al. | |
| 5,449,809 A | 9/1995 | Wingert et al. | |
| 5,489,400 A | 2/1996 | Liu et al. | |
| 6,743,640 B2 | 6/2004 | Whitten et al. | |
| 6,841,669 B2 | 1/2005 | Cipriani et al. | |
| 7,122,383 B2 | 10/2006 | Jones et al. | |
| 8,455,265 B2 | 6/2013 | Whitten et al. | |
| 8,598,053 B2 | 12/2013 | Whitten et al. | |
| 8,618,009 B2 * | 12/2013 | Schanze | A01N 25/00 252/503 |
| 8,753,570 B2 | 6/2014 | Whitten et al. | |
| 9,005,540 B2 | 4/2015 | Schanze et al. | |
| 9,125,415 B2 | 9/2015 | Schanze et al. | |
| 9,527,806 B2 | 12/2016 | Whitten et al. | |
| 9,549,549 B2 | 1/2017 | Whitten et al. | |
| 9,750,250 B2 | 9/2017 | Whitten et al. | |
| 9,968,698 B2 | 5/2018 | Whitten et al. | |
| 10,058,099 B2 | 8/2018 | Whitten et al. | |
| 10,092,000 B2 | 10/2018 | Whitten et al. | |
| 10,174,042 B2 | 1/2019 | Whitten et al. | |
| 2002/0177828 A1 | 11/2002 | Batich et al. | |
| 2003/0134959 A1 | 7/2003 | Hancock et al. | |
| 2003/0168756 A1 | 9/2003 | Balkus, Jr. et al. | |
| 2003/0178607 A1 | 9/2003 | Swager et al. | |
| 2004/0241768 A1 | 12/2004 | Whitten et al. | |
| 2005/0059168 A1 | 3/2005 | Bazan et al. | |
| 2005/0148254 A1 | 7/2005 | Lu et al. | |
| 2006/0120923 A1 | 6/2006 | Swager et al. | |
| 2006/0175193 A1 | 8/2006 | Inganas et al. | |
| 2007/0065049 A1 | 3/2007 | Alldredge-howard et al. | |
| 2007/0215841 A1 | 9/2007 | Ford et al. | |
| 2008/0090021 A1 | 4/2008 | Long et al. | |
| 2010/0035948 A1 | 2/2010 | Kumar et al. | |
| 2010/0285081 A1 | 11/2010 | Chen et al. | |
| 2011/0076648 A1 | 3/2011 | Lindheim et al. | |
| 2011/0159605 A1 | 6/2011 | Whitten et al. | |
| 2011/0223058 A1 | 9/2011 | Whitten et al. | |
| 2011/0293470 A1 | 12/2011 | Schanze et al. | |
| 2012/0271023 A1 | 10/2012 | Whitten et al. | |
| 2013/0210828 A1 | 8/2013 | Whitten et al. | |
| 2013/0273800 A1 | 10/2013 | Whitten et al. | |
| 2013/0330386 A1 | 12/2013 | Whitten et al. | |
| 2014/0086795 A1 | 3/2014 | Schanze et al. | |
| 2014/0242148 A1 | 8/2014 | Whitten et al. | |
| 2014/0341776 A1 | 11/2014 | Schanze et al. | |
| 2015/0115362 A1 | 4/2015 | Su et al. | |
| 2015/0132184 A1 | 5/2015 | Whitten et al. | |
| 2016/0222150 A1 | 8/2016 | Whitten et al. | |
| 2017/0023554 A1 | 1/2017 | Whitten et al. | |
| 2017/0057970 A1 | 3/2017 | Whitten et al. | |
| 2017/0164614 A1 | 6/2017 | Whitten et al. | |
| 2018/0020663 A1 | 1/2018 | Whitten et al. | |
| 2019/0116797 A1 | 4/2019 | Whitten et al. | |

FOREIGN PATENT DOCUMENTS

| | | |
|---|---|---|
| CA | 2973982 C | 4/2018 |
| JP | 3198365 B2 | 8/2001 |

(Continued)

OTHER PUBLICATIONS

Wang et al. "Antimicrobial activity of cationic conjugated polyelectrolytes and oligomers against *Saccharomyces cerevisiae* vegetative cells and Ascospores", 2013, ACS Applied Materials and Interfaces, pp. 4555-4561 (Year: 2013).*

(Continued)

*Primary Examiner* — Dennis Heyer
(74) *Attorney, Agent, or Firm* — Schwegman Lundberg & Woessner, P.A.

(57) ABSTRACT

Various embodiments disclosed relate to treatment of fungal infections. The present invention provides a method of treating a fungal infection including contacting a fungus including a β-glucan that is at least partially masked from immune system detection with a therapeutically effective amount of a compound that at least partially unmasks the β-glucan to increase immunogenicity of the fungus.

18 Claims, 17 Drawing Sheets

(56) References Cited

FOREIGN PATENT DOCUMENTS

| WO | WO-2005065323 A2 | 7/2005 |
|---|---|---|
| WO | WO-2008143731 A2 | 11/2008 |
| WO | WO-2009158606 A2 | 12/2009 |
| WO | WO-2009158606 A9 | 12/2009 |
| WO | WO-2010044743 A1 | 4/2010 |
| WO | WO-2010054304 A2 | 5/2010 |
| WO | WO-2011044580 A2 | 4/2011 |
| WO | WO-2011044580 A3 | 4/2011 |
| WO | WO-2012009472 A2 | 1/2012 |
| WO | WO-2012009484 A2 | 1/2012 |
| WO | WO-2012079085 A2 | 6/2012 |
| WO | WO-2013020096 A2 | 2/2013 |
| WO | WO-2013020096 A3 | 2/2013 |
| WO | WO-2013055417 A2 | 4/2013 |
| WO | WO-2013055417 A3 | 4/2013 |
| WO | WO-2015138965 A1 | 9/2015 |
| WO | WO-2016115362 A1 | 7/2016 |

OTHER PUBLICATIONS

Pappas et al. "Anti-fungal Properties of Cationic Phenylene Ethynylenes and their impact on β-glucan exposure", 2016, Antimicrobial Agents and Chemotherapy, vol. 60, No. 8, pp. 4519-4529. (Year: 2016).*
Ingersol, Laura. "Antifungal Activity of Cationic Conjugated Polyelectrolytes and Oligomers against Candida albicans." (2014). https://digitalrepository.unm.edu/biom_etds/82 (Year: 2014).*
"", PubChem. Substance Record for SID 76464254, Retrieved from the Internet. <URL: https://pubchem.ncbi.nlm.nih.gov/substance/76464254#section=Top>, (Jun. 12, 2009), 5 pgs.
"U.S. Appl. No. 16/707,501, Preliminary Amendment filed Dec. 10, 2019", 9 pgs.
"U.S. Appl. No. 12/529,390, Examiner Interview Summary dated Jan. 31, 2012", 3 pgs.
"U.S. Appl. No. 12/529,390, Examiner Interview Summary dated Nov. 13, 2012", 3 pgs.
"U.S. Appl. No. 12/529,390, Non Final Office Action dated Jul. 18, 2012", 7 pgs.
"U.S. Appl. No. 12/529,390, Non-Final Office Action dated Nov. 1, 2011", 11 pgs.
"U.S. Appl. No. 12/529,390, Notice of Allowance dated Feb. 5, 2013", 10 pgs.
"U.S. Appl. No. 12/529,390, Preliminary Amendment dated Sep. 1, 2009", 13 pgs.
"U.S. Appl. No. 12/529,390, Response filed May 1, 2012 to Non Final Office Action dated Nov. 1, 2011", 19 pgs.
"U.S. Appl. No. 12/529,390, Response filed Dec. 18, 2012 to Non Final Office Action dated Jul. 18, 2012", 16 pgs.
"U.S. Appl. No. 13/001,478, Response filed Dec. 19, 2013 to Non Final Office Action dated Oct. 3, 2013", 10 pgs.
"U.S. Appl. No. 13/001,478, Non Final Office Action dated Oct. 3, 2013", 6 pgs.
"U.S. Appl. No. 13/001,478, Notice of Allowance dated Jan. 31, 2014", 7 pgs.
"U.S. Appl. No. 13/001,478, Preliminary Amendment filed Dec. 27, 2010", 1 pg.
"U.S. Appl. No. 13/001,478, Response filed Jul. 11, 2013 to Restriction Requirement dated Jun. 13, 2013", 9 pgs.
"U.S. Appl. No. 13/001,478, Restriction Requirement dated Jun. 13, 2013", 7 pgs.
"U.S. Appl. No. 13/128,571, Response filed Nov. 19, 2012 to Restriction Requirement dated Oct. 17, 2012", 6 pgs.
"U.S. Appl. No. 13/128,571, Non Final Office Action dated Feb. 13, 2013", 10 pgs.
"U.S. Appl. No. 13/128,571, Notice of Allowance dated Aug. 28, 2013", 9 pgs.
"U.S. Appl. No. 13/128,571, Preliminary Amendment filed May 10, 2011", 5 pgs.
"U.S. Appl. No. 13/128,571, Preliminary Amendment filed May 31, 2011", 3 pgs.
"U.S. Appl. No. 13/128,571, Response filed May 13, 2013 to Non Final Office Action dated Feb. 13, 2013", 12 pgs.
"U.S. Appl. No. 13/128,571, Restriction Requirement dated Oct. 17, 2012", 6 pgs.
"U.S. Appl. No. 13/503,067, Response filed Mar. 11, 2013 to Non Final Office Action dated Oct. 10, 2012", 11 pgs.
"U.S. Appl. No. 13/503,067, Response filed Jul. 11, 2013 to Final Office Action dated Jun. 6, 2013", 7 pgs.
"U.S. Appl. No. 13/503,067, Final Office Action dated Jun. 6, 2013", 11 pgs.
"U.S. Appl. No. 13/503,067, Non Final Office Action dated Oct. 10, 2012", 11 pgs.
"U.S. Appl. No. 13/503,067, Notice of Allowance dated Aug. 2, 2013", 10 pgs.
"U.S. Appl. No. 13/809,572, Amendment 312 filed Oct. 21, 2016", 5 pgs.
"U.S. Appl. No. 13/809,572, Final Office Action dated Feb. 18, 2016", 20 pgs.
"U.S. Appl. No. 13/809,572, Non Final Office Action dated Sep. 24, 2015", 17 pgs.
"U.S. Appl. No. 13/809,572, Notice of Allowance dated Aug. 10, 2016", 8 pgs.
"U.S. Appl. No. 13/809,572, Preliminary Amendment filed Jan. 10, 2013", 9 pgs.
"U.S. Appl. No. 13/809,572, Response filed Dec. 16, 2015 to Non-Final Office Action dated Sep. 24, 2015", 11 pgs.
"U.S. Appl. No. 13/809,572, Response filed Apr. 22, 2016 to Final Office Action dated Apr. 18, 2016", 9 pgs.
"U.S. Appl. No. 13/809,573, 312 Amendment filed Jul. 30, 2018", 3 pgs.
"U.S. Appl. No. 13/809,573, Corrected Notice of Allowability dated Sep. 7, 2018", 4 pgs.
"U.S. Appl. No. 13/809,573, Final Office Action dated Dec. 15, 2016", 15 pgs.
"U.S. Appl. No. 13/809,573, Non Final Office Action dated Jan. 22, 2016", 13 pgs.
"U.S. Appl. No. 13/809,573, Non Final Office Action dated Aug. 25, 2016", 13 pgs.
"U.S. Appl. No. 13/809,573, Non Final Office Action dated Oct. 11, 2017", 12 pgs.
"U.S. Appl. No. 13/809,573, Notice of Allowance dated May 17, 2018", 7 pgs.
"U.S. Appl. No. 13/809,573, Preliminary Amendment filed Jan. 10, 2013", 9 pgs.
"U.S. Appl. No. 13/809,573, PTO Response to Rule 312 Communication dated Aug. 3, 2018", 2 pgs.
"U.S. Appl. No. 13/809,573, Response filed Jan. 10, 2018 to Non-Final Office Action dated Oct. 11, 2017", 13 pgs.
"U.S. Appl. No. 13/809,573, Response filed Apr. 17, 2017 to Final Office Acton dated Dec. 15, 2016", 17 pgs.
"U.S. Appl. No. 13/809,573, Response filed Sep. 24, 2015 to Restriction Requirement dated Jul. 24, 2015", 9 pgs.
"U.S. Appl. No. 13/809,573, Response filed Apr. 22, 2016 to Non-Final Office Action dated Jan. 22, 2016", 13 pgs.
"U.S. Appl. No. 13/809,573, Response filed Sep. 22, 2016 to Non-Final Office Actino dated Aug. 25, 2016", 18 pgs.
"U.S. Appl. No. 13/809,573, Restriction Requirement dated Jul. 24, 2015", 7 pgs.
"U.S. Appl. No. 13/993,026 Response filed Sep. 8, 2015 to Final Office Action dated Jun. 8, 2015", 10 pgs.
"U.S. Appl. No. 13/993,026, Advisory Action dated Sep. 17, 2015", 7 pgs.
"U.S. Appl. No. 13/993,026, Final Office Action dated Jun. 8, 2015", 15 pgs.
"U.S. Appl. No. 13/993,026, Non Final Office Action dated Jan. 27, 2015", 9 pgs.
"U.S. Appl. No. 13/993,026, Preliminary Amendment filed Jun. 10, 2013", 7 pgs.
"U.S. Appl. No. 13/993,026, Response filed Apr. 9, 2015 to Non Final Office Action dated Jan. 27, 2015", Response to Non Final Office Action, 11 pgs.
"U.S. Appl. No. 14/092,409, Notice of Allowance dated Dec. 10, 2014", 10 pgs.

(56) References Cited

OTHER PUBLICATIONS

"U.S. Appl. No. 14/092,409, Preliminary Amendment filed Nov. 25, 2014", 4 pgs.
"U.S. Appl. No. 14/092,409, Preliminary Amendment filed Dec. 3, 2013", 4 pgs.
"U.S. Appl. No. 14/127,465, Non Final Office Action dated Jan. 21, 2015", 4 pgs.
"U.S. Appl. No. 14/127,465, Notice of Allowance dated Apr. 30, 2015", 7 pgs.
"U.S. Appl. No. 14/127,465, Preliminary Amendment filed Dec. 18, 2013", 8 pgs.
"U.S. Appl. No. 14/127,465, Response filed Apr. 20, 2015 to Non Final Office Action dated Jan. 21, 2015", 9 pgs.
"U.S. Appl. No. 14/233,130, 312 Amendment dated Nov. 11, 2016", 3 pgs.
"U.S. Appl. No. 14/233,130, Final Office Action dated Jun. 29, 2016", 16 pgs.
"U.S. Appl. No. 14/233,130, Notice of Allowance dated Sep. 12, 2016", 13 pgs.
"U.S. Appl. No. 14/233,130, Preliminary Amendment filed Jan. 15, 2014", 11 pgs.
"U.S. Appl. No. 14/233,130, PTO Response to Rule 312 Communication dated Dec. 8, 2016", 2 pgs.
"U.S. Appl. No. 14/233,130, Response filed Dec. 10, 2015 to Restriction Requirement dated Oct. 22, 2015", 12 pgs.
"U.S. Appl. No. 14/233,130, Response filed Aug. 12, 2016 to Final Office Action dated Jun. 29, 2016", 13 pgs.
"U.S. Appl. No. 14/533,612, Advisory Action dated Nov. 24, 2017", 5 pgs.
"U.S. Appl. No. 14/533,612, Final Office Action dated Jul. 13, 2017", 11 pgs.
"U.S. Appl. No. 14/533,612, Non Final Office Action dated Jan. 20, 2017", 11 pgs.
"U.S. Appl. No. 14/533,612, Notice of Allowance dated Jan. 8, 2018", 8 pgs.
"U.S. Appl. No. 14/533,612, Response filed Oct. 11, 2016 to Restriction Requirement dated Aug. 25, 2016", 8 pgs.
"U.S. Appl. No. 14/533,612, Response filed Oct. 12, 2017 to Final Office Action dated Jul. 13, 2017", 15 pgs.
"U.S. Appl. No. 14/533,612, Response filed Dec. 12, 2017 to Final Office Action dated Jul. 13, 2017", 16 pgs.
"U.S. Appl. No. 14/533,612, Response filed Apr. 20, 2017 to Non-Final Office Action dated Jan. 20, 2017", 11 pgs.
"U.S. Appl. No. 14/533,612, Restriction Requirement dated Aug. 25, 2016", 8 pgs.
"U.S. Appl. No. 15/018,179, Non Final Office Action dated Dec. 13, 2016", 12 pgs.
"U.S. Appl. No. 15/018,179, Notice of Allowance dated May 3, 2017", 9 pgs.
"U.S. Appl. No. 15/018,179, Response filed Sep. 9, 2016 to Restriction Requirement dated Jul. 13, 2016", 15 pgs.
"U.S. Appl. No. 15/018,179, Response filed Mar. 10, 2017 to Non-Final Office Action dated Dec. 13, 2016", 13 pgs.
"U.S. Appl. No. 15/018,179, Restriction Requirement dated Jul. 13, 2016", 10 pgs.
"U.S. Appl. No. 15/125,896, 312 Amendment filed Nov. 7, 2019", 3 pgs.
"U.S. Appl. No. 15/125,896, Final Office Action dated Feb. 11, 2019", 9 pgs.
"U.S. Appl. No. 15/125,896, Non-Final dated Sep. 11, 2018", 17 pgs.
"U.S. Appl. No. 15/125,896, Notice of Allowance dated Aug. 12, 2019", 12 pgs.
"U.S. Appl. No. 15/125,896, Preliminary Amendment dated Sep. 13, 2016", 11 pgs.
"U.S. Appl. No. 15/125,896, PTO Response to Rule 312 Communication dated Nov. 19, 2019", 2 pgs.
"U.S. Appl. No. 15/125,896, Response filed Dec. 6, 2018 to Non0Final Office Action dated Sep. 11, 2018", 16 pgs.
"U.S. Appl. No. 15/125,896, Response filed May 23, 2018 to Restriction Requirement dated Mar. 27, 2018", 12 pgs.
"U.S. Appl. No. 15/125,896, Restriction Requirement dated Mar. 27, 2018", 6 pgs.
"U.S. Appl. No. 15/348,756, Examiner Interview Summary dated Jun. 28, 2018", 2 pgs.
"U.S. Appl. No. 15/348,756, Final Office Action dated Nov. 8, 2017", 25 pgs.
"U.S. Appl. No. 15/348,756, Non Final Office Action dated Mar. 9, 2018", 29 pgs.
"U.S. Appl. No. 15/348,756, Non Final Office Action dated Jun. 23, 2017", 26 pgs.
"U.S. Appl. No. 15/348,756, Notice of Allowability dated Sep. 20, 2018", 5 pgs.
"U.S. Appl. No. 15/348,756, Notice of Allowance dated Aug. 24, 2018", 11 pgs.
"U.S. Appl. No. 15/348,756, Preliminary Amendment filed Nov. 18, 2016 to", 7 pgs.
"U.S. Appl. No. 15/348,756, PTO Response to Rule 312 Communication dated Oct. 3, 2018", 2 pgs.
"U.S. Appl. No. 15/348,756, Response filed Jan. 18, 2018 to Final Office Action dated Nov. 8, 2017", 10 pgs.
"U.S. Appl. No. 15/348,756, Response filed May 31, 2018 to Non-Final Office Action dated Mar. 9, 2018", 12 pgs.
"U.S. Appl. No. 15/348,756, Response filed Sep. 25, 2017 to Non-Final Office Action dated Jun. 23, 2017", 10 pgs.
"U.S. Appl. No. 15/368,148, Non Final Office Action dated Jul. 6, 2017", 16 pgs.
"U.S. Appl. No. 15/368,148, Notice of Allowance dated Jan. 30, 2018", 16 pgs.
"U.S. Appl. No. 15/368,148, Preliminary Amendment filed Dec. 2, 2016", 10 pgs.
"U.S. Appl. No. 15/368,148, Response filed Jun. 12, 2017 to Restriction Requirement dated Apr. 12, 2017", 10 pgs.
"U.S. Appl. No. 15/368,148, Response filed Nov. 6, 2017 to Non-Final Office Action dated Jul. 6, 2017", 17 pgs.
"U.S. Appl. No. 15/368,148, Restriction Requirement dated Apr. 12, 2017", 11 pgs.
"U.S. Appl. No. 16/192,248, Final Office Action dated Nov. 18, 2019", 33 pgs.
"U.S. Appl. No. 16/192,248, Non Final Office Action dated May 30, 2019", 34 pgs.
"U.S. Appl. No. 16/192,248, Preliminary Amendment filed Nov. 15, 2018", 8 pgs.
"U.S. Appl. No. 16/192,248, Response filed Sep. 30, 2019 to Non-Final Office Action dated May 30, 2019", 10 pgs.
"U.S. Appl. No. 14/233,130, Non Final Office Action dated Jan. 14, 2016", 14 pgs.
"U.S. Appl. No. 14/233,130, Response filed Apr. 1, 2016 to Non-Final Office Action dated Jan. 14, 2016", 14 pgs.
"U.S. Appl. No. 14/233,130, Restriction Requirement dated Oct. 22, 2015", 11 pgs.
"U.S. Appl. No. 14/533,612, Notice of Publication mailed", 1 pg.
"European Application Serial No. 09771137.8, Office Action dated Feb. 9, 2011", 1 pg.
"European Application Serial No. 09771137.8, Office Action dated Feb. 14, 2011", 2 pgs.
"European Application Serial No. 09771137.8, Office Action dated Mar. 3, 2011", 1 pg.
"European Application Serial No. 09771137.8, Office Action dated Mar. 16, 2011", 1 pg.
"European Application Serial No. 09771137.8, Response filed Feb. 18, 2011 to Office Action dated Feb. 9, 2011", 6 pgs.
"European Application Serial No. 09771137.8, Search Report dated Nov. 4, 2013", 6 pgs.
"European Application Serial No. 16737889.2, Extended European Search Report dated Mar. 21, 2018", 7 pgs.
"International Application Serial No. PCT/US2008/002756, International Preliminary Report on Patentability dated Sep. 1, 2009", 6 pgs.
"International Application Serial No. PCT/US2008/002756, International Search Report dated Feb. 25, 2009", 2 pgs.

(56) References Cited

OTHER PUBLICATIONS

"International Application Serial No. PCT/US2008/002756, Written Opinion dated Feb. 25, 2009", 5 pgs.
"International Application Serial No. PCT/US2009/048838, International Preliminary Report on Patentability dated Jan. 5, 2011", 7 pgs.
"International Application Serial No. PCT/US2009/048838, International Search Report dated Apr. 30, 2010", 4 pgs.
"International Application Serial No. PCT/US2009/048838, Written Opinion dated Apr. 30, 2010", 6 pgs.
"International Application Serial No. PCT/US2009/063715, International Preliminary Report on Patentability dated May 10, 2011", 6 pgs.
"International Application Serial No. PCT/US2009/063715, International Search Report dated May 27, 2010", 4 pgs.
"International Application Serial No. PCT/US2009/063715, Written Opinion dated May 27, 2010", 5 pgs.
"International Application Serial No. PCT/US2010/052332, International Preliminary Report on Patentability dated Apr. 11, 2012", 7 pgs.
"International Application Serial No. PCT/US2010/052332, International Search Report dated Jun. 24, 2011", 4 pgs.
"International Application Serial No. PCT/US2010/052332, Written Opinion dated Jun. 24, 2011", 6 pgs.
"International Application Serial No. PCT/US2011/043908, International Preliminary Report on Patentability dated Jan. 15, 2013", 7 pgs.
"International Application Serial No. PCT/US2011/043908, International Search Report and Written Opinion dated Apr. 6, 2012", 11 pgs.
"International Application Serial No. PCT/US2011/043922, International Preliminary Report on Patentability dated Jan. 15, 2013", 4 pgs.
"International Application Serial No. PCT/US2011/043922, International Search Report dated Mar. 19, 2012", 3 pgs.
"International Application Serial No. PCT/US2011/043922, Written Opinion dated Mar. 19, 2012", 3 pgs.
"International Application Serial No. PCT/US2011/064460, International Preliminary Report on Patentability dated Jun. 20, 2013", 7 pgs.
"International Application Serial No. PCT/US2011/064460, International Search Report dated Jun. 19, 2012", 6 pgs.
"International Application Serial No. PCT/US2011/064460, Written Opinion dated Jun. 19, 2012", 5 pgs.
"International Application Serial No. PCT/US2012/045598, International Preliminary Report on Patentability dated Jan. 23, 2014", 6 pgs.
"International Application Serial No. PCT/US2012/045598, International Search Report dated May 27, 2013", 3 pgs.
"International Application Serial No. PCT/US2012/045598, Written Opinion dated May 27, 2013", 4 pgs.
"International Application Serial No. PCT/US2012/049613, International Preliminary Report on Patentability dated Feb. 13, 2014", 9 pgs.
"International Application Serial No. PCT/US2012/049613, International Search Report dated Feb. 26, 2013", 3 pgs.
"International Application Serial No. PCT/US2012/049613, Written Opinion dated Feb. 26, 2013", 7 pgs.
"International Application Serial No. PCT/US2015/020546, International Preliminary Report on Patentability dated Sep. 22, 2016", 7 pgs.
"International Application Serial No. PCT/US2015/020546, International Search Report dated Aug. 10, 2015", 4 pgs.
"International Application Serial No. PCT/US2015/020546, Invitation to Pay Additional Fees and Partial Search Report dated May 20, 2015", 2 pgs.
"International Application Serial No. PCT/US2015/020546, Written Opinion dated Aug. 10, 2015", 5 pgs.
"International Application Serial No. PCT/US2016/013431, International Preliminary Report on Patentability dated Jul. 27, 2017", 9 pgs.
"International Application Serial No. PCT/US2016/013431, International Search Report dated Apr. 25, 2016", 3 pgs.
"International Application Serial No. PCT/US2016/013431, Written Opinion dated Apr. 25, 2016", 7 pgs.
"Japanese Application Serial No. 2017-554255, Office Action dated Jan. 9, 2018", with machine translation, 5 pgs.
"Japanese Application Serial No. 2017-554255, Office Action dated Apr. 17, 2018", w/ English translation, 11 pgs.
"Japanese Application Serial No. 2017-554255, Response filed Apr. 3, 2018 to Office Action dated Jan. 9, 2018", (W/ English Claims), 17 pgs.
"Korean Application Serial No. 10-2017-7022348, Notice of Preliminary Rejection dated May 16, 2018", with English translation of claims, 4 pgs.
"Korean Application Serial No. 10-2017-7022348, Response filed Jul. 12, 2018 to Notice of Preliminary Rejection dated May 16, 2018", with English translation of claims, 9 pgs.
Addinall, Stephen, et al., "Temperature Shift Experiments with an ftsZ84(Ts) Strain Reveal Rapid Dynamics of FtsZ Localization and Indicate hat the Z Ring Is Required throughout Septation and Cannot Reoccupy Division Sites Once Constriction Has Initiated", J. of Bacteriology, vol. 179, No. 13, (1997), 4277-4284.
Ambade, A. V, et al., "Fluorescent Polyelectrolytes as Protein Sensors", In: Polym. Int., 2007, vol. 56, (2007), 474-481.
Anderson, David E, et al., "Assembly Dynamics of FtsZ Rings in Bacillus subtilis and *Escherichia coli* and Effects of FtsZ-Regulating Proteins", Journal of Bacteriology, 186(17)., (2004), 5775-5781.
Antoci, Jr., Valentin, et al., "Vancomycin covalently bonded to titanium alloy prevents bacterial colonization", Journal of Orthopaedic Research, 25(7), (2007), 858-866.
Arnt, Lachelle, et al., "Cationic Facially Amphiphilic Poly(phenylene ethynylene)s Studied at the Air-Water Interface", Langmuir, 19(6), (2004), 2404-2408.
Arnt, Lachelle, et al., "New Poly(phenyleneethynylene)s with Cationic, Facially Amphiphilic Structures", Journal of the American Chemical Society,124(26), (2002), 7664-7665.
Arnt, Lachelle, et al., "Nonhemolytic Abiogenic Polymers as Antimicrobial Peptide Mimics", J. Polym. Sci., Part A: Polym. Chem., 42(15), (2004), 3860-3864.
Bartlett, Grant R., "Phosphorus Assay in Column Chromatography", The Journal of Biological Chemistry, 234(3), (1959), 466-468.
Beaujuge, Pierre M., et al., "Spectral Engineering in pie-Conjugated Polymers with Intramolecular Donor-Acceptor Interactions", Accounts of Chemical Research, 43(11), (Nov. 2010), 1396-1407.
Beckloff, Nicholas, et al., "Activity of an Antimicrobial Peptide Mimetic against Planktonic and Biofilm Cultures of Oral Pathogens", Antimicrobial Agents and Chemotherapy, 51, (2007), 4125-4132.
Boeneman, Kelly, et al., "*Escherichia coli* DnaA forms helical structures along the longitudinal cell axis distinct from MreB filaments", Molecular Microbiology, 72(3)., (2009), 645-657.
Bruns, R., et al., "Chapter 3—R&D in material protection: New biocides", In: Directory of Microbicides for the Protection of Materials—A Handbook, Paulus, W., Editor, (2005), 25-46.
Buffet-Bataillon, Sylvie, et al., "Emergence of resistance to antibacterial agents: the role of quaternary ammonium compounds—a critical review", International Journal of Antimicrobial Agents, 39(5)., (2012), 381-389.
Burton, Paul, et al., "Two Pathways of Division Inhibition in UV-Irradiated *E. coli*", Mol Gen Genet., 190(1)., (1983), 128-132.
Cabiscol, Elisa, et al., "Oxidative stress in bacteria and protein damage by reactive oxygen species", International Microbiology, 3., (2000), 3-8.
Capuano, Ben, et al., "The Synthesis and Preliminary Pharmacological Evaluation of a Series of Substituted 4'-Phenoxypropyl Analogues of the Atypical Antipsychotic Clozapine", Aust. J. Chem., 63, (2010), 116-124.

(56) References Cited

OTHER PUBLICATIONS

Ceri, H., et al., "The Calgary Biofilm Device: New Technology for Rapid Determination of Antibiotic Susceptibilities of Bacterial Biofilms", Journal of Clinical Microbiology, 37(6), (1999), 1771-1776.

Chamchod, Farida, et al., "Modeling methicillin-resistant *Staphylococcus aureus* in hospitals: Transmission dynamics, antibiotic usage and its history", Theor Biol Med Model., 9, 25., (2012), 1-14.

Chemburu, et al., "Conjugated Polyelectrolyte Supported Bead Based Assays for Phospholipase A2 Activity", (2008), 14492-14499.

Chemburu, Sireesha, et al., "Light-Induced Biocidal Action of Conjugated Polyelectrolytes Supported on Colloids", Langmuir, 24, (2008), 11053-11062.

Choi, W. S., et al., "Synthesis of Two Types of Nanoparticles in Polyelectrolyte Capsule Nanoreactors and Their Dual Functionality", J. Am. Chem. Soc., 127, (2005), 16136-16142.

Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.

Cooper, B S, et al., "Methicillin-resistant *Staphylococcus aureus* in hospitals and the community: Stealth dynamics and control catastrophes", Proc. Nat. Acad. Sci., 2004, 101(27),, (2004), 10223-10228.

Corbitt, Thomas, et al., "Antimicrobial Non-Woven Fibrous Materials", U.S. Appl. No. 61/528,603, filed Aug. 29, 2011, 17 pgs.

Corbitt, Thomas S., et al., "Conjugated Polyelectrolyte Capsules: Light-Activated Antimicrobial Micro "Roach Motels"", ACS Appl. Mater. Interfaces, 1(1), (2009), 48-52.

Corbitt, Thomas S., et al., "Light and dark biocidal activity of cationic poly(arylene ethynylene) conjugated polyelectrolytes", Photochem. Photobiol. Sci., 8, (2009), 998-1005.

Costerton, J. William, et al., "Mechanism of Electrical Enhancement of Efficacy of Antibiotics in Killing Biofilm Bacteria", Antimicrobial Agents and Chemotherapy, 38(12), (1994), 2803-2809.

Cramton, Sarah, et al., "The Intercellular Adhesion (ica) Locus Is Present in *Staphylococcus aureus* and Is Required for Biofilm Formation", Infection and Immunity, 67(10)., (1999), 5427-5433.

Dascier, Dimitri, et al., "Efficacy of End-Only-Functionalized Oligo(arylene-ethynylene)s in Killing Bacterial Biofilms", Langmuir, 28(31), (2012), 11286-11290.

De Geest, B. G., et al., "Release mechanisms for polyelectrolyte capsules", Chem. Soc. Rev., 36, (2007), 636-649.

Ding, Liping, et al., "Insight into the Mechanism of Antimicrobial Poly(phenylene ethynylene) Polyelectrolytes: Interactions with Phosphatidylglycerol Lipid Membranes", Langmuir, 25(24), (2009), 13742-13751.

Donlan, Rodney M., et al., "Microbial Life on Surfaces", Emerging Infectious Diseases, 8(9), (2002), 881-890.

Eun, Ye-Jin, et al., "Fabrication of Microbial Biofilm Arrays by Geometric Control of Cell Adhesion", Langmuir, 25(8), (2009), 4643-4654.

Evans, D, et al., "Critical Micelle Concentrations for Alkyltrimethylammonium Bromides in Water from 25 to160° C.", J. Solution Chem., 13(2)., (1984), 87-101.

Fan, Qu-Li, et al., "Water-Soluble Cationic Poly(p-phenyleneethynylene)s (PPEs): Effects of Acidity and Ionic Strength on Optical Behavior.", Macromolecules.vol. 38, (2005), 2927-2936.

Fang, Zhen, et al., "Low-Bandgap Donor-Acceptor Conjugated Polymer Sensitizers for Dye-Sensitized Solar Cells", Journal of the American Chemical Society, 133(9), (2011), 3063-3069.

Ferreira, Isabel C.F.R, et al., "Screening of antimicrobial activity of diarylamines in the 2,3,5-trimethylbenzo[b]thiophene series a structure-activity evaluation study", Bioorganic & Medicinal Chemistry Letters, 14(23), (2004), 5831-5833.

Flemming, Hans-Curt, et al., "The biofilm matrix", Nat Rev Microbiol., 8(9)., (2010), 623-633.

Galaev, Igor Y., "'Smart' polymers in biotechnology and medicine", Russian Chemical Reviews, 64(5), (1995), 471-489.

Gao, Yuan, et al., "Recent Advances in Antimicrobial tTeatment of Textiles", Textile Research Journal, 78(1), (2008), 60-72.

Gaylord, Brent, et al., "DNA Hybridization Detection with Water-Soluble Conjugated Polymers and Chromophore-Labeled Single-Stranded DNA", Journal of the American Chemical Society, vol. 125, No. 4, (Jan. 29, 2003), 896-900.

George, Wayne N., et al., "Amplified fluorescence quenching in high ionic strength media.", Soft Matter. vol. 3, (2007), 1381-1387.

Gilbert, P, et al., "Biofilms in vitro and in vivo: do singular mechanism imply cross-resistance?", J Appl Microbiol.,92 Suppl., (2002), 98S-110S.

Goehring, Nathan, et al., "Diverse Paths to Midcell: Assembly of the Bacterial Cell Division Machinery", Current Biology, 15., (2005), R514-R526.

Gorwitz, R, et al., "More Challenges in the Prevention and Management of Community-Associated, Methicillin-Resistant *Staphylococcus aureus* Skin Disease", Ann. Intern. Med.,148 (4)., (2008), 310-312.

Guan, Bin, et al., "Different Functionalization of the Internal and External Surfaces in Mesoporous Materials for Biosensing Applications Using "Click" Chemistry", Langmuir, 27(1), (2010), 328-334.

Harrison, Joe J., et al., "Microtiter susceptibility testing of microbes growing on peg lids: a miniaturized biofilm model for high-throughput screening", Nature Protocols, 5(7), (2010), 1236-1254.

Hill, Eric, et al., "Cationic oligo-p-phenylene ethynylenes form complexes with surfactants for long-term light-activated biocidal applications", Photochem. Photobiol. Sci., 13., (2014), 247-253.

Hill, Eric, et al., "Molecular Dynamics Simulation Study of the Interaction of Cationic Biocides with Lipid Bilayers: Aggregation Effects and Bilayer Damage", Langmuir 28, (2012), 14849-14854.

Hill, Eric, et al., "Photochemistry of "End-Only" Oligo-p-phenylene Ethynylenes: Complexation with Sodium Dodecyl Sulfate Reduces Solvent Accessibility", Langmuir, 29(31), (2013), 9712-9720.

Hill, Eric H, et al., "The influence of structured interfacial water on the photoluminescence of carboxyester-terminated oligo-p-phenylene ethynylenes", Journal of Physical Organic Chemistry, 27:252-257, (2014), 7 pgs.

Hoffman, Allan S., "Bioconjugates of Intelligent Polymers and Recognition Proteins for Use in Diagnostics and Affinity Separations", Clinical Chemistry, 46:9, (2000), 1478-1486.

Hortholary, Cedric, et al., "An Approach to Long and Unsubstituted Molecular Wires: Synthesis of Redox-Active, Cationic Phenylethynyl Oligomers Designed for Self-Assembled Monolayers", J. Org. Chem., 68(6), (2003), 2167-2174.

Huisgen, Rolf, "Centenary Lecture—1,3-Dipolar Cycloadditions", Proceedings of the Chemical Society of London, (Oct. 1961), 357-369.

Ibraeva, Zhanar E., et al., "Solution Properties and Complexation of Polyampholytes based on N,N-Dimethyldiallyl-ammonium Chloride and Maleic Acid or Alkyl (Aryl) Derivatives of Malemic Acids", Macromol. Chem. Phys., 205, (2004), 2464-2472.

Ista, Linnea K., et al., "Conjugated-Polyelectrolyte-Grafted Cotton Fibers Act as "Micro Flypaper" for the Removal and Destruction of Bacteria", ACS Applied Materials & Interfaces, 3(8), (2011), 2932-2937.

Ji, E., "Conjugated polyelectrolytes: Synthesis, photophysical studies and applications to sensors and biocidal activity", Ph.D. dissertation, Univ. of Florida, 2009, (2009), 167 pgs.

Ji, E., et al., "pH-Dependent Optical Properties of a Poly(phenylene ethynylene) Conjugated Polyampholyte", In: Langmuir, vol. 27, (Dec. 28, 2010), 1565-1568.

Ji, Eunkyung, et al., "Antibacterial Activity of Conjugated Polyelectrolytes with Variable Chain Lengths", Langmuir, 27, (2011), 10763-10769.

Ji, Eunkyung, et al., "Light and Dark-Activated Biocidal Activity of Conjugated Polyelectrolytes", ACS Applied Materials & Interfaces, 3(8), (2011), 2820-2829.

Jiang, Hui, et al., "Conjugated Polyelectrolytes: Synthesis, Photophysics, and Applications", Angew. Chem. Int. Ed., 48(24), (2009), 4300-4316.

(56) References Cited

OTHER PUBLICATIONS

Jiang, Hui, et al., "Effects of Polymer Aggregation and Quencher Size on Amplified Fluorescence Quenching of Conjugated Polyelectrolytes", Langmuir, 23(18), (2007), 9381-9486.
Jones, Tineke, "Response of *Escherichia coli* to Environmental Stress", Stress Response of Foodborne Microorganisms. NovaScience Publishers., (2012), 293-330.
Kenawy, El-Refaie, et al., "The Chemistry and Applications of Antimicrobial Polymers: A State-of-the-Art Review", Biomacromolecules, 8(5), (2007), 1359-1384.
Kilger, Robert, et al., "Bidirectional energy transfer between the triplet T1 state of photofrin and singlet oxygen in deuterium oxide", Chemical Physics Letter 343, (2001), 543-548.
Kim, Chae Kyu, et al., "Complexation of Anionic Conjugated Polyelectrolyte with Cationic Surfactant", Macromolecular Research, vol. 13 No. 5, (2005), 460-462.
Kim, Sook Kyung, et al., "Chemosensors for Pyrophosphate", Accounts of Chemical Research 42, (2009), 23-31.
Klevens, R M, et al., "Estimating Health Care-Associated Infections and Deaths in U.S. Hospitals", Public Health Rep., 2007, 122(2)., (2002), 160-166.
Kolb, Hartmuth C., et al., "Click Chemistry: Diverse Chemical Function from a Few Good Reactions", Angew. Chem. Int. Ed., 40, (2001), 2004-2021.
Kotz, Joachim, "Inter- and intramolecular interactions in polyelectrolyte complex formation with polyampholytes", Macromolecular Chemistry and Physics, 194(2), (1993), 397-410.
Kruse, T, et al., "Dysfunctional MreB inhibits chromosome segregation in *Escherichia coli*", EMBO J., 22(19)., (2003), 5283-5292.
Leach, Michelle K., et al., "Electrospinning Fundamentals: Optimizing Solution and Apparatus Parameters", Journal of Visualized Experiments, 47, (2011), 4 pgs.
Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.
Lee, Wen-Fu, et al., "Synthesis and solubility of the poly(sulfobetaine)s and the corresponding cationic polymers: 2. Aqueous solution properties of poly[ N,N'-dimethyl-(acrylamido propyl) ammonium propane sulfonate]", Polymer, 36(2), (1995), 357-364.
Leid, Jeff, et al., "Human Leukocytes Adhere to Penetrate, and Respond to *Staphylococcus aureus* Bio?lms", Infection and Immunity, 70(11)., (2002), 6339-6345.
Lin, Ching-Yao, et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", J. Phys. Chem. C., 113(2), (2009), 755-764.
Lindig, Barbara, et al., "Determination of the Lifetime of Singlet Oxygen in D20 Using 9, IO-Anthracenedipropionic Acid, a Water-Soluble Probe", J. Am. Chem. Soc., 102 (17)., (1980), 5590-5593.
Lindsay, D., et al., "Bacterial biofilms within the clinical setting: what healthcare professionals should know", Journal of Hospital Infection, 64, (2006), 313-325.
Liu, Yan, et al., "Conjugated Polyelectrolyte-Based Real-Time Fluorescence Assay for Alkaline Phosphatase with Pyrophosphate as Substrate", Anal. Chem. 80, (2008), 8605-8612.
Liu, Yan, et al., "Conjugated polyelectrolytes as fluorescent sensors", Journal of Photochemistry and Photobiology C: Photochemistry Reviews, 10(4), (2009), 173-190.
Lock, Rowena, et al., "Cell-division inhibitors: new insights for Future anibiotics", Nature Reviews Drug Discovery, 7., (2008), 324-338.
Lowe, Andrew B., et al., "Synthesis and Solution Properties of Zwitterionic Polymers", Chem. Rev., 102, (2002), 4177-4189.
Lu, L., et al., "Biocidal Activity of a Light-Absorbing Fluorescent Conjugated Polyelectrolyte", Langmuir, 21, (2005), 10154-10159.
Lu, Timothy K., et al., "Dispersing biofilms with engineered enzymatic bacteriophage", Proc. Natl. Acad. Sci. USA, 104(27), (2007), 11197-11202.

Maciag-Dorszynska, Monika, et al., "Mutations in central carbon metabolism genes suppress defects in nucleoid position and cell division of replication mutants in *Escherichia coli*", Gene 503., (2012), 31-35.
Magrex-Debar, Elisabeth, et al., "Evaluation of biohazards in dehydrated bio?lms", International Journal of Food Microbiology 55., (2000), 239-243.
Mah, Thien-Fah, et al., "Mechanisms of biofilm resistance to antimicrobial agents", Trends in Microbiology. vol. 9 No. 1., (2001), 34-39.
Maisch, Tim, et al., "The role of singlet oxygen and oxygen concentration in photodynamic inactivation of bacteria", The National Academy of Sciences of the USA. PNAS vol. 104, No. 17, (2007), 7223-7228.
Malik, Zvi, et al., "New Trends in Photobiology (Invited Review) Bactericidal Effects of Photoactivated Porphyrins—An Alternative Approach to Antimicrobial Drugs", Journal of Photochemistry and Photobiology B: Biology, 5(3-4)., (1990), 281-293.
Mann, Ethan, et al., "Modulation of eDNA Release and Degradation Affects *Staphylococcus aureus* Biofilm Maturation", PLOS One, 4(6)., (2009), e5822.
McCormick, C. L., "Polyampholytes (Overview)", In: Polymeric Materials Encyclopedia, vol. 7, CRC Press, Boca Raton, FL, (1996), 5462-5476.
McNeill, Karol, et al., "Acid tolerance response of bio¢lm cells of *Streptococcus* mutans", FEMS Microbiology Letters, 221., (2003), 25-30.
McQuade, D. Tyler, et al., "Signal Amplification of a Turn-On Sensor: Harvesting the Light Captured by a Conjugated Polymer", J. Am. Chem. Soc., 122, (2000), 12389-12390.
Miranda, Oscar R, et al., "Array-Based Sensing of Proteins Using Conjugated Polymers", JACS 129:9856-9857, (2007), 2 pgs.
Narendiran, "Electrospun Ultrathin Nylon Fibers for Protective Applications", Journal of Applied Polymer Science, vol. 116, (Jan. 7, 2010), 2181-2187.
Neuhaus, Francis, et al., "A Continuum of Anionic Charge: Structures and Functions of D-Alanyl-Teichoic Acids in Gram-Positive Bacteria", Microbiology and Molecular Biology Reviews, 67(4)., (2003), 686-723.
Nickerson, Emma, et al., "*Staphylococcus aureus* disease and drug resistance in resource-limited countries in south and east Asia", Lancet Infect. Dis., 9., (2009), 130-135.
Nikaido, Hiroshi, "Outer Membrane", *Escherichia coli* and *Salmonella*: cellular and molecular biology. 2nd ed. Washington, D.C: American Society for Microbiology., (1996), 29-47.
Notestein, Justin M., et al., "Covalent Grafting of m-Phenylene-Ethynylene Oligomers to Oxide Surfaces", Chem. Mater., 22, (2010), 5319-5327.
Ogawa, Katsu, et al., "Conjugated Polyelectrolyte-Grafted Silica Microspheres", Langmuir, 23(8), (2007), 4541-4548.
Olson, Merle E., et al., "Biofilm bacteria: formation and comparative susceptibility to antibiotics", Canadian Journal of Veterinary Research-Revue Canadienne De Recherche Veterinaire, 66, (2002), 86-92.
Parthasarathy, Anand, "Conjugated Polyelectrolytes with Imidazolium Solubilizing Groups Properties and Application to Photodynamic Inactivation of Bacteria", ACS Applied Materials & Interfaces vol. 7, No. 51, (2015), 28027-28034.
Pasquier, Nicolas, et al., "From Multifunctionalized poly(ethylene Imine)s toward Antimicrobial Coatings", Biomacromolecules, 8, (2007), 2874-2882.
Patel, Dinesh G., et al., "It Takes More Than an Imine: The Role of the Central Atom on the Electron-Accepting Abilitty of Benzotriazole and Benzothiadiazole Oligomers", Journal of the American Chemical Society, 134(5), (2012), 2599-2612.
Pinto, Mauricio, et al., "Ampli?ed ?uorescence quenching and biosensor application of a poly (para-phenylene) cationic polyelectrolyte", Res. Chem. Intermed. 33, (2007), 79-90.
Pinto, Mauricio R., et al., "Amplified fluorescence sensing of protease activity with conjugated polyelectrolytes", Proc. Natl. Acad. Sci. USA, 101(20), (2004), 7505-7510.
Pinto, Mauricio R., et al., "Conjugated Polyelectrolytes: Synthesis and Applications", Synthesis, 9, (2002), 1293-1309.

(56) References Cited

OTHER PUBLICATIONS

Potera, Carol, "C. Microbiology—Forging a Link Between Biofilms and Disease", Science, 283(5409), (1999), 1837-1939.
Reddinger, Jerry L., et al., "Molecular Engineering of p-Conjugated Polymers", Radical Polymerisation Polyelectrolytes, Series: Advances in Polymer Science, vol. 145, (1999), 57-122.
Rice, Kelly, et al., "The cidA murein hydrolase regulator contributes to DNA release and biofilm development in *Staphylococcus aureus*", Proc. Nat. Acad. Sci., 104(19)., (2007), 8113-8118.
Rico, Ana Isabel, et al., "Role of *Escherichia coli* FtsN protein in the assembly and stability of the cell division ring", Molecular Microbiology, 76(3)., (2010), 760-771.
Rolinson, George, "Forty years of ß-lactam research", Journal of Antimicrobial Chemotherapy, 41., (1998), 589-603.
Romberg, Laura, et al., "Assembly Dynamics of the Bacterial Cell Division Protein FTSZ: Poised at the Edge of Stability", Annual Review of Microbiology, 57., (2003), 125-154.
Ron, Eliora, et al., "Growth Rate of *Escherichia coli* at Elevated Temperature: Lomitation by Methionine", Journal of Bacteriology, 107(1)., (1971,), 391-396.
Schanze, K. S, et al., "Functional Polyelectrolytes", In: Langmuir, 2009, vol. 25, (2009), 13698-13702.
Schild, H. G., "Poly(N-Isopropylacrylamide): Experiment, Theory and Application", Prog. Polym. Sci., 17, (1992), 163-249.
Schlüter, A. D., "The Tenth Anniversary of Suzuki Polycondensation (SPC)", Journal of Polymer Science Part A: Polymer Chemistry, 39(10), (2001), 1533-1556.
Senthilkumar, Sadasivam, et al., "Photophysical properties of coumarin-30 dye in aprotic and protic solvents of varying polarities", Photochemistry and Photobiology, 80, (2004), 104-111.
Shi, Songqing, et al., "Synthesis and Characterization of a Water-Soluble Poly(p-phenylenevinylene) Derivative", Macromolecules, 23(8), (1990), 2119-2124.
Stewart, Philip, et al., "Antibiotic resistance of bacteria in biofilms", Lancet, 358., (2001), 135-138.
Stewart, Philip S., et al., "Physiological heterogeneity in biofilms", Nature Reviews Microbiology, 6, (Mar. 2008), 199-210.
Storz, Gisela, et al., "Oxidative stress", Current Opinion in Microbiology, 2., (1999), 188-194.
Stricker, Jesse, et al., "Rapid assembly dynamics of the *Escherichia coli* FtsZ-ring demonstrated by fluorescence recovery after photobleaching", Proc. Nat. Acad. Sci., 99(5)., (2002), 3171-3175.
Tacconelli, Evelina, et al., "Does antibiotic exposure increase the risk of methicillin-resistant *Staphylococcus aureus* (MRSA) isolation? a systematic review and meta-analysis", J. Antimicrob. Chemother. ,61(1)., (2008), 26-38.
Tan, et al., "Hyper-Efficient Quenching of a Conjugated Polyelectrolyte by Dye-Doped Silica Nanoparticles: Better Quenching in the Nonaggregated State", Langmuir Letter 26(3), (Nov. 19, 2009), 1528-1532.
Tan, et al., "Thermodynamics of Sodium Dodecyl Sulfate Partitioning into Lipid Membranes", Biophysics Journal vol. 83, (2002), 1547-1556 pgs.
Tan, C, et al., "Photophysics, aggregation and amplified quenching of a water-soluble poly (phenylene ethynylene)", Chem. Commun., (2002), 446-447.
Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.
Tan, Chunyan, et al., "Amplified Quenching of a Conjugated Polyelectrolyte by Cyanine Dyes", J. Am. Chem. Soc., 126, (2004), 13685-13694.
Tang, Yanli, et al., "Light-induced antibacterial activity of symmetrical and asymmetrical oligophenylene ethynylenes", Langmuir, 27(8), (2011), 4956-4962.
Tang, Yanli, et al., "Synthesis, Self-Assembly, and Photophysical Behavior of Oligo Phenylene Ethynylenes: From Molecular to Supramolecular Properties", Langmuir, 25(1), (2009), 21-25.

Tang, Yanli, et al., "Synthesis, Self-Assembly, and Photophysical Properties of Cationic Oligo(p-phenyleneethynylene)s", Langmuir, 27(8), (2011), 4945-4955.
Teitzel, Gail, "Heavy Metal Resistance of Bio?lm and Planktonic Pseudomonas aeruginosa", Applied and Environmental Microbiology, 69(4)., (2003), 2313-2320.
Tew, G. N, et al., "", Biochimica et Biophysica Acta 2006, (2006), 1387-1392.
Thomas, III, Samuel W., et al., "Chemical Sensors Based on Amplifying Fluorescent Conjugated Polymers", Chem. Rev., 107, (2007), 1339-1386.
Tiller, J. C., et al., "Designing surfaces that kill bacteria on contact", Proc. Natl. Acad. Sci. USA, 98(11), (May 22, 2001), 5981-5985.
Tong, W., et al., "Single Polyelectrolyte Microcapsules Fabricated by Glutaraldehyde-Mediated Covalent Layer-By-Layer Assembly", Macromol. Rapid Commun., 27, (2006), 2078-2083.
Trauble, Hermann, et al., "The Structure of *Escherichia coli* Membranes Studied by Fluorescence Measurement of Lipid Phase Transitions", Biophys. Acta, 307., (1973), 491-512.
Turro, J, et al., "Luminescent Probes for Detergent Solutions. A Simple Procedure for Determination of the Mean Aggregation Number of Micelles", J. Am. Chem. Soc., 100., (1978), 5951-5952.
Valle, Jaione, et al., "Broad-spectrum biofilm inhibition by a secreted bacterial polysaccharide", Proc. Natl. Acad. Sci. USA, 103(33), (2006), 12558-12563.
Vollmer, Waldemar, et al., "Peptidoglycan structure and architecture", FEMS Microbial. Rev. 32(2)., (2008), 149-167.
Wallow, Thomas I., et al., "In Aqua Synthesis of Water-Soluble Poly(p-phenylene) Derivatives", J. Am. Chem. Soc., 113, (1991), 7411-7412.
Wang, et al., "Effect of Polymer Chain Length on Membrane Perturbation Activity of Cationic Phenylene Ethynylene Oligomers and Polymers", Langmuir, 27, (Jul. 8, 2011), 10770-10775.
Wang, Deli, et al., "Biosensors from conjugated polyelectrolyte complexes", Proc. Natl. Acad. Sci. USA, 96, (1999), 12287-.
Wang, Deli, et al., "Photoluminescence Quenching of Conjugated Macromolecules by Bipyridinium Derivatives in Aqueous Media: Charge Dependence", Langmuir, 17, (2001), 1262-1266.
Wang, Ying, et al., "Direct Visualization of Bactericidal Action of Cationic Conjugated Polyelectrolytes and Oligomers", Langmuir, 28, (2012), 65-70.
Wang, Ying, et al., "Membrane Perturbation Activity of Cationic Phenylene Ethynylene Oligomers and Polymers: Selectivity against Model Bacterial and Mammalian Membranes", Langmuir, 26(15), (Jun. 29, 2010), 12509-12514.
Wang, Ying, et al., "Understanding the Dark and Light-Enhanced Bactericidal Action of Cationic Conjugated Polyelectrolytes and Oligomers", Langmuir, 29(2)., (2013), 781-792.
Wang, Yingsheng, et al., "Photochemical probes of intramolecular electronc and energy transfer", Chemical Physics, 176, (1993), 305-319.
Wang, Z., et al., "Preparation and application of single polyelectrolyte microcapsules possessing tunable autofluorescent properties.", Colloids and Surfaces A: Physicochemical and Engineering Aspects, 329, (2008), 58-66.
Wosnick, Jordan H., et al., "Synthesis and Application of Poly(phenyleneEthynylene)s for Bioconjugation: A Conjugated Polymer-Based Fluorogenic Probe", American Chemical Society,127, (2005), 3400-3405.
Xu, Shimei, et al., "Effect of the Anionic-Group/Cationic-Group Ratio on the Swelling Behavior and Controlled Release of Agrochemicals of the Amphoteric, Superabsorbent Polymer Poly(acrylic acid-co-diallyldimethylammonium chloride)", Journal of Applied Polymer Science, 102, (2006), 986-991.
Yang, Chaoyong James, et al., "Direct Synthesis of an Oligonucleotide-Poly-(phenylene ethynylene) Conjugate with a Precise One-to-One Molecular Ratio", Angew. Chem. Int. Ed. 44, (2005), 2572-2576.
Zhai, Lei, et al., "A Simple Method to Generate Side-Chain Derivatives of Regioregular Polythiophene via the GRIM Metathesis and Post-polymerization Functionalization", Macromolecules 36, (2003), 61-64.

(56) References Cited

OTHER PUBLICATIONS

Zhang, Lian-Hui, et al., "Quorum sensing and signal interference: diverse implications", Molecular Microbiology, 53(6), (2004), 1563-1571.

Zhao, Xiaoyong, et al., "Variable Band Gap Poly(arylene ethynylene) Conjugated Polyelectrolytes", Macromolecules, 39, (2006), 6355-6366.

Zhinjou, Zhou, "Studies of a cyanine-based biosensor and light-induced antibacterial activities of oligophenyleneethynylenes", Dissertation, Chemistry, University of New Mexico, Albuquerque, NM, (Dec. 2010), 165 pgs.

Zhou, Zhijun, et al., "End-Only" Functionalized Oligo(phenylene ethynylene)s: Synthesis, Photophysical and Biocidal Activity, Journal of Physical Chemistry Letters, 1(21), (2010), 3207-3212.

Zhu, Huiguang, et al., "Synthesis of Size-Controlled Monodisperse Manganese Carbonate Microparticles as Templates for Uniform Polyelectrolyte Microcapsule Formation.", Chern. Mater.,17, (2005), 2323-2328.

* cited by examiner

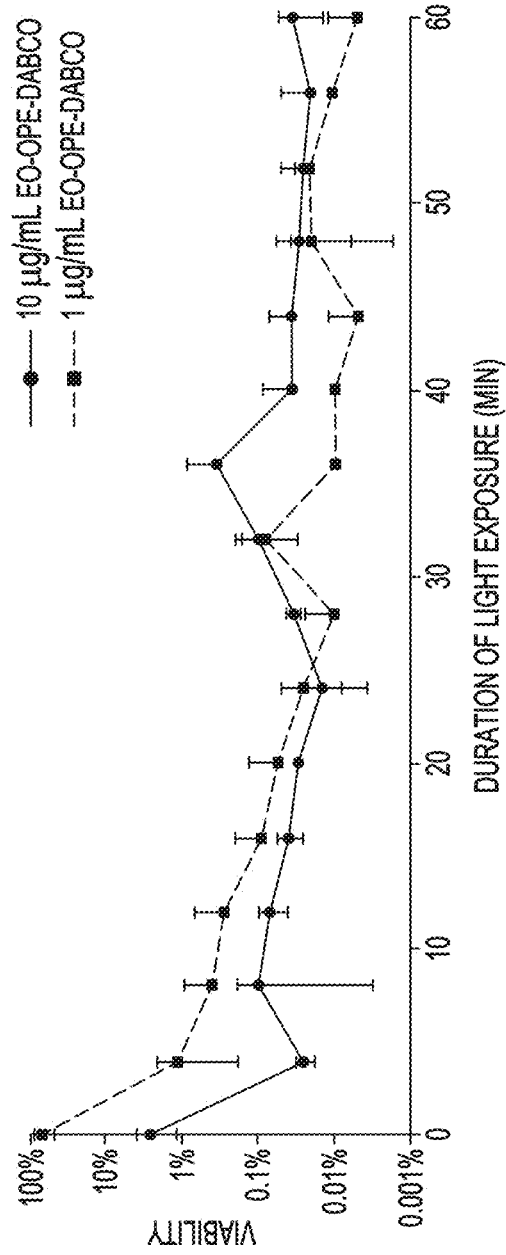
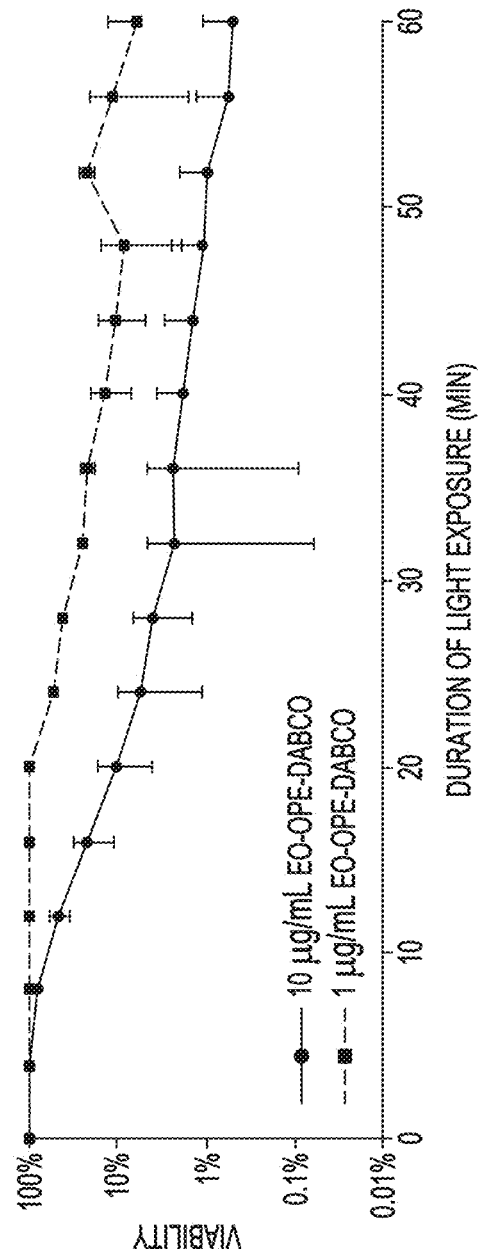
FIG. 1A
FIG. 1B

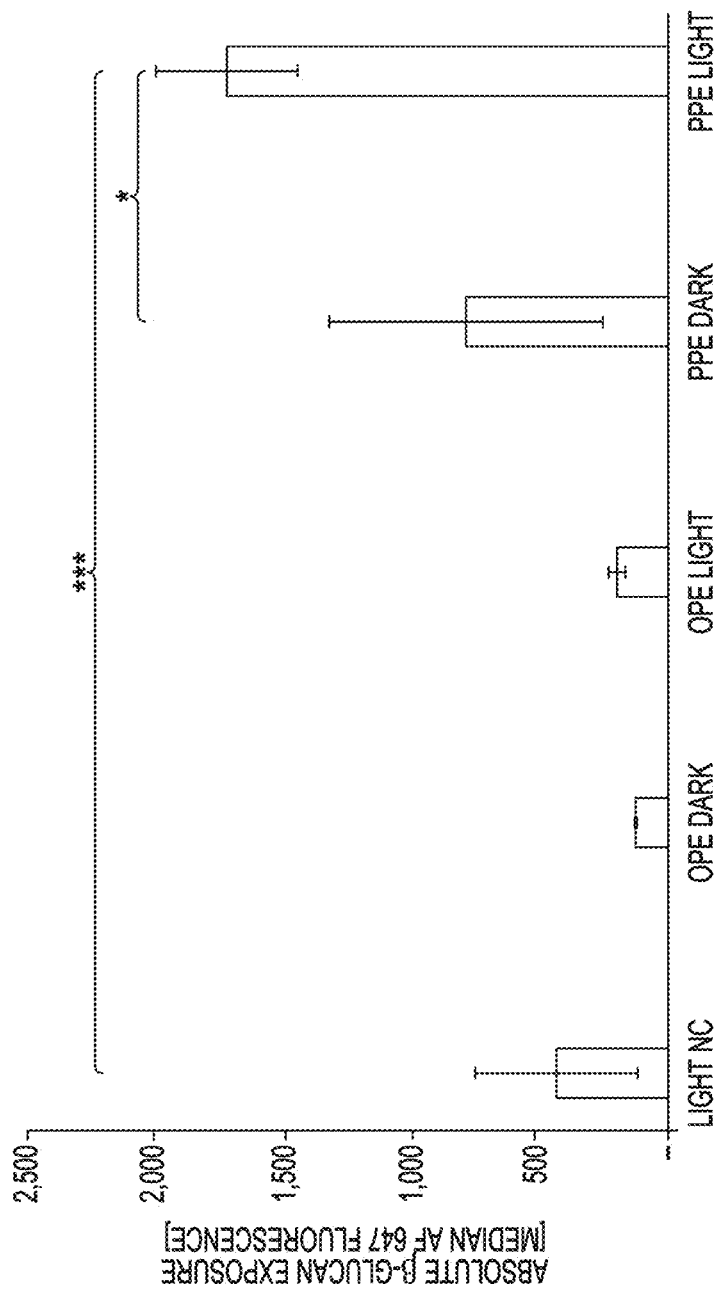

TREATMENT AND PREVENTION OF FUNGAL INFECTIONS

CROSS-REFERENCE TO RELATED APPLICATIONS

This application claims the benefit of priority to U.S. Provisional Patent Application Ser. No. 62/454,355 entitled "TREATMENT AND PREVENTION OF FUNGAL INFECTIONS," filed Feb. 3, 2017, the disclosure of which is incorporated herein in its entirety by reference.

STATEMENT OF GOVERNMENT SUPPORT

This invention was made with Government support under grant number 1R01AI116894-01A1 awarded by the National Institute of Allergy and Infectious Disease. The U.S. Government has certain rights in this invention.

BACKGROUND

Bloodstream infections affect a huge patient population in the United States, with more than 250,000 cases reported each year. Patients with indwelling medical devices, such as central venous catheters (CVCs), are most at risk for these infections. Frequently, various microorganisms from the skin of the patient, or respective healthcare professional, can gain access through the catheter wound as a result of non-sterile conditions. Of these resulting bloodstream infections, Candida species account for 9% of all bloodstream infections and are associated with ~40% mortality rate. The most commonly isolated fungal pathogen from bloodstream infections is *Candida albicans*, but the prevalence of other species, such as *C. parapsdosis*, *C. glabrata*, and *C. tropicalis*, is increasing.

Candida spp. pathogens possess an outer cell wall that is an important determinant of pathogenicity. The cell wall is primarily composed of carbohydrates and structurally is separated into two layers. The outer layer is composed mostly of N-linked glycans and mannoproteins and the inner layer is composed of, β-glucan and chitin. The complexity of the cell wall contributes to various pathogenic factors including adherence of the fungus and establishment of cross-talk with the host known as "glycan code." Cell wall components are also found in the extracellular matrix secreted by Candida spp. biofilms, which can contaminate the synthetic material surfaces of indwelling medical devices. Candida spp. biofilm production of polysaccharides, such as β-glucan, contributes to the decreased susceptibility of biofilms to antifungal drugs by sequestering antifungal drugs.

Various antimicrobial impregnation approaches have been devised to prevent catheter infections. Catheter materials coated with chlorhexidine-silver sulfadiazine and minocycline/rifampin have shown trends in reduced infection rates, but their clinical effectiveness remains questionable. Other treatments, including the use of silver-impregnated subcutaneous collagen cuffs, have also failed to be effective in recent trials. CVC contamination generally requires removal and replacement of the device in addition to a prolonged course of antifungal drug therapy, which raises concerns regarding drug toxicity and development of antifungal resistance. Antifungal chemotherapy is also problematic, with increasing prevalence of resistance to azole and echinocandin drugs as well as well-known nephrotoxicity of amphotericin B. Due to the high morbidity and mortality rate of catheter-related Candida spp. bloodstream infections, strategies for preventing medical device contamination by fungal pathogens remains a top priority for infection control.

SUMMARY OF THE INVENTION

In various embodiments, a method of treating a fungal infection includes contacting a fungus including a β-glucan that is at least partially masked from immune system detection with a therapeutically effective amount of a compound that at least partially unmasks the β-glucan to increase immunogenicity of the fungus.

In various embodiments, a method of treating a fungal infection includes contacting a fungus including a β-glucan that is at least partially masked from immune system surveillance with a therapeutically effective amount of a compound that at least partially unmasks the β-glucan to increase immunogenicity of the fungus, wherein the compound includes a unit having the structure:

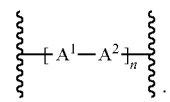

The variable $A^1$ is chosen from a bond,

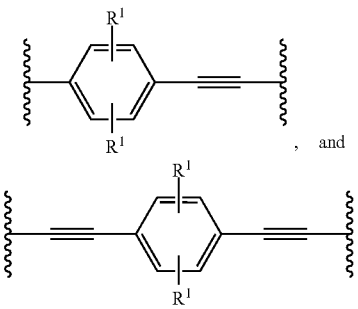

The variable $A^2$ is chosen from a bond,

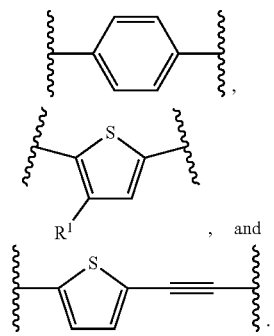

The variable $R^1$ is chosen from —H and $C^1$, wherein the compound includes at least one $C^1$, at each occurrence, $C^1$ is independently chosen from -L-D and —O-L-D, at each occurrence, L is independently $(C_1$-$C_{10})$hydrocarbylene, at each occurrence, D is independently chosen from —N(($C_1$-$C_5$)alkyl)$_3$ and a $(C_1$-$C_{10})$alkyl-substituted cationic nitrogen-containing $(C_1$-$C_5$)heterocycle, and n is about 1 to about 100,000.

In various embodiments, an antifungal compound includes a unit having the structure:

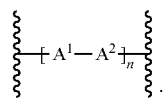

The variable $A^2$ is chosen from a bond,

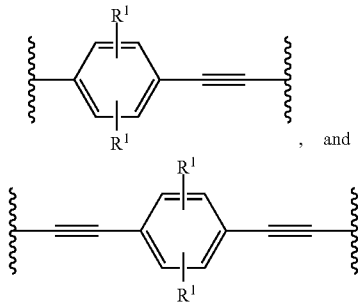

The variable $A^2$ is chosen from a bond,

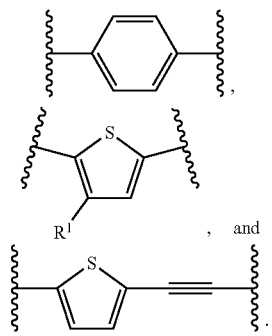

The variable $R^1$ is chosen from —H and $C^1$, wherein the compound includes at least one $C^1$, at each occurrence, $C^1$ is independently chosen from -L-D and —O-L-D, at each occurrence, L is independently ($C_1$-$C_{10}$)hydrocarbylene, at each occurrence, D is independently chosen from —N(($C_1$-$C_5$)alkyl)$_3$ and a ($C_1$-$C_{10}$)alkyl-substituted cationic nitrogen-containing ($C_1$-$C_5$)heterocycle, and n is about 1 to about 100,000, and wherein contact between a therapeutically effective amount of the compound and a fungus including β-glucan that is at least partially masked from immune system detection is effective to at least partially unmask the β-glucan thereby increasing immunogenicity of the fungus.

BRIEF DESCRIPTION OF THE FIGURES

The drawings illustrate generally, by way of example, but not by way of limitation, various embodiments of the present invention.

FIG. 1A is a plot of the *C. albicans* yeast viability as a function of light exposure duration and antimicrobial concentration on a logarithmic scale for EO-OPE-DABCO (A) at 1 μg/ml (dashed lines) or 10 μg/ml (solid lines), in accordance with various embodiments.

FIG. 1B is a plot of the *C. albicans* yeast viability as a function of light exposure duration and antimicrobial concentration on a logarithmic scale for PPE-DABCO (B) at 1 μg/ml (dashed lines) or 10 μg/ml (solid lines), in accordance with various embodiments.

FIG. 2A is a fluorescence excitation spectrum for size fractionated β-glucan (low MW=11 kDa, medium MW=150 kDa) in the presence or absence of EO-OPE-DABCO, in accordance with various embodiments.

FIG. 2B is a fluorescence emission spectrum for size fractionated β-glucan (low MW=11 kDa, medium MW=150 kDa) in the presence or absence of EO-OPE-DABCO, in accordance with various embodiments.

FIG. 2C is a fluorescence excitation spectrum for size fractionated β-glucan (low MW=11 kDa, medium MW=150 kDa) in the presence or absence of PPE-OPE-DABCO, in accordance with various embodiments.

FIG. 2D is a fluorescence emission spectrum for size fractionated β-glucan (low MW=11 kDa, medium MW=150 kDa) in the presence or absence of PPE-OPE-DABCO, in accordance with various embodiments.

FIG. 3A is a fluorescence excitation spectrum for interactions between high molecular weight soluble β-glucan (MW=450 kDa) and EO-OPE-DABCO, in accordance with various embodiments. Dashed lines represent spectra of PE compounds alone, and solid lines represent the spectra observed in PE/glucan mixtures.

FIG. 3B is a fluorescence emission spectrum for interactions between high molecular weight soluble β-glucan (MW=450 kDa) and EO-OPE-DABCO, in accordance with various embodiments. Dashed lines represent spectra of PE compounds alone, and solid lines represent the spectra observed in PE/glucan mixtures.

FIG. 3C is a fluorescence excitation spectrum for interactions between high molecular weight soluble β-glucan (MW=450 kDa) and PPE-DABCO, in accordance with various embodiments. Dashed lines represent spectra of PE compounds alone, and solid lines represent the spectra observed in PE/glucan mixtures.

FIG. 3D is a fluorescence emission spectrum for interactions between high molecular weight soluble β-glucan (MW=450 kDa) and PPE-DABCO, in accordance with various embodiments. Dashed lines represent spectra of PE compounds alone, and solid lines represent the spectra observed in PE/glucan mixtures.

FIGS. 4A-4F are plots of the susceptibility of various *C. albicans* clinical isolates to 10 μg/mL EO-OPE-DABCO in the dark, in accordance with various embodiments. Lab strain SC5314 is shown for reference in all cases. Strains prefixed "TRL" are recent clinical isolates obtained as described herein.

FIG. 5 is a plot of the viability of *C. albicans, C. glabrata*, and *C. parapsilosis* in the presence of 10 μg/mL EO-OPE-DABCO in the dark, in accordance with various embodiments.

FIGS. 6A (transmitted light image) and 6B (reflected light image) are confocal microscopy images illustrating the presence of PPE-DABCO on the cell wall of *C. albicans* yeast cells using 405 nm excitation to generate fluorescence of bound PPE-DABCO, in accordance with various embodiments.

FIG. 7 is a plot of absolute B-glucan exposure of *C. albicans* following various treatments, in accordance with various embodiments. β-glucan exposure estimated from median fluorescence signal of AF 647.

FIGS. 8A-8B are plots of the strength of interactions of *C. albicans* yeast cells with HEK-293 cells, in accordance with various embodiments.

FIG. 9A is a plot of the yeast cell interaction with HEK 293 cells in the light but with no compound (negative control).

FIG. 9B is a plot of the upper left quadrant from FIG. 9A.

FIG. 9C is a plot of the upper right quadrant from FIG. 9A.

DETAILED DESCRIPTION OF THE INVENTION

Figure 2A:
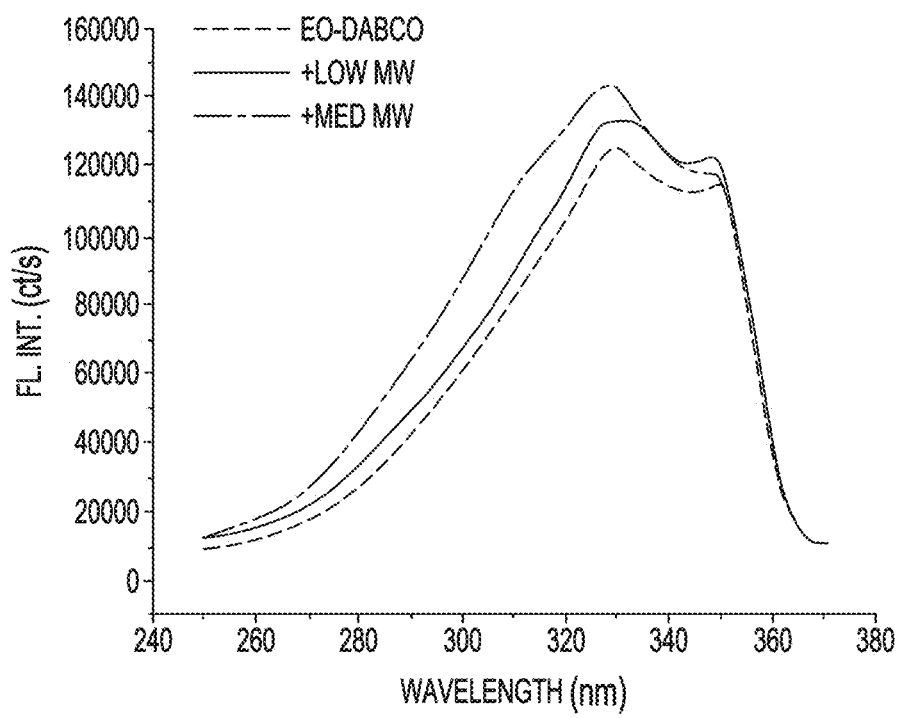
Figure 2B:
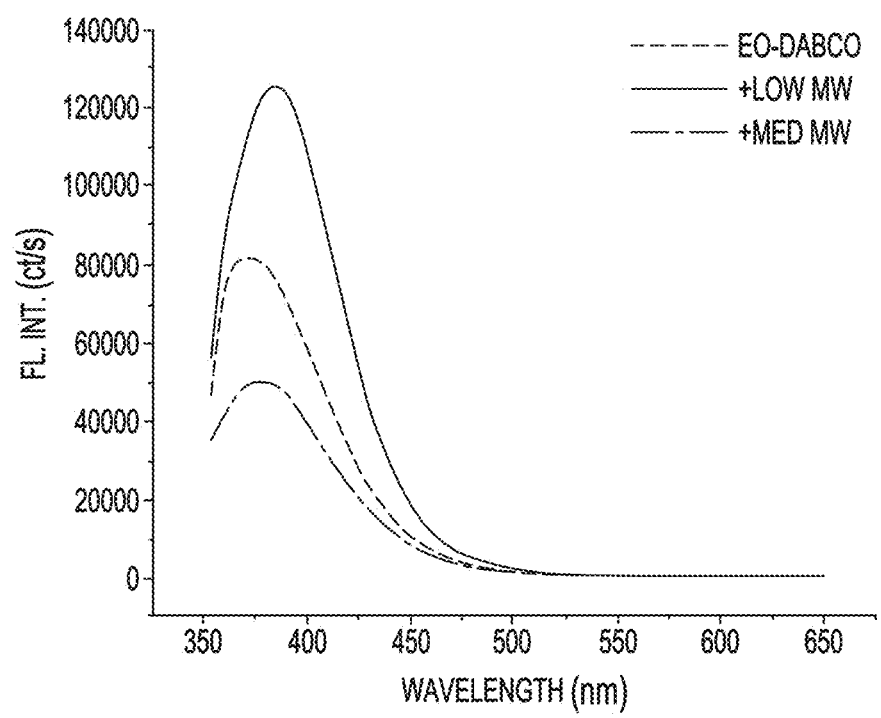
Figure 2C:
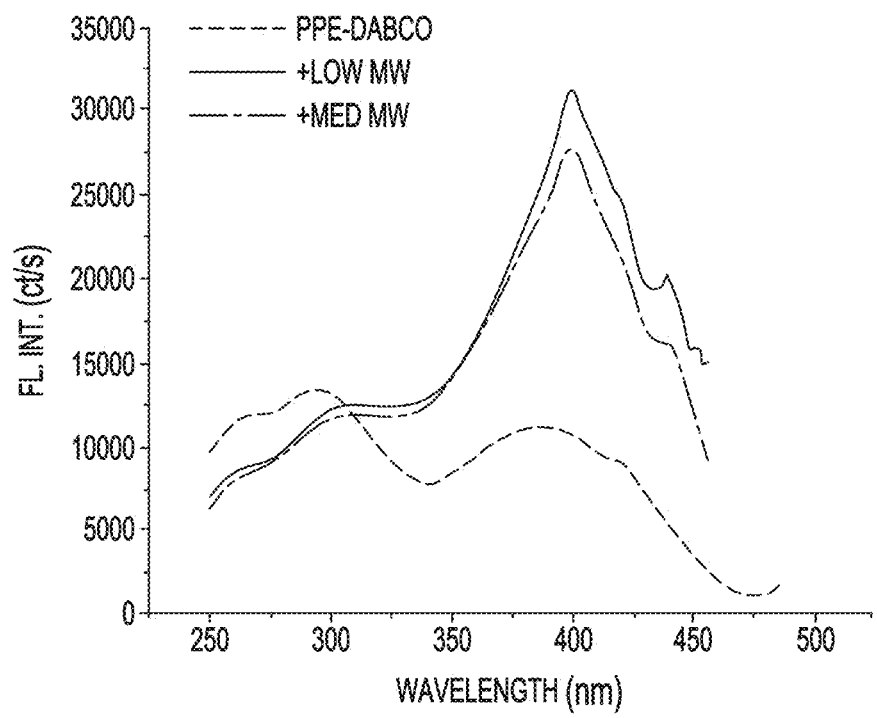
Figure 2D:
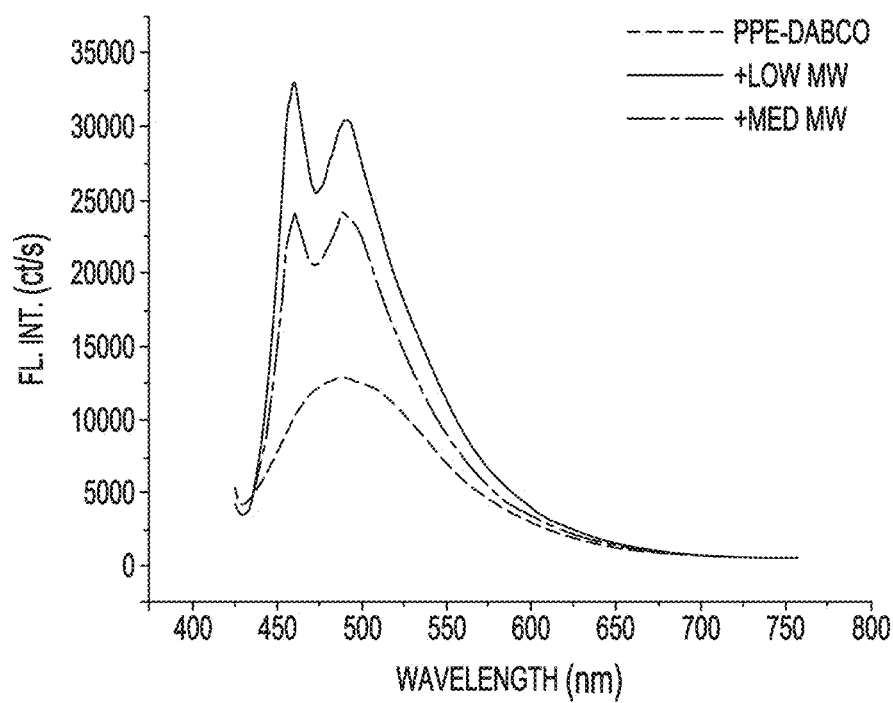
Figure 3A:
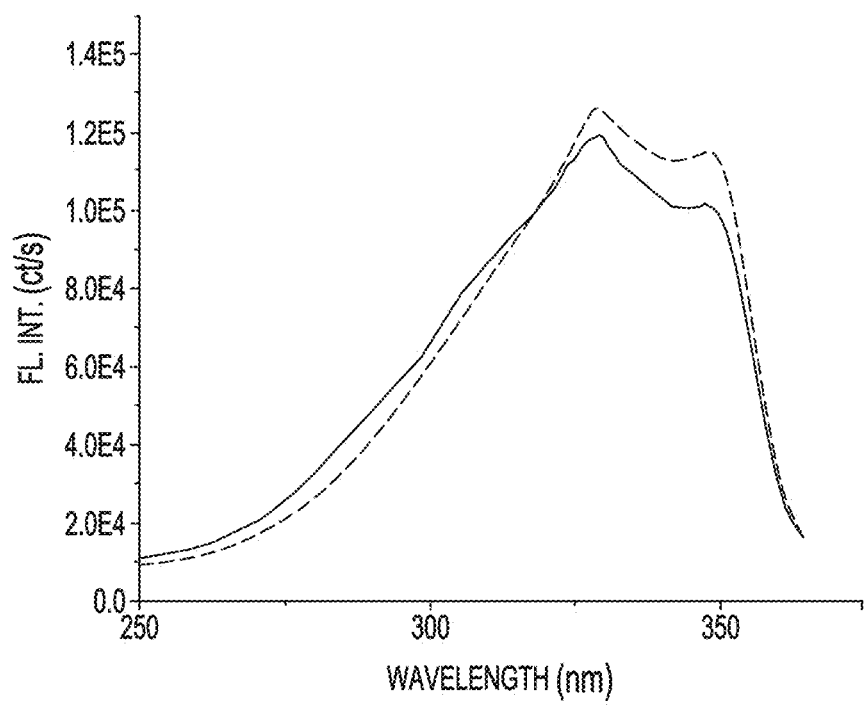
Figure 3B:
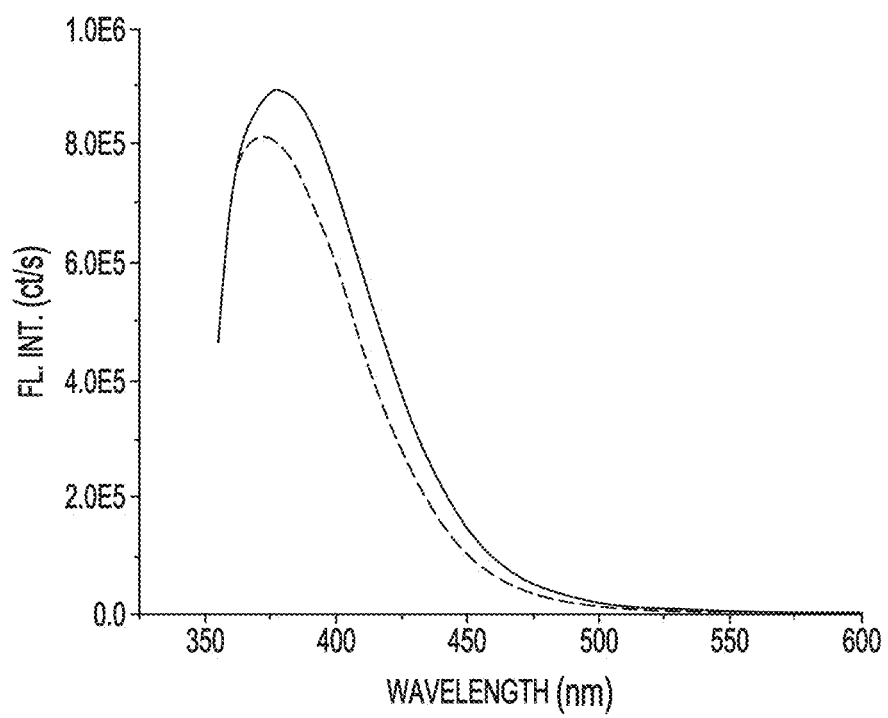
Figure 3C:
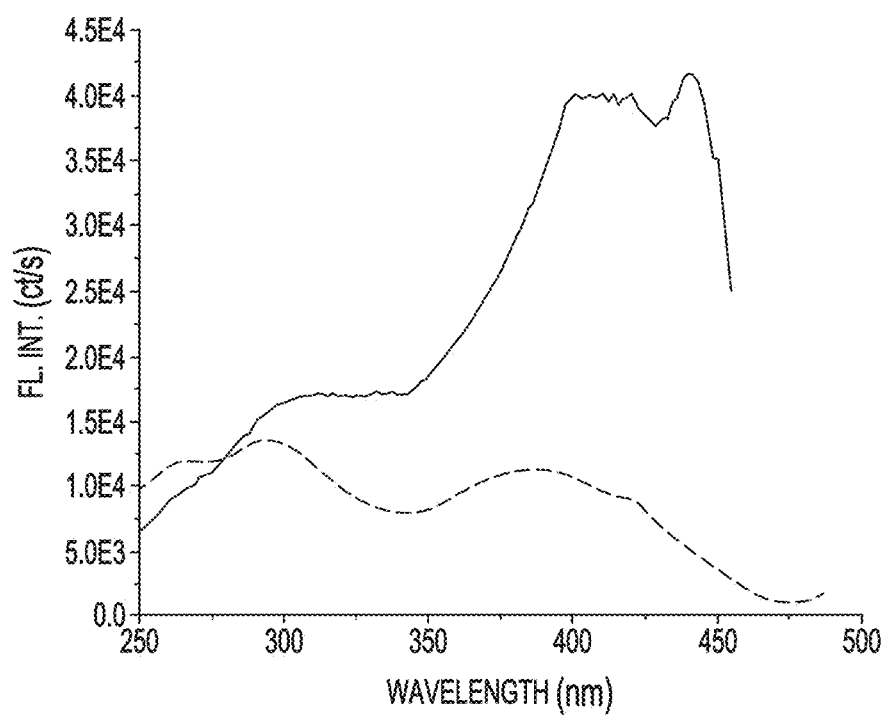
Figure 3D:
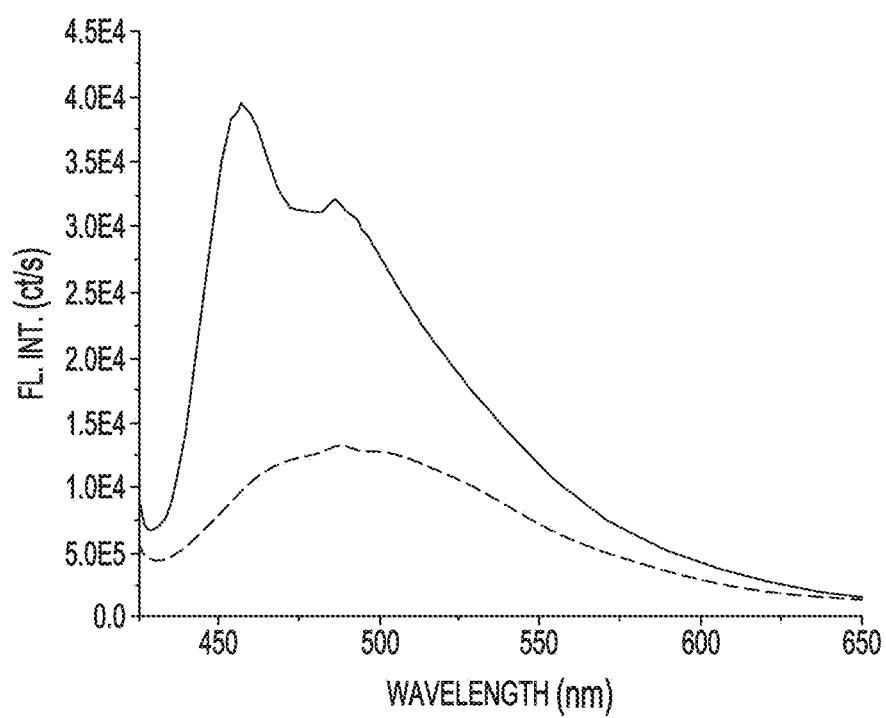
Figure 4A:
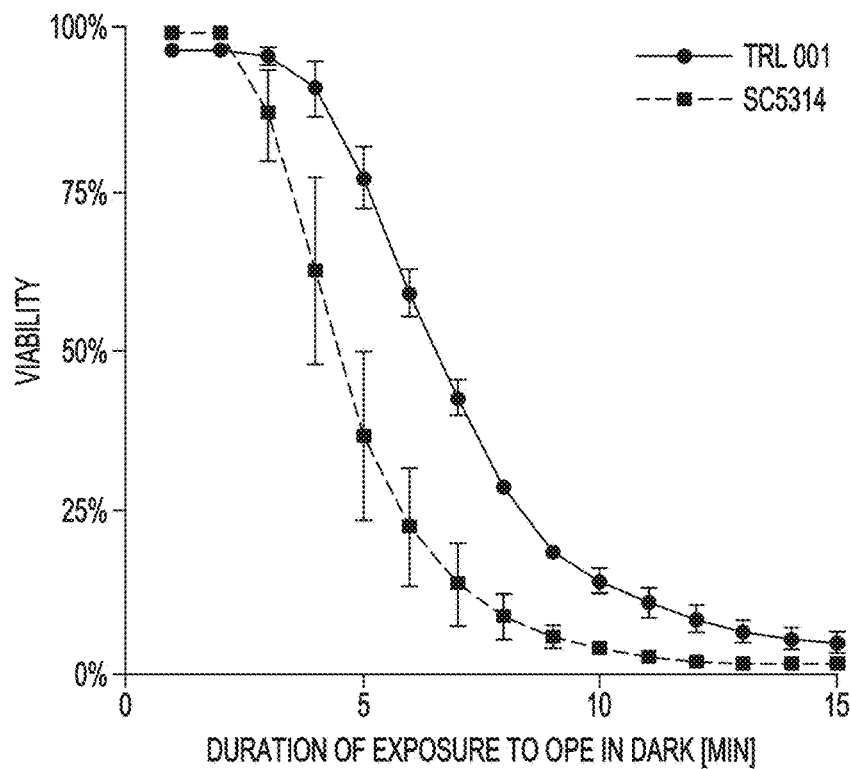
Figure 4B:
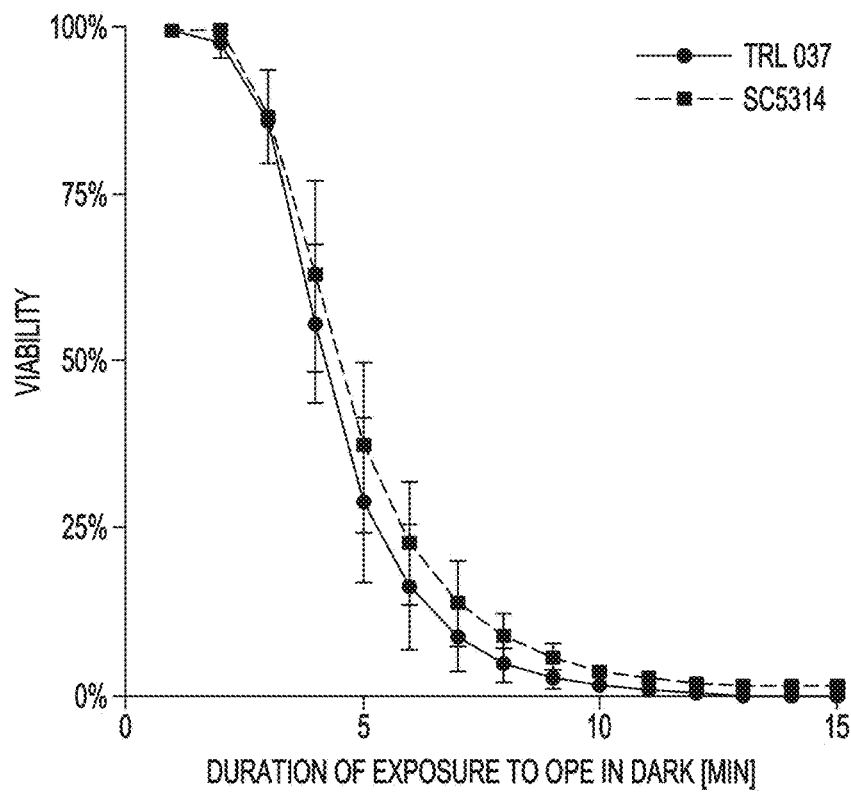
Figure 4C:
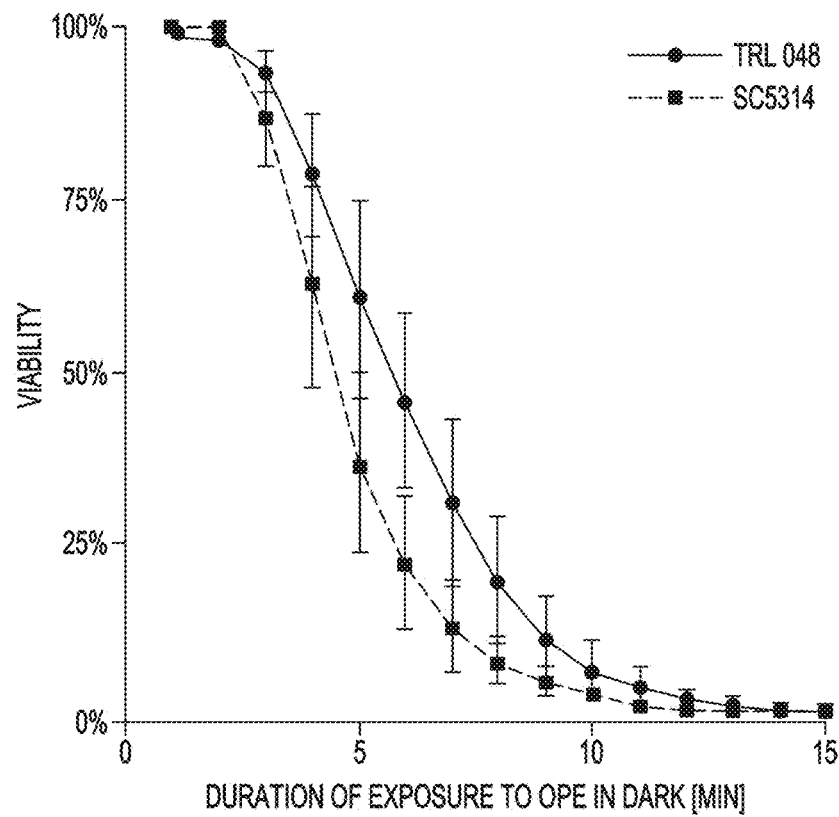
Figure 4D:
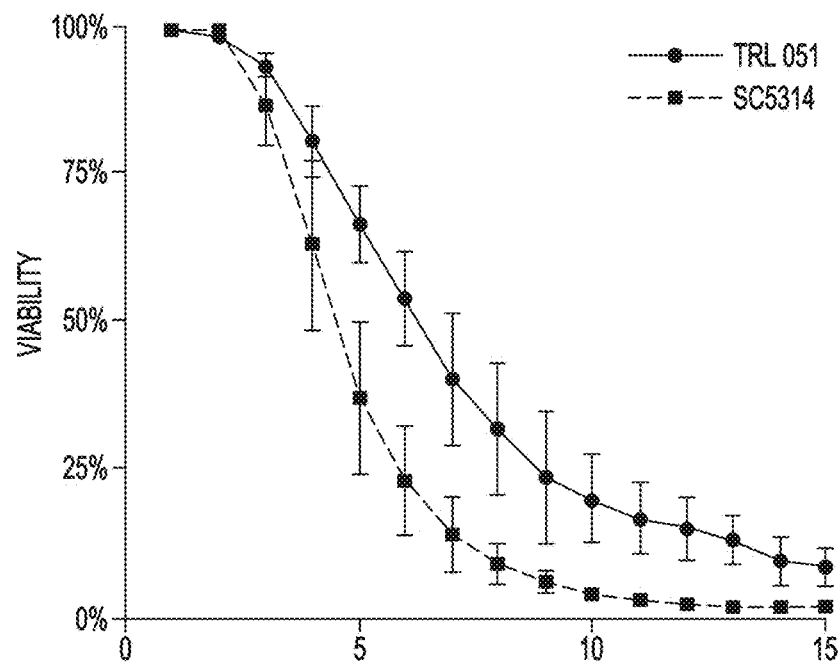
Figure 4E:
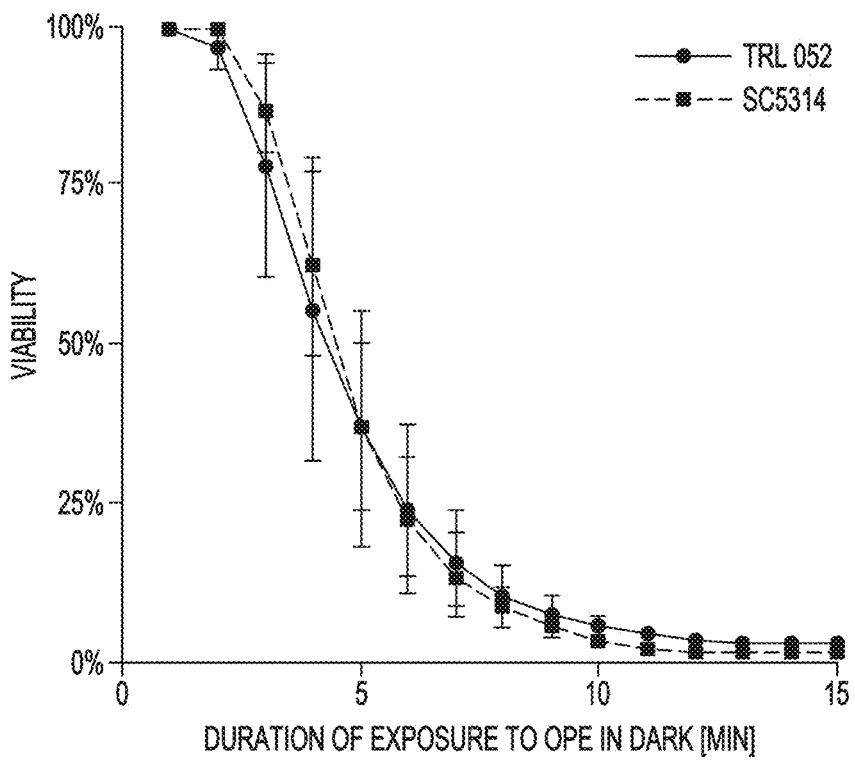
Figure 4F:
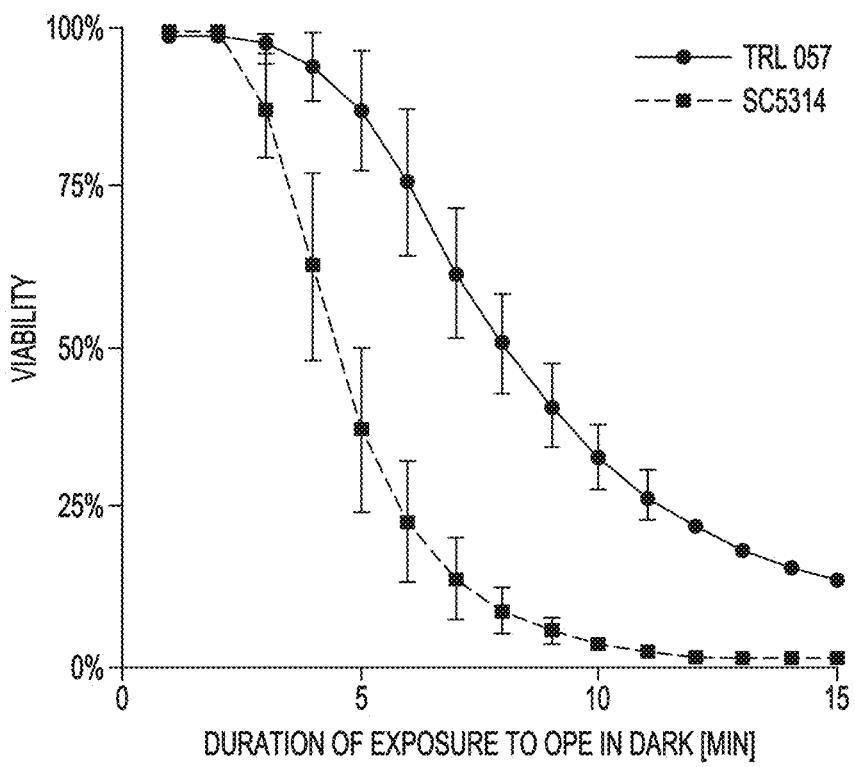

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O, (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O) CH$_2$C(O)R, C(S)R, C(O)OR, OC(O)R, C(O)N(R)$_2$, OC(O) N(R)$_2$, C(S)N(R)$_2$, (CH$_2$)$_{0-2}$N(R)C(O)R, (CH$_2$)$_{0-2}$N(R) N(R)$_2$, N(R)N(R)C(O)R, N(R)N(R)C(O)OR, N(R)N(R) CON(R)$_2$, N(R)SO$_2$R, N(R)SO$_2$N(R)$_2$, N(R)C(O)OR, N(R) C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heterocyclyl" as used herein refers to aromatic and non-aromatic ring compounds containing three or more ring members, of which one or more is a heteroatom such as, but not limited to, N, O, and S.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; RAH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

The term "number-average molecular weight" $(M_n)$ as used herein refers to the ordinary arithmetic mean of the molecular weight of individual molecules in a sample. It is defined as the total weight of all molecules in a sample divided by the total number of molecules in the sample. Experimentally, $M_n$ is determined by analyzing a sample divided into molecular weight fractions of species i having $n_i$ molecules of molecular weight $M_i$ through the formula $M_n = \Sigma M_i n_i / \Sigma n_i$. The $M_n$ can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The term "oligomer" as used herein refers to a molecule having an intermediate relative molecular mass, the structure of which essentially includes a small plurality of units derived, actually or conceptually, from molecules of lower relative molecular mass. A molecule having an intermediate relative mass can be a molecule that has properties that vary with the removal of one or a few of the units. The variation in the properties that results from the removal of the one of more units can be a significant variation.

The term "solvent" as used herein refers to a liquid that can dissolve a solid, liquid, or gas. Non-limiting examples of solvents are silicones, organic compounds, water, alcohols, ionic liquids, and supercritical fluids.

Herein, when it is designated that a variable in the structure can be "a bond," the variable can represent a direct bond between the two groups shown as linked to that variable, such as a single bond.

As used herein, the term "polymer" refers to a molecule having at least one repeating unit and can include copolymers.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

In various embodiments, the polymers described herein can terminate in any suitable way. The polymers can terminate with an end group that is independently chosen from a suitable polymerization initiator, —H, —OH, a substituted or unsubstituted ($C_1$-$C_{20}$)hydrocarbyl (e.g., ($C_1$-$C_{10}$)alkyl or ($C_6$-$C_{20}$)aryl) interrupted with 0, 1, 2, or 3 groups independently chosen from —O—, substituted or unsubstituted —NH—, and —S—, a poly(substituted or unsubstituted $C_{20}$)hydrocarbyloxy), and a poly(substituted or unsubstituted ($C_1$-$C_{20}$)hydrocarbylamino).

Cell Walls and Immunogenicity

*Candida* cell walls are built on a scaffold of β-(1,3;1,6)-glucan fibrils. β-glucan is highly immunogenic due to its recognition by Dectin-1 and beta2 integrins, leading to phagocytosis and inflammatory activation of innate immunocytes. *C. albicans* efficiently masks glucan from innate immune surveillance, which helps it to evade host defense. Conditions that can unmask glucan can increase Dectin-1 dependent responses (i.e., phagocytosis) to *Candida* yeasts by leukocytes. In various embodiments, the compounds described herein can therapeutically lead to glucan unmasking via chemical species that will increase immunogenicity of *Candida* species pathogens and provoke stronger innate immune response to fungal infection. In various embodiments, the methods described herein can induce glucan unmasking via ROS-mediated cell wall damage using phenylene ethynylene (PE) antimicrobials using small molecule drug compounds. Achieving therapeutic glucan unmasking can have clinical applications in care of all types of wounds and in preventing and/or treating microbial contamination of medical devices of many types.

In various embodiments, the methods described herein can treat Candidiasis and other fungal infections by changing the immunogenicity of the cell wall surface in *Candida* species. The cell wall can be an excellent target for therapeutic intervention in Candidiasis and other fungal infections because it has no human counterpart, so interventions impacting its synthesis, remodeling or repair are less likely to be confounded by off-target side effects. Also, relieving immune evasion via therapeutic glucan unmasking can bring existing host defense mechanisms maximally to bear on the eradication of the pathogen. In various embodiments, the methods described herein when used in combination with existing antimycotic drugs can increase the effectiveness and useful lifetime of first line azole and echinocandin drugs in the face of intrinsic and acquired resistance.

Therapeutic glucan unmasking can be important in the treatment of fungal infectious disease due to the potential breadth of its application to many common fungal pathogens. For example, emerging non-*albicans Candida* species pathogens, *Aspergillus* and *Histoplasma* species all engage in glucan masking. Moreover, β-glucan is ubiquitous in the cell walls of fungi, so it is a target of very broad significance to mycoses. In various embodiments, the methods described herein can be used to treat infections due to organisms that engage in glucan masking.

In various embodiments, the methods described herein provide therapeutic glucan unmasking in *Candida* species using light-activated antimicrobial agents. Phenylethynylenes (PEs) are antimicrobial agents with a high singlet oxygen yield upon light exposure. As shown in the Examples herein, in various embodiments, a polycationic PE (PPE-DABCO) can bind *Candida* cell walls, effecting light-activated glucan unmasking, and leading to increased phagocytosis. Other PE compounds can also be used to induce glucan exposure for the purpose of increasing the immunogenicity of the pathogen surface and elevating the host's immune response to the pathogen. In particular, PE compounds that include a thiophene moiety can induce glucan exposure. The method can increase the immunogenicity of any fungal pathogen that contains β-glucan in its cell wall, which is a common feature in fungal pathogens. Some major human fungal pathogen genera that can be susceptible to therapeutic glucan unmasking can include *Candida, Histoplasma*, and *Aspergillus*. PE-based glucan unmasking methods can have particular application to external medical settings such as wound care. In various embodiments, the methods described herein can be used to treat topical infections, for prevention or treatment of wound infections, for treatment applied to wound dressings, for treatments applied to treat or modify surfaces of medical devices that can become microbially or fungally contaminated, and to prevent or treat medical device infection.

In various embodiments, the methods described herein provide a general technique of using small molecule drug compounds to induce therapeutic glucan unmasking in *C. albicans*. Fungal enzymes synthesize and remodel cell wall structure, maintaining glucan masking. These enzymes are potential drug targets to induce therapeutic glucan unmasking. Drug design and/or drug screening approaches can be used to identify small molecule compounds that induce glucan unmasking in fungal pathogens such as *C. albicans* yeast.

Method of Treating a Fungal Infection.

In various embodiments, a method of treating a fungal infection is provided. The method includes contacting a fungus including a β-glucan that is at least partially masked from immune system detection with a therapeutically effective amount of a compound that at least partially unmasks the β-glucan to increase immunogenicity of the fungus. The method can include contacting the fungus with one or more compounds. The compound can be any suitable compound that can be used to carry out the method as described herein, and can be any compound described herein. In various embodiments, the compound is a polycationic conjugated aromatic system.

The contacting between the fungus and the compound can be any suitable contacting. The contacting can be contacting between the fungus and a solution including the compound. For example, the contacting can be contacting between a fungus in a catheter and a solution including the compound that has been injected into the catheter. The contacting can be contacting between the fungus and the surface of a substrate including the compound.

The therapeutically effective amount of the compound can be any suitable concentration, such as a concentration of about 0.001 mg/L to about 1000 g/L, or about 0.001 g/L to about 100 g/L, or about 0.001 mg/L or less, or less than, equal to, or greater than about 0.01 mg/L, 0.1 mg/L, 1 mg/L, 0.01 g/L, 0.1 g/L, 1 g/L, 10 g/L, 100 g/L, or about 1000 g/L, or more.

The β-glucan can be any suitable β-glucan, and can include β-(1,3)-glucan, β-(1,6)-glucan, β-(1,3;1,6)-glucan, or a combination thereof. The β-glucan can include β-(1,3; 1,6)-glucan, such as β-(1,3;1,6)-fibrils, such as in fungal cell walls.

The fungus can be any one or more fungi. The fungus can be a *Candida* species fungus, an *Aspergillus* species fungus, a *Histoplasma* species fungus, a *Blastomyces* species fungus, a *Coccidioides* species fungus, a *Cryptococcus* species fungus, a *Fusarium* species fungus, a *Sporothrix* species fungus, a *Rhizopus* species fungus, a *Mucor* species fungus, a *Rhizomucor* species fungus, a *Cunninghamella* species fungus, a *Absidia* species fungus, a *Saksenaea* species fungus, a *Apophysomyces* species fungus, a *Paracoccidioides* species fungus, a *Trichophyton* species fungus, a *Microsporum* species fungus, a *Epidermophyton* species fungus, or a *Malassezia* species fungus. The fungus can be *Candida albicans, Candida glabrata, Candida parapsilosis*, or a combination thereof. The fungus can include a biofilm (e.g., the fungus can be part of a biofilm). The fungus can be in or on an indwelling medical device (e.g., an implanted or inserted medical device, such as a medical implant or a catheter). The fungus can be in or on a catheter. The fungus can be in or on any medical device material. The fungus can be in or on any human tissue as a commensal or pathogenic organism.

The compound can include a unit having the structure:

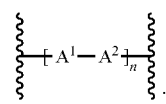

The variable $A^1$ can be chosen from a bond,

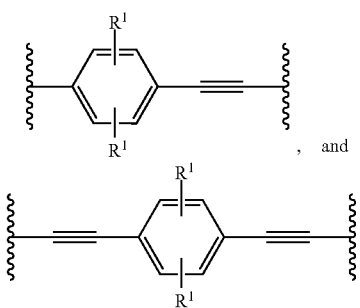

The variable $A^2$ can be chosen from a bond,

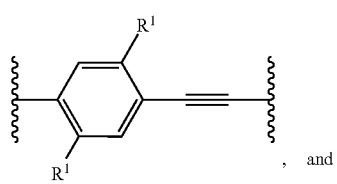

The variable $R^1$ can be chosen from —H and $C^1$. The compound can include at least one $C^1$ (e.g., at least one cationic group, or at least two cationic groups). At each occurrence, $C^1$ can be independently chosen from -L-D and —O-L-D. At each occurrence, L can be independently $(C_1-C_{10})$hydrocarbylene. At each occurrence, D can be independently chosen from $N((C_1-C_5)alkyl)_3$ and a $(C_1-C_{10})$ alkyl-substituted cationic nitrogen-containing $(C_1-C_5)$heterocycle. The variable n can be about 1 to about 100,000, about 1 to about 20, about 1 to about 10, or about 1, or less than, equal to, or greater than about 2, 3, 4, 5, 6, 7, 8, 9, 10, 11, 12, 13, 14, 15, 16, 17, 18, 19, or about 20 or more.

The compound can have the structure:

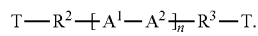

The variable $R^2$ can be chosen from a bond and

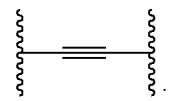

The variable $R^3$ can be chosen from a bond and

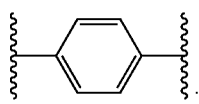 [SMILES: *c1ccc(*)cc1]

At each occurrence, the variable T can be independently chosen from —H, $C(O)$—O—$(C_1-C_{10})$alkyl, -phenyl, and —$R^1$.

The variable L can be independently chosen from methylene, ethylene, propylene, butylene, pentylene, and heptylene.

The variable $A^1$ can be chosen from a bond,

-continued

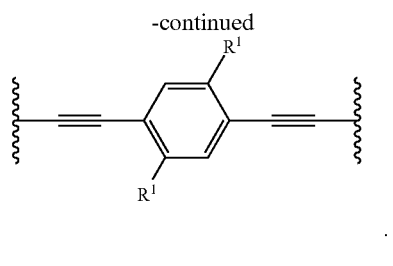

At each occurrence, the variable D can e independently chosen from —N(CH$_3$)$_3$,

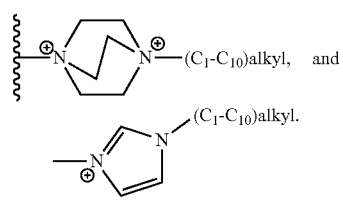

At each occurrence, the variable D can be independently chosen from —N(CH$_3$)$_3$,

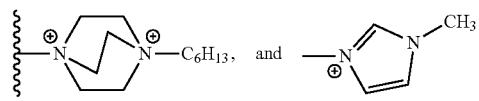

The variable C$^1$ can be chosen from:

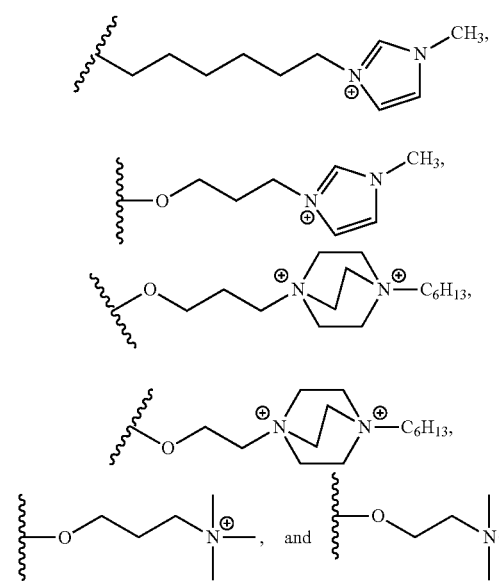

At each occurrence, the variable T can be independently chosen from —H, C(O)—O-ethyl, -phenyl, and —R$^1$.

The compound can be:

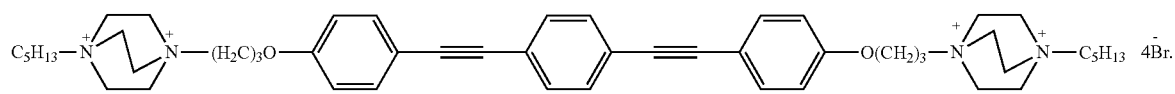

The compound can be a polymer (e.g., a polymer or copolymer) including the repeating unit:

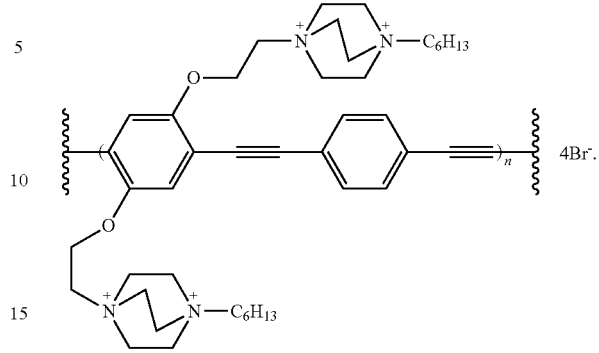

The compound can be a polymer (e.g., a homopolymer or copolymer) including the repeating unit:

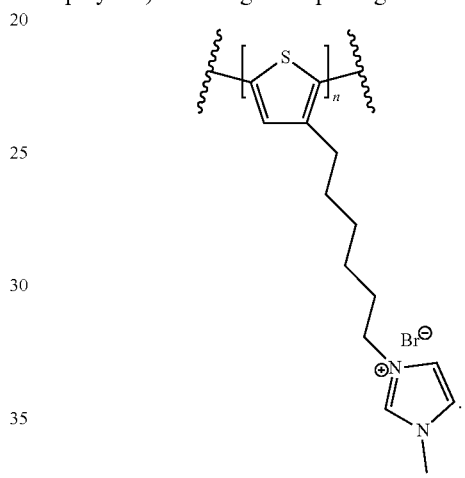

The compound can be a polymer (e.g., a homopolymer or copolymer) including the repeating group:

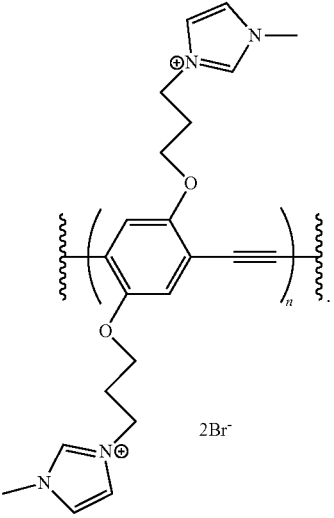

The compound can be a polymer (e.g., a homopolymer or copolymer) including the repeating group:
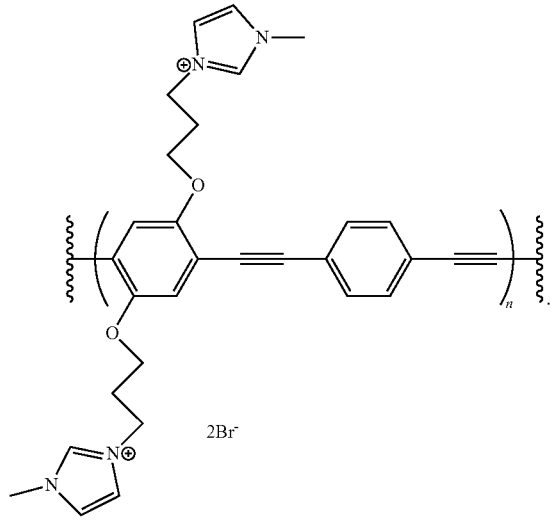
The compound can be a polymer (e.g., a homopolymer or copolymer) including the repeating group:
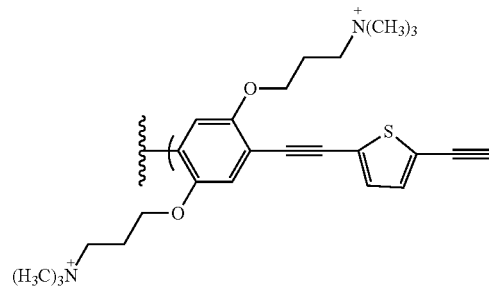
The compound can be:
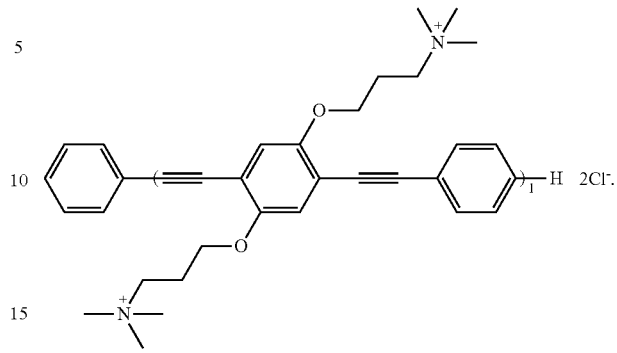
The compound can be:
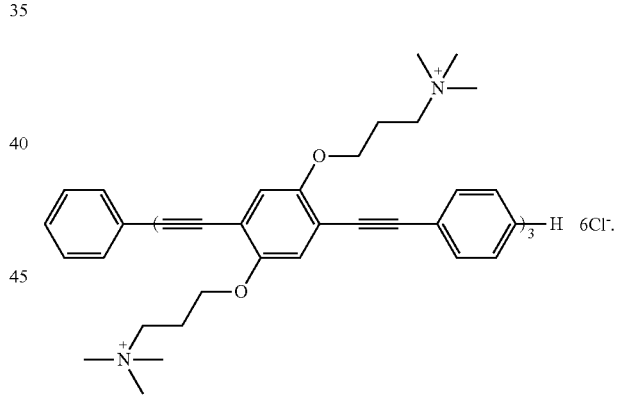
The compound can be:
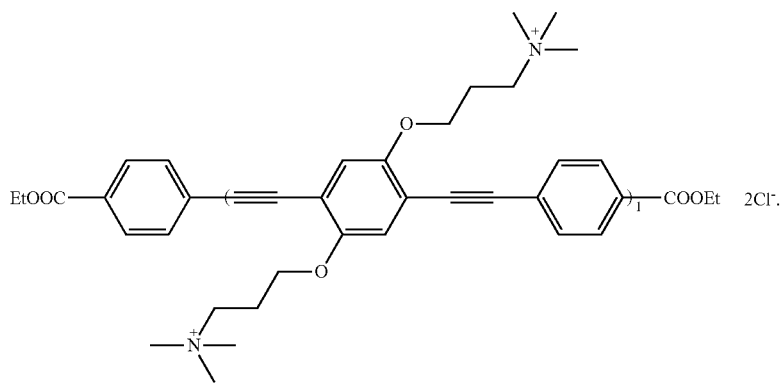 [SMILES: CCOC(=O)c1ccc(C#Cc2cc(OCCC[N+](C)(C)C)c(C#Cc3ccc(C(=O)OCC)cc3)cc2OCCC[N+](C)(C)C)cc1]

The compound can be:
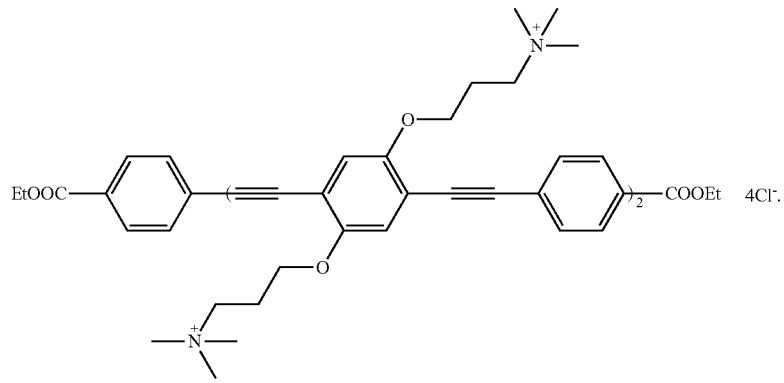
20
The compound can be:
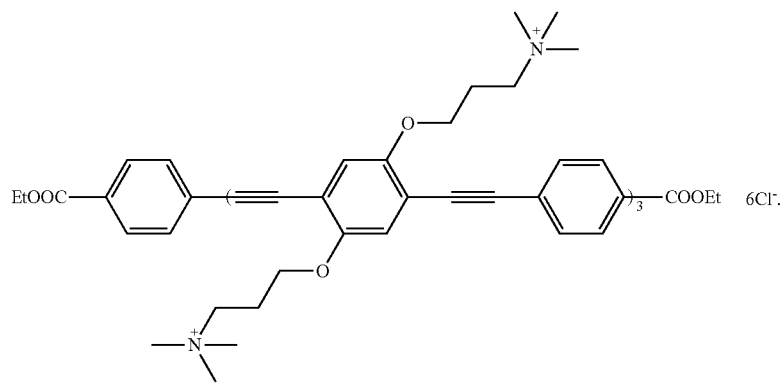
40
The compound can be:
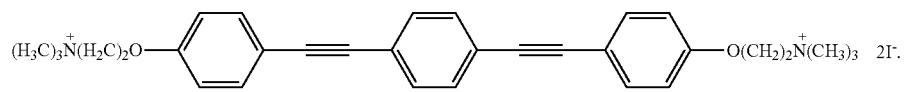
The compound can be:
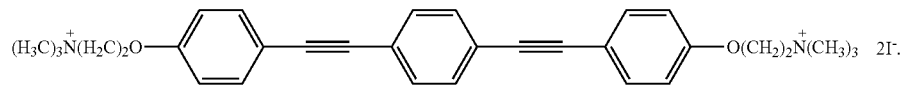
The compound can be:
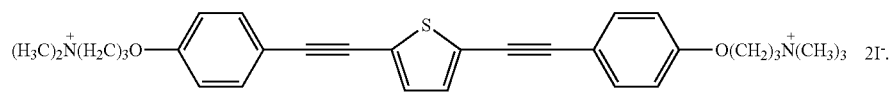

The compound can be:

$(H_3C)_3\overset{+}{N}(H_2C)_2O$—⟨phenyl⟩—≡—⟨thiophene-S⟩—≡—⟨phenyl⟩—$O(CH_2)_2\overset{+}{N}(CH_3)_3$  2I⁻.

Method of Preventing or Reducing a Fungal Injection on a Substrate.

In various embodiments, the method described herein can prevent or reduce a fungal infection on a substrate. The method can include treating the substrate with a therapeutically effective amount of a compound so that contact between the treated surface and a fungus including β-glucan that is at least partially masked from immune system detection is effective to at least partially unmask the β-glucan thereby increasing immunogenicity of the fungus and preventing or reducing fungal infection on the substrate from the fungus. At the time of treatment, the substrate can be substantially free of the fungus, or the substrate can include the fungus. The compound can be any suitable compound, such as any compound described herein.

The method can include filling or coating a medical device, such as a catheter, with a solution including the compound.

Method of Preventing or Reducing a Fungal Infection on or in a Device.

In various embodiments, the method of preventing or reducing a fungal infection on or in a device. The device can be any device, such as a medical device, such as a catheter. The method can include treating the device with a therapeutically effective amount of a compound so that contact between the compound and a fungus including β-glucan that is at least partially masked from immune system detection is effective to at least partially unmask the β-glucan thereby increasing immunogenicity of the fungus and preventing or reducing fungal infection on or in the device from the fungus. The compound can be any suitable compound, such as any compound described herein.

The method can include filling or coating a medical device, such as a catheter, with a solution including the compound.

Antifungal Compound.

In various embodiments, any one of the compounds described herein is an antifungal compound. Contact between a fungus including a β-glucan that is at least partially masked from immune system detection and a therapeutically effective amount of the antifungal compound can at least partially unmasks the β-glucan to increase immunogenicity of the fungus. The compound can be any suitable compound that can be used to perform the methods described herein. The compound can be any suitable compound described herein.

Various embodiments provide a device (e.g., a medical device) or a substrate that includes one or more of the compounds, wherein the device experiences less or no fungal infections, as compared to a device or substrate free of the one or more compounds.

The antifungal compound can include a unit having the structure:

$$\{\!\!\{-\!\!+\!\!A^1\!-\!A^2\!\!\}_n\!\!\}\!\!\}.$$

The variable $A^1$ can be chosen from a bond,

⟨phenyl with $R^1$⟩—≡—, and

—≡—⟨phenyl with $R^1$⟩—≡—.

The variable $A^2$ can be chosen from a bond,

⟨phenyl⟩, ⟨thiophene with S⟩, and

⟨thiophene with $R^1$⟩—≡—.

The variable $R^1$ can be chosen from —H and $C^1$. The compound can include at least one $C^1$. At each occurrence, $C^1$ can be independently chosen from -L-D and —O-L-D. At each occurrence, L can be independently $(C_1-C_{10})$hydrocarbylene. At each occurrence, D can be independently chosen from —N$((C_1-C_5)$alkyl$)_3$ and a $(C_1-C_{10})$alkyl-substituted cationic nitrogen-containing $(C_1-C_5)$heterocycle. The variable n can be about 1 to about 100,000. Contact between the compound and a fungus including β-glucan that is at least partially masked from immune system detection is effective to at least partially unmask the β-glucan thereby increasing immunogenicity of the fungus.

The compound can have the structure:

$$T-R^2-\!\!+\!\!A^1\!-\!A^2\!\!\}_n\!\!-R^3-T.$$

The variable $R^2$ can be chosen from a bond and

—≡—.

The variable $R^3$ can be chosen from a bond and

⟨phenyl⟩.

At each occurrence, T can be independently chosen from —H, C(O)—O—$(C_1-C_{10})$alkyl, -phenyl, and —$R^1$.

The compound can be or include any of the compounds shown in Table 1.

TABLE 1

Antifungal compounds.

| | |
|---|---|
| EO-OPE-1(DABCO) | C₈H₁₃–N⁺(DABCO)N⁺–(H₂C)₃O–[phenyl]–≡–[phenyl]–≡–[phenyl]–O(CH₂)₃–N⁺(DABCO)N⁺–C₈H₁₃    4Br⁻ |
| PPE-DABCO | Poly[phenylene ethynylene] with bis(DABCO-C₆H₁₃) side chains via –O–CH₂CH₂–N⁺(DABCO)N⁺–C₆H₁₃; 4Br⁻ |
| P3HT-imidazolium | Poly(3-hexylthiophene) bearing pendant alkyl-imidazolium (N-methyl); Br⁻ |
| PIM-4 | Poly(phenylene ethynylene) with two –O(CH₂)₃–(N-methylimidazolium) side chains per repeat unit; 2 Br⁻ |

TABLE 1-continued
Antifungal compounds.
PIM-2
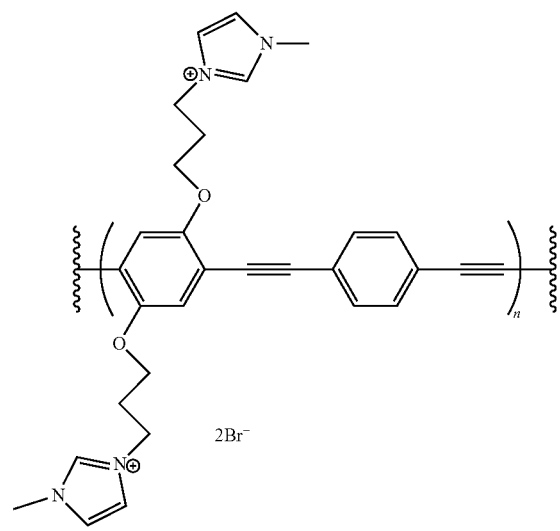
PPE-Th
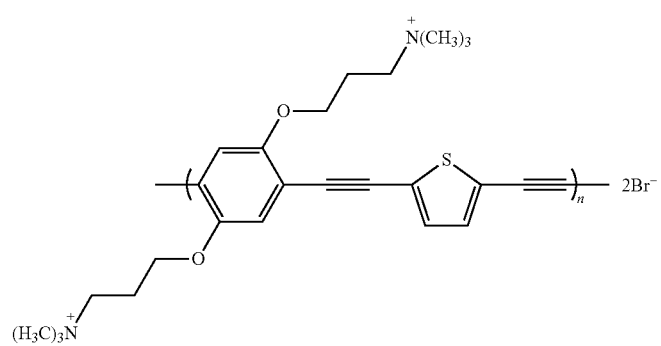
S-OPE-1(H)
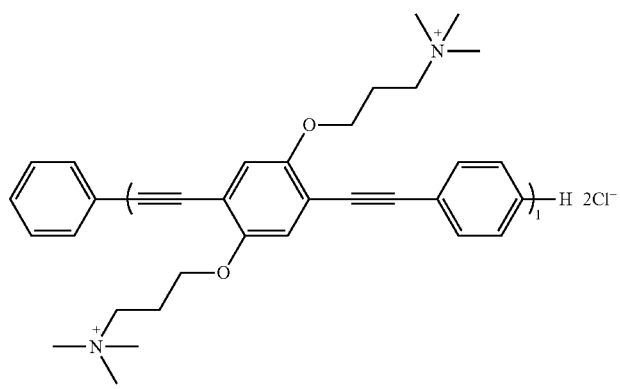

TABLE 1-continued
Antifungal compounds.
S-OPE-2(H)
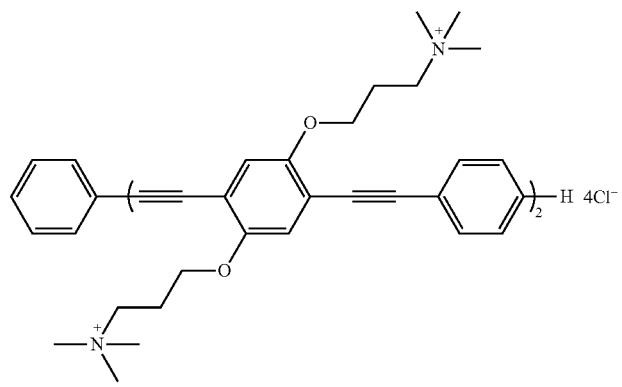
S-OPE-3(H)
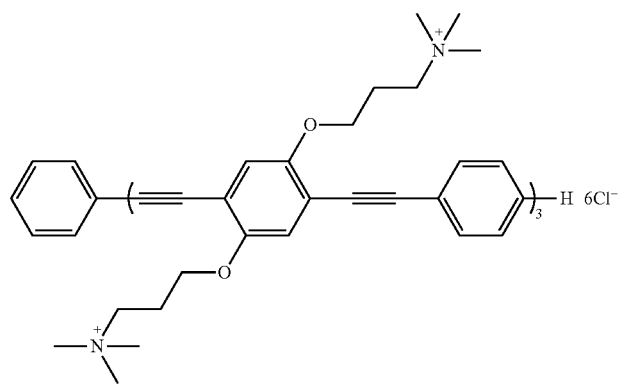
S-OPE-1(COOEt)
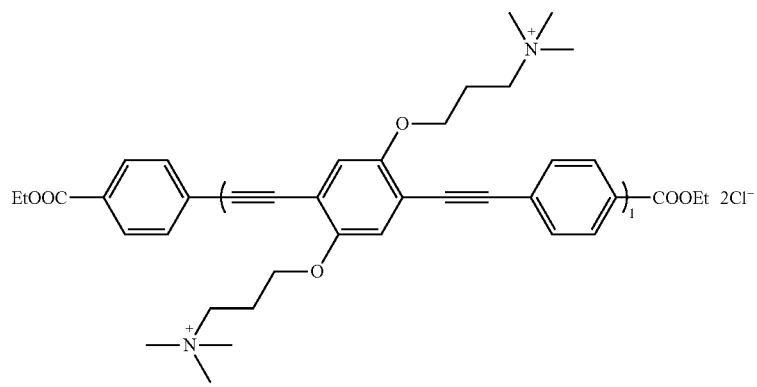
S-OPE-2(COOEt)
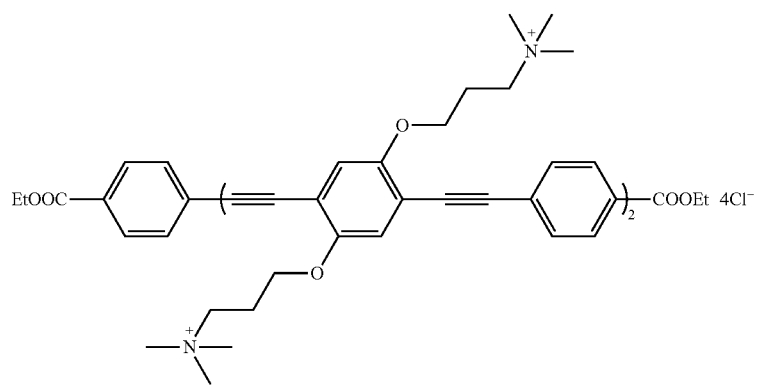

TABLE 1-continued

Antifungal compounds.

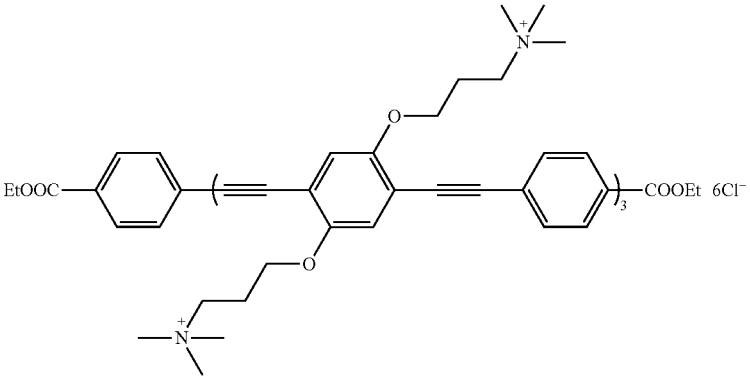

S-OPE-3(COOEt)

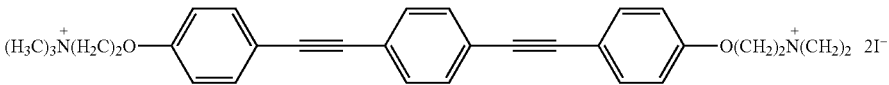

EO-OPE-1(C3)

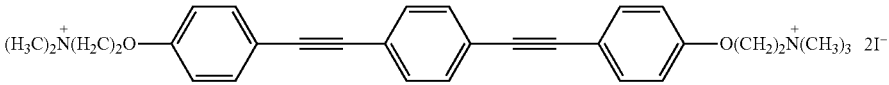

EO-OPE-1(C2)

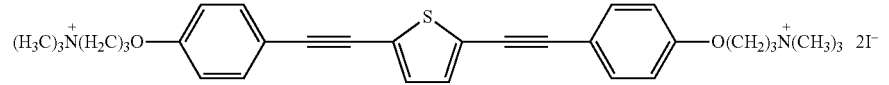

EO-OPE-1(Th)

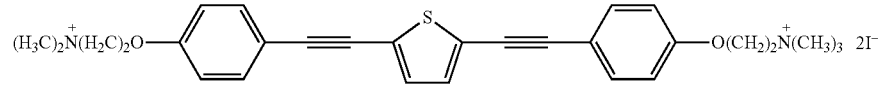

EO-OPE-1(Th, C2)

EXAMPLES

Various embodiments of the present invention can be better understood by reference to the following Examples which are offered by way of illustration. The present invention is not limited to the Examples given herein. In the Examples herein, references to "glucan" refer to β-glucan.

General

The antimicrobial effectiveness of two phenylene ethynylene (PE) compounds against *Candida* species. A subset of conjugated polyelectrolytes, phenylene ethynylenes have shown promising biocidal activity against Gram-positive and -negative bacterial pathogens, as well as the environmental yeast, *Saccharomyces cerevisiae*. The chemical structure of these compounds renders them capable of inducing broad-spectrum cell damage. The phenylene ethynylenes studied include compounds with alternating phenyl and acetylenic groups with appended cationic groups (Scheme 1). The interaction of the cationic quaternary ammonium groups with net-anionic membranes and cell walls facilitates interactions with cells, leading to extensive leakage of cell contents. In addition, when PE compounds such as these are irradiated by the appropriate wavelength of light, the backbone produces reactive oxygen species (ROS) that induce rapid cell death.

Scheme 1. Molecular structures of ologomeric EO-OPE-DABCO (top) and polymeric PPE-DABCO (bottom).

EO-OPE-DABCO

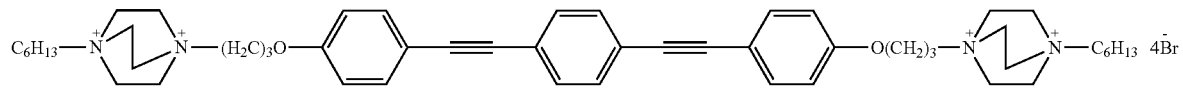

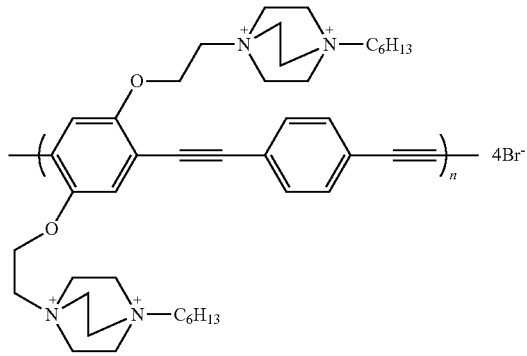

PPE-DABCO

The oligomeric and polymeric molecular size of PE compounds can play a role in their mechanisms of killing. Additionally, the antimicrobial activity of these compounds can dependent on various factors that include molecular conformation, size, functional groups, and, the membrane composition of the target pathogen. After treatment with the compounds, the viability of Candida spp. was monitored using flow cytometry.

Materials & Methods

1. Fungal Culture

Candida albicans (ATCC, # MYA-2876), C. parapsilosis (ATCC, #22019), and C. glabrata (ATCC, #2001) were grown from glycerol stocks, stored at −80° C. Said stock was transferred to 5 mL filtered yeast extract-peptone-dextrose (YPD) medium (Becton Dickinson), and grown for 16 h at 30° C., with a shaking speed of 300 RPM. These growth conditions yielded yeast at the mid exponential phase.

Following a 10 minute centrifugation at 4,400 RPM, the supernatant was replaced with sterile phosphate-buffered saline (PBS), and subsequently vortexed. This washing step is repeated a second time to mitigate cell debris. Cell concentration was then determined using a disposable hemocytometer (INCYTO C-Chip; Fisher Scientific).

2. Derivation of Clinical Isolate Strains of C. albicans

Patient specimens (peripheral blood or catheter tips) were processed by Tricore Reference Laboratories (Albuquerque, N. Mex.) and identified as C. albicans using a Bruker Biotyper MALDI-TOF system (MS ID score >2.0). Clonal isolates so identified were subcultured on Sabouraud agar slants and provided to the investigators as unique strains. Isolate strains were provided in completely deidentified form according to procedures approved by the University of New Mexico School of Medicine Human Research Protections Office. For biocidal assays, clinical isolates were grown in YPD broth as described above.

3. Biocidal Testing

Biocidal experiments were carried out in either translucent or opaque 1.5 mL microcentrifuge tubes, at cell concentrations of $5 \times 10^6$/mL. EO-OPE-DABCO and PPE-DABCO stocks were prepared in sterile deionized water (18.2 MΩ·cm at 25° C.), and contained 0.47% dimethyl sulfoxide (by volume) to improve solubility and minimize aggregate formation. Negative controls contained equal amounts of dimethyl sulfoxide.

Samples were exposed to controlled amounts of light using a 14-lamp photoreactor (LZC-4V; Luzchem Research; Ottawa, Ontario). A rotating carousel ensured that all samples receive equivalent levels of light exposure; ventilation kept the photoreactor below 30° C. EO-OPE-DABCO absorbs in the ultraviolet region, warranting the use of UVA lamps (350 nm emission peak; 4.46±2.41 mW/cm$^2$) to optimize singlet oxygen yields. Conversely, 420 nm blue-light lamps (6.62±2.93 mW/cm$^2$) were used in PPE-DABCO tests; unlike its oligomeric counterpart, polymeric PPE-DABCO absorbs in the near-visible range. Power density output was measured at the peak excitation wavelength for both lighting configurations. Data shown is an aggregation of two independent replicate experiments.

Samples were then stained with 5 μM membrane-permeable SYTO 9 and 1 μM membrane-impermeable TO-PRO-3, both of which are nucleic acid stains. After 30 min, samples were evaluated by flow cytometry (FACSCalibur; Becton Dickinson). At least 10,000 events were evaluated in each trial. A heat-killed sample (70° C. for 30 min) was used to identify the fluorescence characteristics of dead cells.

15 min dark-activity assays were carried out in a somewhat different manner. Samples were prepared and stained with SYTO 9 and TO-PRO-3, albeit in the absence of any biocide. After a 30 min staining duration, EO-OPE-DABCO was added (10 μg/mL final concentration); the sample was then vortexed and analyzed by flow cytometry. Every minute, viability data was collected (again, 10,000 events/sample), for a total of 15 minutes. EO-OPE-DABCO was added one sample at a time, so that, in each case, flow cytometry readings could begin within 1 min of the biocide's introduction.

4. Spectroscopy of β-Glucan Interactions

Stocks of S. cerevisiae β-(1,3)-glucan (high, medium or low MW; gift of Biothera, Eagan, Minn.), PPE-DABCO, and EO-OPE-DABCO were mixed with 10 mM pH 7.4 phosphate buffer to a final concentration of 2 μg/mL in PPE-DABCO or EO-OPE-DABCO and 100 μg/mL in glucan. 200 μL solutions were transferred to a 160 μL nominal volume fused quartz fluorimetry cuvette, and read on a PTI QuantaMax 40 steady-state fluorescence spectrophotometer (HORIBA Scientific, Edison, N.J.) with PMT detection. Emission spectra were obtained using an excitation wavelength of 350 nm for EO-OPE-DABCO and 420 nm for PPE-DABCO, and excitation spectra were obtained with the corresponding maximum emission wavelength.

5. Surface Exposure of β-Glucan

C. albicans yeast cells were treated in a similar manner to that of the previously described biocidal experiments. In effort to maintain a consistent degree of cell death across samples, OPE-DABCO exposure in UVA light was limited to just 10 min. A thermal positive control was also implemented, which entailed heating samples to 100° C. for 30 min. Following the appropriate treatment and removal from the photoreactor, samples were blocked with 1% (w/v) bovine serum albumin (BSA) for 30 min at room temperature. The samples were then treated with a primary antibody, anti β-glucan IgG, at a final concentration of 10 µg/mL, for an additional 30 min. Negative controls contained 10 µg/mL isotype-matched murine IgG in place of anti β-glucan IgG. A secondary antibody with Alexa Fluor 647 dye was then added (1 ug/ml in PBS+1% BSA), along with 5 µM SYTO 9 were simultaneously added and allowed to stain cells for 30 minutes at 25° C. prior to analysis by flow cytometry. Data shown is an aggregation of two independent replicate experiments.

6. Tissue Culture & Transfection

HEK-293 cells (ATCC, # CRL-1573) were cultured in DMEM supplemented with 10% CS, 1% Penicillin/Streptomycin, 2 mM L-glutamine, and 1 mM sodium pyruvate at 37° C., 5% $CO_2$. Cells were then plated in 6 well plate at $1 \times 10^5$ cell per well. mApple-human Dectin1A-C-10 (addgene, #54883) was transfected into cells by following standard protocols using Fugene 6 (Promega, # E2691). Cell cultures were used for further experimentation at 24 h post-transfection with growth in normal medium, as described above.

7. Phagocytosis Assay

C. albicans yeast cells were subjected to the same treatment conditions as in the aforementioned β-glucan exposure study, before being spun down and washed in PBS. Following the last wash step the C. albicans were stained with 7.5 µM of SYTO 9 (Invitrogen, # S-34854) and 7.5 µM of CypHer5E NHS-ester (GE Healthcare, # PA15401) for one hour at 25° C. After staining the C. albicans were added to live, Dectin-1A-C-10 transfected HEK-293 cells for one hour. Next ice cold PBS was used to lift the HEK-293 cells off of the plate. Either controls with C. albicans or HEK-293 alone or the above samples with a mixture of C. albicans and HEK-293 cells were analyzed using an LSR Fortessa flow cytometer (Becton Dickinson) and FlowJo software (FlowJo, Ashland, Oreg.). At least 10,000 side scatter (SSC)-positive events are evaluated in each trial. CypHer 5, SYTO 9, and mApple fluorescence was observed at emission wavelengths of 660 nm (670/14), 525 nm (505 LP, 530/30), and 578 nm (582/15), respectively. Data shown is an aggregation of two independent replicate experiments.

8. Results

A series of biocidal studies were carried out to gain insight to the light-activated effects of EO-OPE-DABCO and PPE-DABCO on *Candida* species pathogens. Phenylene ethynylenes are unique in that their mechanism of action differs, depending on the presence of light; in particular, light intensity, emission wavelength, and duration. In the studies described herein, duration of light exposure was the primary variable being studied. Light intensity was kept constant using a photoreactor with 14 interchangeable lamps. Lamps were chosen to have an emission wavelength overlapping the excitation spectrum of the phenylene ethynylene being used. 350 nm-centered INA lamps were implemented for EO-OPE-DABCO testing, while 420 nm-centered lamps were used in PPE-DABCO tests. With light intensity and spectrum being held constant for a given phenylene ethynylene, the effect of light exposure duration was investigated to discern *C. albicans*' susceptibility to phenylene ethynylenes in the light vs. dark. Even though all samples were exposed to one of the two compounds for a total of 60 min, the duration of light exposure was varied by 4 min intervals and the balance of 60 min exposure was in the dark.

FIG. 1A illustrates the biocidal activity of the two concentrations of EO-OPE-DABCO: 1 and 10 µg/mL. In the absence of light, a 1 µg/mL concentration of EO-OPE-DABCO killed 34% of *C. albicans* yeast cells; however, killing drastically increased with just minimal light exposure, as 2 log cell death was observed after just 8 min. Increasing the concentration to 10 ug/mL greatly improved the dark killing capacity of the EO-OPE-DABCO, resulting in 97% cell death. With minimal light exposure, 10 µg/mL EO-OPE-DABCO exhibited a profound biocidal effect, exceeding 3 log reduction after just 4 min in UVA light. Both EO-OPE-DABCO concentrations exceeded 3 log kill (over 99.9% cell death) after 20 min of light exposure, and 4 log reduction (99.99% cell death) is nearly achieved after 60 min of light exposure. Interestingly enough, lowering the concentration of EO-OPE-DABCO to just 1 µg/mL had little effect on light-activated biocidal activity, but a far larger effect on dark killing. Some level of photodegradation was notable by 60 min (data not shown), which is why testing durations were limited to 1 h, as photodegradation limits $^1O_2$ generation.

FIG. 1B illustrates the viability of *C. albicans* following exposure to PPE-DABCO. It is quite evident that, unlike EO-OPE-DABCO, its PPE-DABCO counterpart is non-toxic in the absence of light; even at a relatively high concentration of 10 µg/mL, little-to-no cell death was observed even after 8 min of exposure to 420 nm light, A 2 log reduction of *C. albicans* viability was observed after 48 min of light exposure. After 52 min of continuous light exposure, 10 µg/mL PPE-DABCO was able to kill 99% of all *C. albicans* yeast cells. In summary, dark killing of the EO-OPE-DABCO is concentration-dependent, while the light activity is not. Conversely, the PPE-DABCO's dark killing was not dependent on concentration, since it failed to elicit membrane damage in that case. Biocidal activity of PPE-DABCO is predicated on light exposure.

Interactions between both PEs with soluble β-(1,3)-glucan extracted from *Saccharomyces cerevisiae* yeast cell walls were evaluated. The structure of *S. cerevisiae* and *C. albicans* β(1.3)-glucan is similar, and this polysaccharide is an important part of *Candida* drug resistance and pathogenicity, amounting to 40% of the cell wall. Size fractionated β-glucan (low MW=11 kDa, medium MW=150 kDa, high MW=450 kDa) were tested (FIGS. 2A-2D). Excitation and emission spectra of EO-OPE-DABCO and PPE-DABCO were evaluated in the absence or presence of the soluble β-glucan, as shown in FIGS. 3A-3D.

Although more profound in the case of PPE-DABCO, enhanced emission of both PEs upon the introduction of the high molecular weight β-glucan was observed, which is indicative of complexation. In addition, a small degree of red-shifting was observed, suggesting that rotation of the conjugated regions of the PEs are restricted due to complexation with soluble β-glucan. Lateral hydrogen bonding between β-glucan polymers can facilitate PE/β-glucan complexation, analogous to their role in stabilizing lateral interactions of individual β-glucan polymers in aqueous solution. These observed photophysical changes were more dramatic with PPE-DABCO than EO-OPE-DABCO, suggesting that increased complexation of PPE-DABCO can be due to its size, which is substantial relative to that of an oligomeric molecule. PPE-DABCO has numerous sites where weak interactions with glucan polymers may form; furthermore, extensive valency of laterally-aggregated β-glucan would make this interaction very strong. EO-OPE-DABCO is far smaller than PPE-DABCO, and therefore exhibits a lower-avidity interaction with β-glucan. Without being bound by theory, these results can help explain PPE's inability to kill *C. albicans* in the dark. Exhibiting a strong propensity to interact and associate with β-glucan, it is likely that PPE-DABCO is limited in its ability to fully penetrate the cell wall and much of the compound is sequestered on β-glucan in the cell wall. Given the limited radius of destruction of singlet oxygen and the density of organic material in the cell wall capable of quenching singlet oxygen, this association may be limiting the depth of cell wall permeation of PPE-DABCO and its capacity to directly perturb the yeast's plasma membrane, relative to EO-OPE-DABCO. The oligomer, on the other hand, appears far less likely to interact with β-glucan, which can allow it to permeate the fungal cell wall more readily and better access the yeast's plasma membrane.

These results shed light onto the mechanisms by which EO-OPE-DABCO effectively kills *C. albicans* yeast cells (FIG. 1A). Having determined that EO-OPE-DABCO was highly effective at killing standard lab-strain *C. albicans* (SC5314), the question remained whether or not its biocidal efficacy would carry over to *C. albicans* clinical isolates.

Using a modified biocidal assay, six *C. albicans* clinical isolates were surveyed for their susceptibility to 10 µg/mL EO-OPE-DABCO in the dark. In this instance, the cells were stained with SYTO 9 and TO-PRO-3 before the introduction of EO-OPE-DABCO. Taking a flow cytometry dual-fluorescent measurement of 10,000 events every minute allowed for real-time reporting of EO-OPE-DABCO-induced membrane perturbation. The susceptibility of clinical isolates was gauged relative to that of *C. albicans* SC5314, as shown in FIGS. 4A-4F. Three of the six isolates, TRL 001 (P-Value=0.006), TRL 051 (P-Value=0.0013), and TRL 057 (P-Value=0.0003) showed significantly increased levels of EO-OPE-DABCO-resistance within 15 minutes' time in the form of slower kinetics of killing and higher residual viability after 15 minutes of treatment. Conversely, no EO-OPE-DABCO-resistance was observed in TRL 037, TRL 040, and TRL 052.

Figure 5:
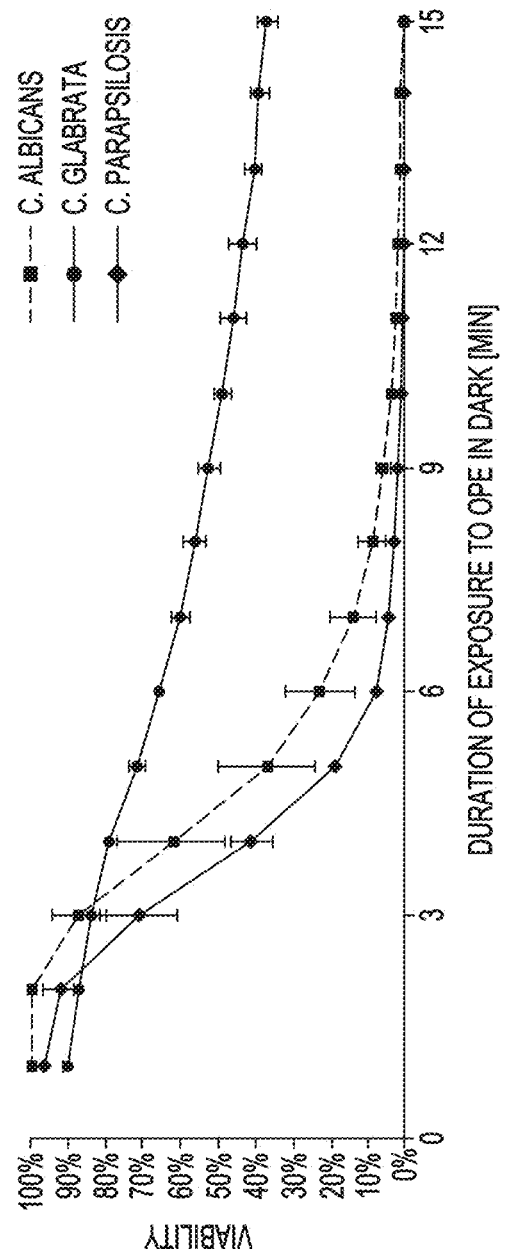
Figure 6A:
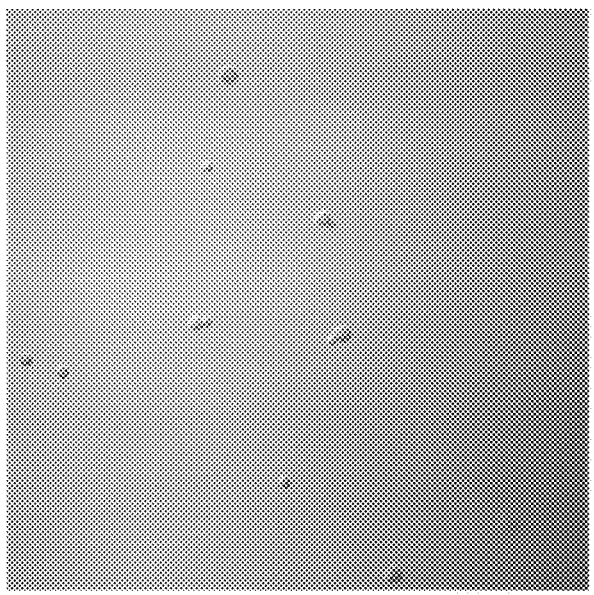
Figure 6B:
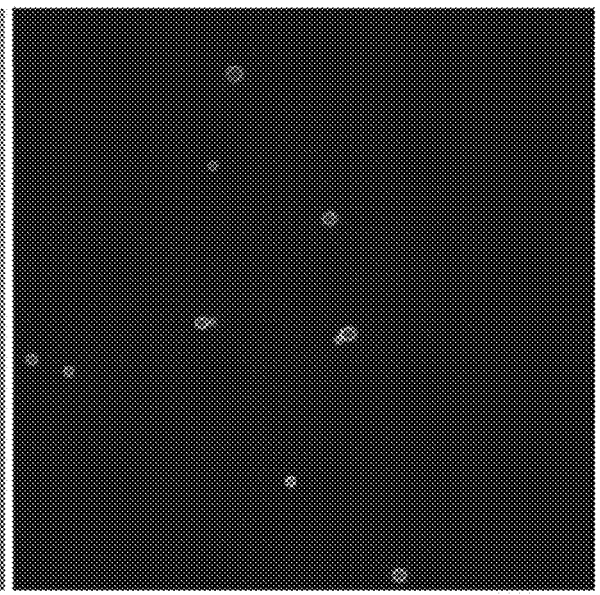

Variability of susceptibility to EO-OPE-DABCO amongst clinical isolates of one species (*C. albicans*) suggested that non-*albicans Candida* species pathogens might also exhibit variable sensitivity to this biocide. The aforementioned 15 min flow cytometry assay was used to determine if EO-OPE-DABCO was more or less effective against *C. parapsilosis* and *C. glabrata* relative to *C. albicans* SC5314. FIG. 5 shows similar degrees of biocidal activity against *C. albicans* and *C. parapsilosis*, but less activity against *C. glabrata*, with about 50% surviving through 15 minutes' exposure. This result is consistent with the fact that *C. albicans* and *C. parapsilosis* share a closer phylogenetic relationship than is found between *C. albicans* and *C. glabrata*.

β-glucan is highly immunogenic upon recognition by the innate immunoreceptors Dectin-1 or Mac-1. Several prominent genera of fungal pathogens, including *Candida*, are known to employ an innate immune evasive strategy of masking glucan to restrict its exposure on the cell wall surface. Without being bound by theory, it is believed that PE antimicrobials bound to cell wall constituents and exposed to light can generate singlet oxygen, leading to local cell wall damage, unmasking β-glucan and increasing immunogenicity. Using an anti-β-(1,3)-glucan primary antibody in tandem with a secondary fluorescently-labeled antibody allowed for the comparison of glucan exposure following treatment conditions: PE in the dark, PE in the light, and a 60 min light negative control. *C. albicans* yeast treated with EO-OPE-DABCO in the dark, using conditions associated with high biocidal activity (FIGS. 1A-1B), exhibited no increase in β-glucan exposure. No glucan unmasking with light-activated EO-OPE-DABCO was observed. *C. albicans* was treated with PPE-DABCO and glucan exposure was observed. PPE-DABCO clearly binds to the fungal cell wall as evidenced by strong PPE-DABCO emission upon 405 nm excitation using confocal imaging (FIGS. 6A and 6B). In the absence of stimulation by light, PPE-DABCO treatment results in no significant increase in glucan exposure. After illumination, PPE-DABCO treated cell walls do show evidence of significant glucan unmasking (FIG. 7). In FIG. 7, β-glucan exposure estimated from median fluorescence signal of AF 647. The exposure duration of all samples in FIG. 7 was 60 min, with the exception of OPE-DABCO exposure in the light, for which the exposure duration was limited to 10 min. PPE-DABCO-induced glucan unmasking is evident under illumination conditions that are not biocidal for *C. albicans*. These results suggested that glucan masking in *Candida* cell walls are sensitive to cationic stress, and, to a far greater degree, $^1O_2$ and other ROS.

Given that PPE-DABCO can increase β-glucan exposure on *C. albicans* yeast, a test of whether the unmasking achieved by this treatment resulted in greater recognition of yeasts through the β-glucan receptor Dectin-1 was conducted. HEK-293 cells were transfected with mApple-tagged human Dectin-1a. Dectin-1 expression is sufficient to drive phagocytosis of *C. albicans* yeast cells by transfectants. The transfection conditions resulted in Dectin-1$^+$ HEK-293, discriminated by positive mApple signal, and non-transfected cells, which were negative for mApple and served as an internal control to assess Dectin-1 dependence of binding and phagocytosis. A flow cytometric assay of yeast cell binding to and internalization by HEK-293 transfectants was used. Yeasts were labeled with the pH-sensitive dye CypHer 5, which increases dramatically in emission intensity after internalization within acidic phagosomal compartments. The Cypher 5 signal was used to measure binding and internalization of yeast. Flow cytometry data were gated on HEK-293 cell-containing events for analysis, as defined by high side scatter signal, which was significantly larger than free yeast. Yeast bound to HEK-293 cells registered a low Cypher 5 signal. If yeasts were internalized, the CypHer 5 signal was much higher. The percent of HEK-293 cells with yeast bound (for mApple-Dectin-1$^+$ and mApple-Dectin-1$^-$ cells) was determined by the percent of SSC-gated events having low or high CypHer 5 signal. The extent of phagocytosis was assessed by the median CypHer 5 fluorescence intensity within these populations.

Figure 8A:
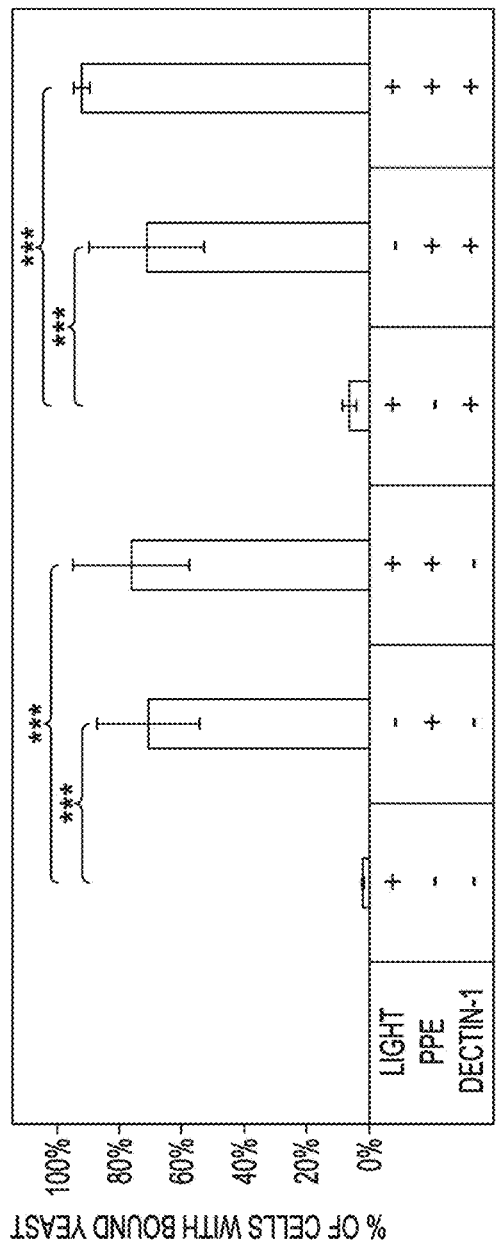
Figure 8B:
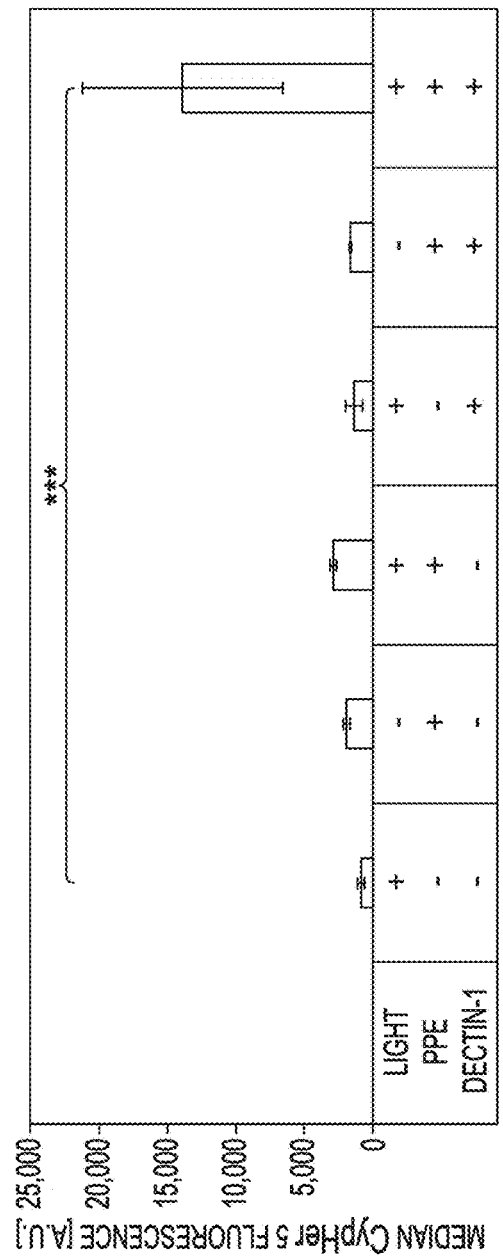

For the results shown in FIGS. 8A-8B, prior to the addition of HEK cells, samples were first treated with 10 µg/mL PPE-DABCO for 1 h and subsequently stained with CypHer 5 and SYTO 9. As can be seen in FIGS. 8A-8B, minimal binding between mApple-Dectin-1a$^-$ HEK-293 cells and untreated. *C. albicans* yeast cells was observed, Even if the HEK-293 cell has been transfected and is expressing Dectin-1 (mApple+), glucan masking permits very little β-glucan to be accessible at the cell wall surface for Dectin-1 binding (as seen in FIG. 7). Conversely, PPE-treated *C. albicans* yeast cells bind avidly to HEK-293 cells, and this binding is independent of excitation of PPE-DABCO or Dectin-1 expression by the HEK-293. These data suggest, without being bound by theory, that the binding of PPE-DABCO to *Candida* cell walls alters their surface properties in ways that promote Dectin-1 independent adhesion to human cells, perhaps through electrostatic and/or hydrophobic mechanisms. The extent of interaction between the yeast cell and the HEK-293 cell is not dependent on the degree of incurred cell membrane damage, as *C.*

*albicans* killed with light-activated PPE-DABCO were no more likely to bind HEK-293 cells. Despite their ability to bind HEK-293 cells, internalization of PPE-DABCO treated *C. albicans* yeasts required Dectin-1 expression and excitation of PPE-DABCO prior to binding. These data indicate that the glucan unmasking caused by light-activation of PPE-DABCO on *C. albicans* cell walls can result in the biological outcome of increased Dectin-1 dependent phagocytosis.

Despite their intrinsic resistance to cationic and oxidative stresses, *C. albicans* was highly susceptible to EO-OPE-DABCO, and to a lesser extent, PPE-DABCO. Biocidal activity of these compounds against *C. albicans* utilizes a dual mechanism combining light-independent cationic stress and light-dependent oxidative stress. Unlike other broad-spectrum antimicrobials, PEs exhibit low levels of in vitro toxicity against mammalian cells, making them intriguing candidates in numerous clinical applications.

Therefore, it is relevant to note that all clinical isolate strains exhibited significant amounts of killing during a 15 min exposure to EO-OPE-DABCO. Partial resistance of some clinical isolate strains may derive from adaptations of the pathogen to growth in the host, which may cause changes in cell wall structure and upregulation of mechanisms that permit growth under adverse conditions, such as leukocyte-derived ROS in the phagosomal environment.

While *C. parapsilosis* was found to be just as susceptible to EO-OPE-DABCO in the dark as *C. albicans*, *C. glabrata* displayed an inherent resistance. *Candida* spp. experience cationic stress as they interact with innate immune defenses. For example, cationic antimicrobial peptides, such as Histatnin-5, are deployed in host defense against *Candida* spp. and are thought to work by disrupting fungal plasma membrane integrity (REF). *C. glabrata* is noted for its resistance to killing by cationic antimicrobial peptides relative to *C. albicans* and other *Candida* spp. pathogens. Furthermore, *C. albicans* yeast cells display a modest stress response in the presence of heavy metal cations, activating 48 genes as a coping mechanism. Conversely, the cationic stress response in *C. glabrata* is more extensive, with over 100 genes being activated under similar circumstances. Cationic stresses imparted by heavy metals differs slightly from that of PEs; however, both are able to denature native protein conformation, and therefore may activate similar genes as part of a cationic stress response among *Candida* yeast cells. EO-OPE-DABCO's decreased ability to kill *C. glabrata* resembles the results of a previous study, in which a 10 μg/mL concentration of the compound failed to kill 99% of *S. cerevisiae* yeast, even after an hour in the light. Although *S. cerevisiae* is benign, it is closely related to *C. glabrata*. *C. glabrata* is also known to have robust antioxidative defenses that allow it to survive in the phagosome, and may impact its ability to resist oxidative killing by cationic phenylene ethynylenes.

It was found that PPE-DABCO strongly associates with soluble β-(1,3)-glucan (FIGS. 3A-3D), which is important for structural support of the cell wall of *C. albicans*. The PPE-DABCO/glucan interaction can, without being bound by theory, directly cause more global disruption to the cell wall, and it is likely that the targeting of polymeric phenylene ethynylenes to cell wall polysaccharides places them in an ideal position reactive oxygen-mediated damage to cell wall components after photoactivation. EO-OPE-DABCO appears far less prone to complexation with the soluble β-(1,3)-glucan. Although this limits the EO-OPE-DABCO's ability to unmask mannoproteins and reveal more β-(1,3)-glucan (FIG. 7), the lack of interaction with the glucan likely allows the molecule to quickly penetrate the cell wall, access and damage the cell membrane.

Furthermore, PPE-DABCO displays immunostimulatory attributes, particularly in the light. This polymer was found to unmask the mannoprotein layer of *C. albicans* yeast cells in such a way that β-(1,3)-glucan could more easily be recognized and bound by pattern recognition receptor Dectin-1. PPE-DABCO binds to yeast cell walls (FIGS. 6A-6B). The chemical basis of this binding can relate to direct interactions between PPE-DABCO and β(1,3)-glucan, as discussed herein. Additionally, PPE-DABCO may interact electrostatically with anionic moieties in the outer cell wall. Ultrastructural studies have described the presence of evenly-dispersed anionic sites on the *C. albicans* yeast surface. Also, *C. albicans* N-linked mannans contain abundant oligomannose side chains attached via anionic phosphodiester linkages that could provide sites of electrostatic binding for polycations like PPE-DABCO. In either configuration, PPE-DABCO would be ideally positioned in the outer cell wall to damage mannoproteins that are thought to provide glucan masking. The results described herein suggest that merely the binding of PPE-DABCO to *C. albicans* increases adherence of yeast to HEK-293 cells in a receptor-independent fashion, suggesting that PPE-DABCO alters cell wall surface characteristics in ways that impact interaction with host cells non-specifically (FIG. 8A). However, increases in both glucan exposure and Dectin-1-dependent phagocytosis require excitation of PPE-DABCO, which probably results in direct oxidative damage to the cell wall leading to glucan unmasking. This is the first instance in which PEs have been demonstrated to elicit immunostimulatory attributes. The method described herein demonstrates that the biocidal and immunostimulatory properties of phenylene ethynylene antimicrobials make them promising candidates for novel antimicrobial applications to improve the health outcomes of patients with life-threatening fungal infectious diseases.

Figure 9A:
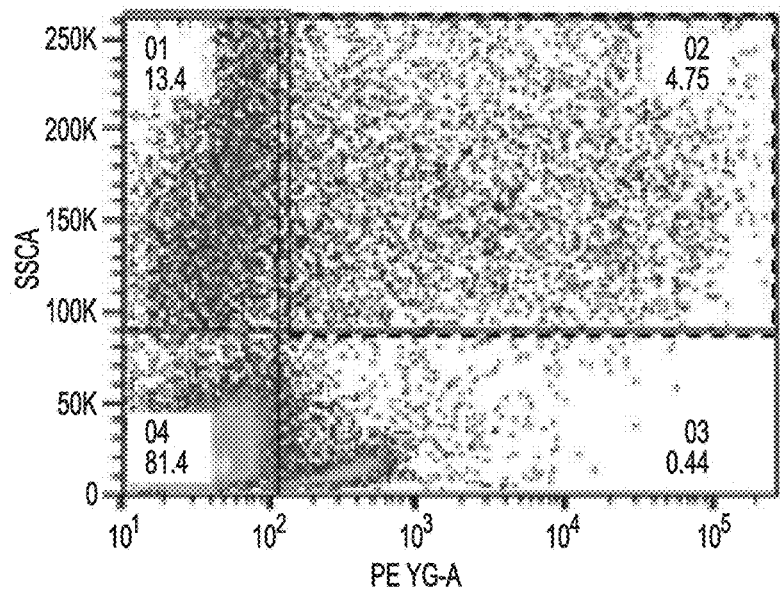
FIG. 9D is a plot of the yeast cell interaction with HEK 293 cells in the light and with heat-treated yeast (positive control).
FIG. 9E is a plot of the upper left quadrant from FIG. 9D.
FIG. 9F is a plot of the upper right quadrant from FIG. 9D.
FIG. 9G is a plot of the yeast cell interaction with HEK 293 cells in the dark in the presence of PPE-DABCO.
FIG. 9H is a plot of the upper left quadrant from FIG. 9G.
FIG. 9I is a plot of the upper right quadrant from FIG. 9G.
FIG. 9J is a plot of the yeast cell interaction with HEK 293 cells in the light in the presence of PPE-DABCO.
FIG. 9K is a plot of the upper left quadrant from FIG. 9J.
FIG. 9L is a plot of the upper right quadrant from FIG. 9J.
Figure 9B:
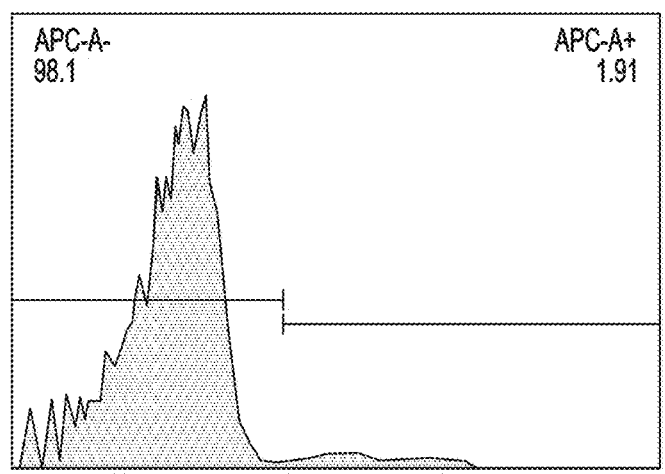
Figure 9C:
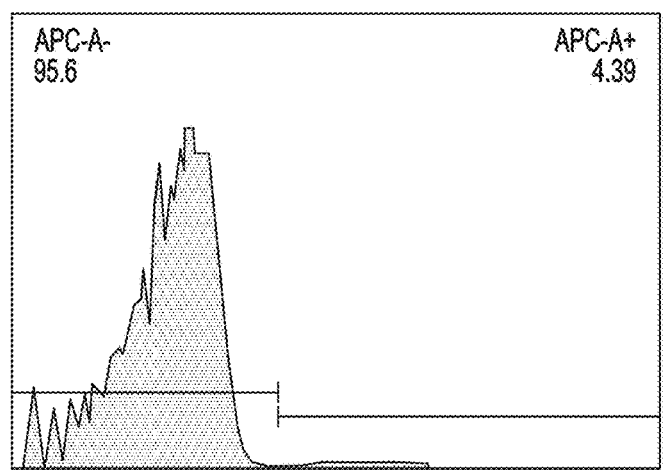
Figure 9D:
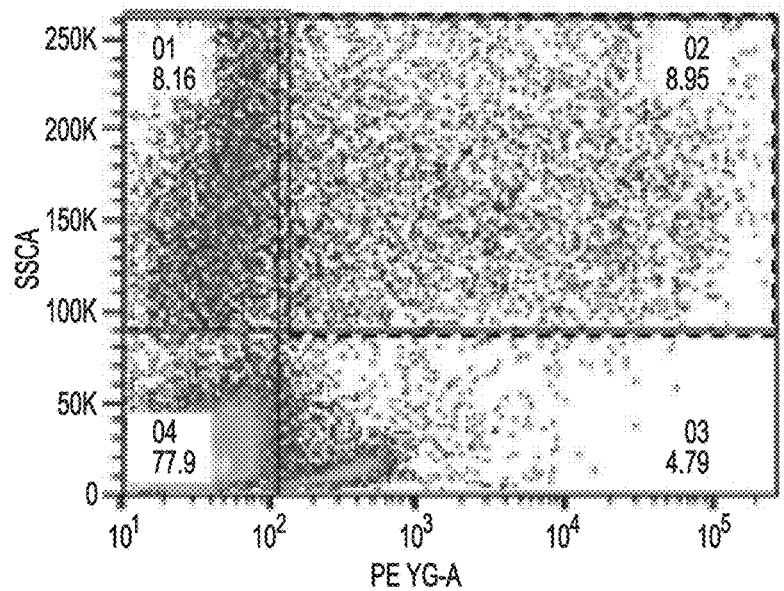
Figure 9E:
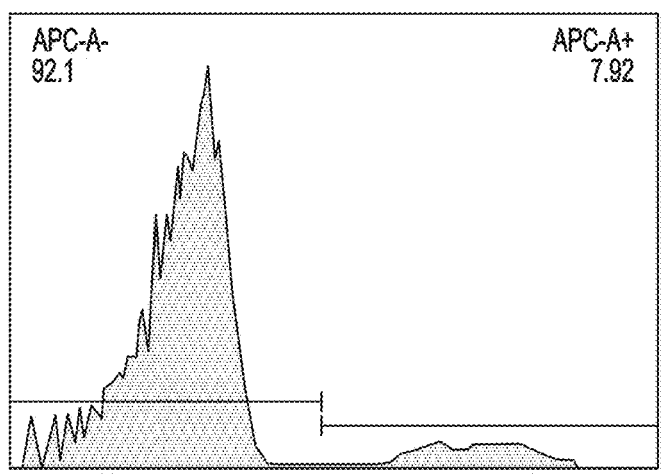
Figure 9F:
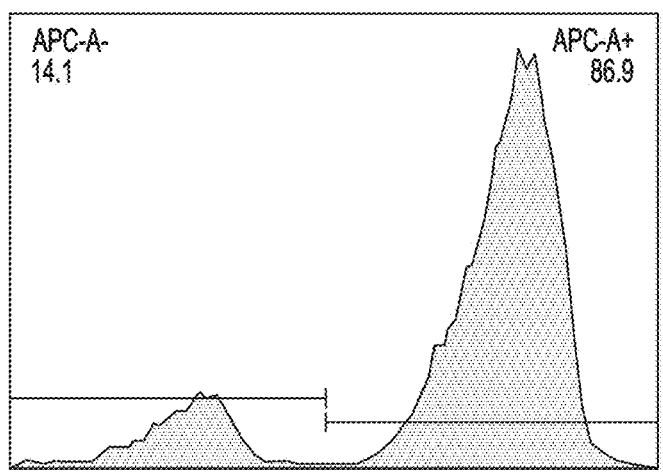
Figure 9G:
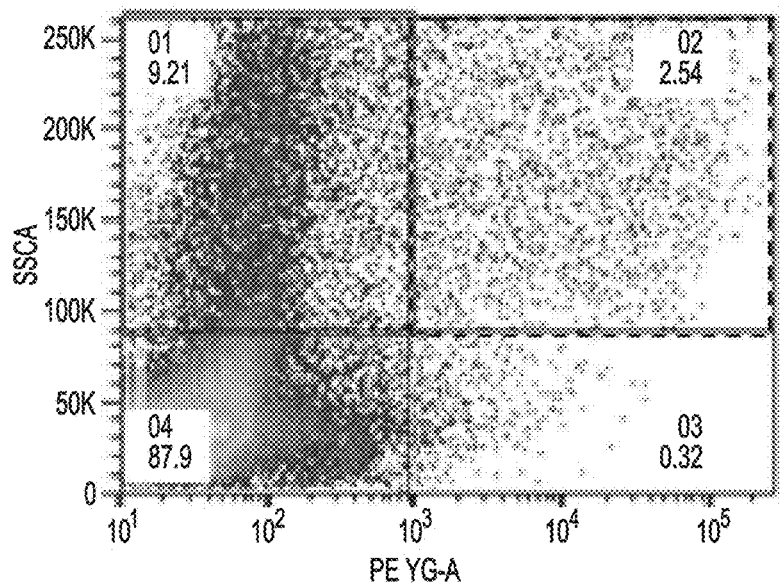
Figure 9H:
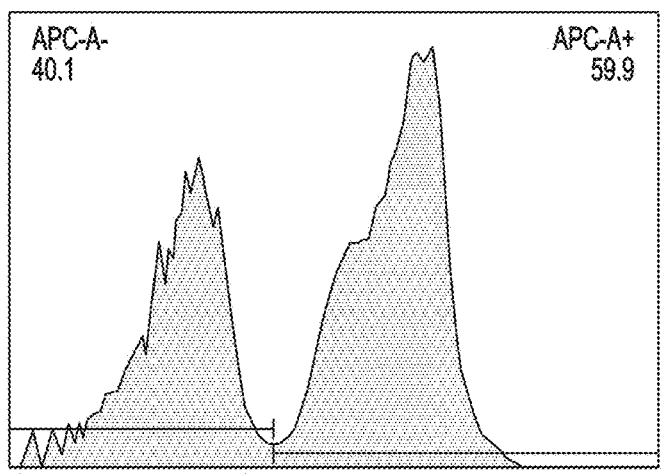
Figure 9I:
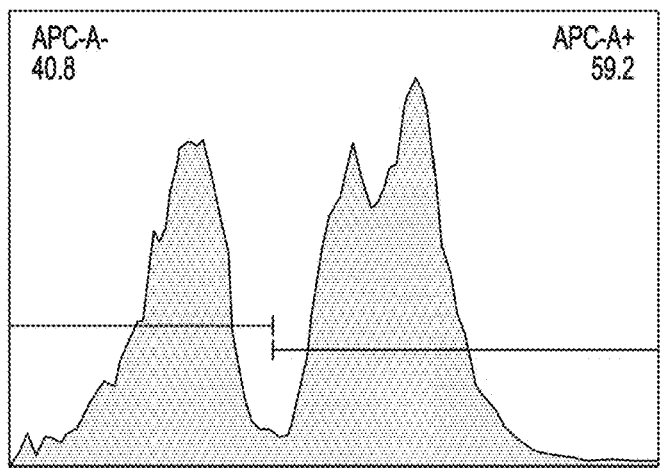
Figure 9J:
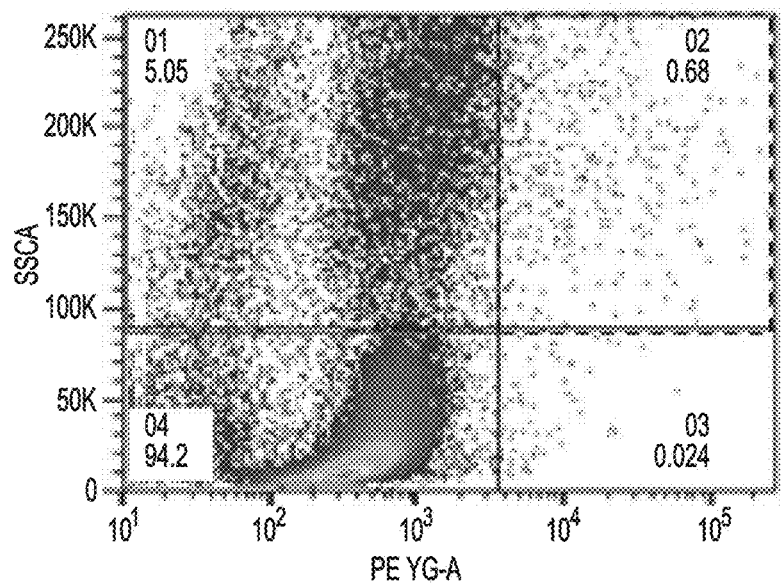
Figure 9K:
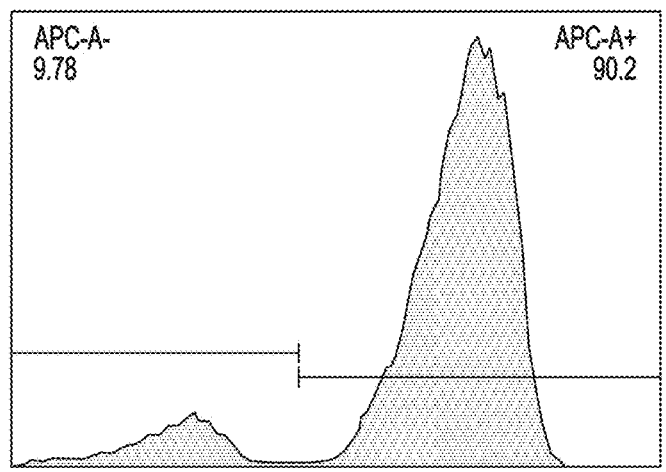
Figure 9L:
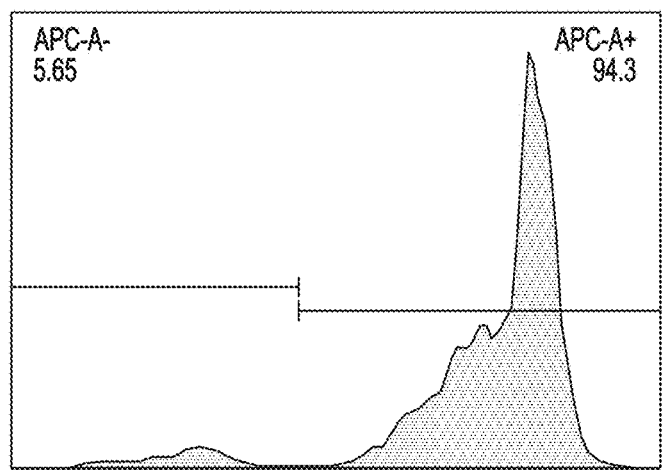
Figure 10A:
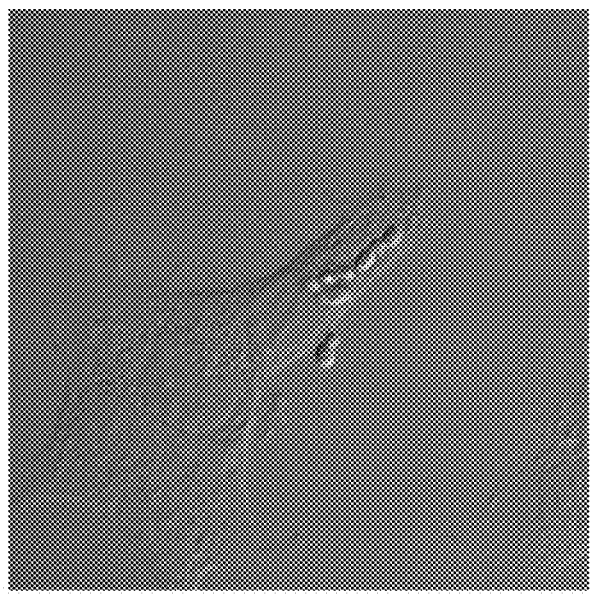
FIGS. 10A and 10B are confocal microscopy image illustrating various *C. albicans* yeast cells associating with HEK 293 cells.
Figure 10B:
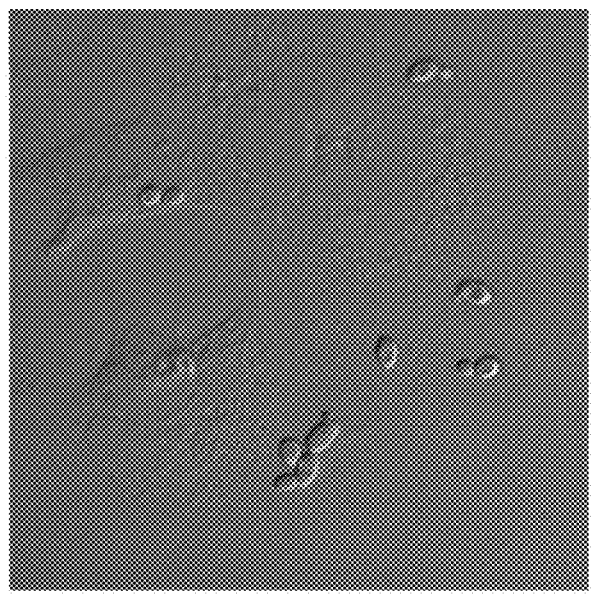

FIGS. 9A-9L show interactions between *C. albicans* yeast cells and PPE-DABCO, as well as both positive and negative control experiments. The upper left quadrant in FIGS. 9A, 9D, 9G, and 9J encompass events that are SSC+ and mApple−, and represent all Hek 293 cells that were not successfully transfected, and therefore do not express Dectin-1. The upper right quadrants in FIGS. 9A, 9D, 9G, and 9J encompass events that are SSC+ and mApple+, and represent all Hek 293 cells that were successfully transfected, and therefore do express Dectin-1. Of all events falling under the red or green gates, those that are CypHer 5− are assumed to be non-transfected Hek cells that are not interacting with a *C. albicans* yeast cell; those that are CypHer 5+ are interacting with at least one *C. albicans* yeast cell. In FIGS. 9A-9C, no compound was used and 420 nm light (6.62+/−2.93 mW/cm$^2$) was as a negative control to show that light itself is not responsible for the activity observed in FIGS. 9D-9L. In FIGS. 9D-9F, heat treatment serves to kill the yeast but also causes changes in the cell wall of the yeast, and increases binding and internalization of the yeast into the Dectin-1 transfected cells. The heat treated cells are therefore considered a positive control that shows that binding and internalization occur. The heat treatment involved heating the sample to 70° C. for 30 minutes to kill the yeast and to increase β-glucan exposure of *C. albicans*.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

ADDITIONAL EMBODIMENTS

The following exemplary embodiments are provided, the numbering of which is not to be construed as designating levels of importance:

Embodiment 1 provides a method of treating a fungal infection, the method comprising: contacting a fungus comprising a β-glucan that is at least partially masked from immune system detection with a therapeutically effective amount of a compound that at least partially unmasks the β-glucan to increase immunogenicity of the fungus.

Embodiment 2 provides the method of Embodiment 1, wherein the β-glucan comprises β-(1,3;1,6)-glucan.

Embodiment 3 provides the method of any one of Embodiments 1-2, wherein the fungus is a *Candida* species fungus, an *Aspergillus* species fungus, or a *Histoplasma* species fungus.

Embodiment 4 provides the method of any one of Embodiments 1-3, wherein the fungus is *Candida albicans, Candida glabrata, Candida parapsilosis*, or a combination thereof.

Embodiment 5 provides the method of any one of Embodiments 1-4, wherein the fungus comprises a biofilm.

Embodiment 6 provides the method of any one of Embodiments 1-5, wherein the fungus is in or on an indwelling medical device.

Embodiment 7 provides the method of any one of Embodiments 1-6, wherein the fungus is in or on a catheter.

Embodiment 8 provides the method of any one of Embodiments 1-7, wherein the compound is a polycationic conjugated aromatic system.

Embodiment 9 provides the method of any one of Embodiments 1-8, wherein the compound comprises a unit having the structure:

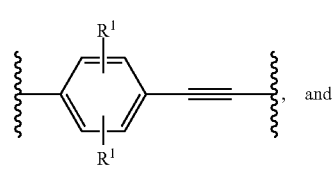

wherein
$A^1$ is chosen from a bond,

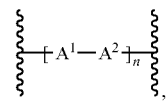

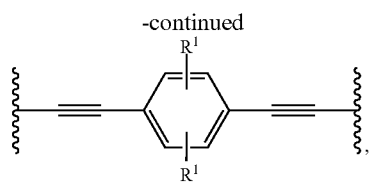

$A^2$ is chosen from a bond,

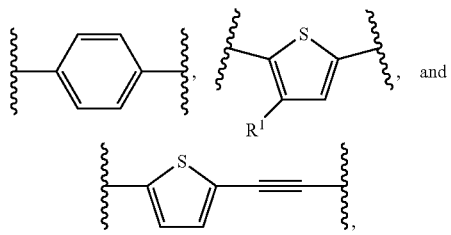

$R^1$ is chosen from —H and $C^1$, wherein the compound comprises at least one $C^1$, at each occurrence, $C^1$ is independently chosen from -L-D and —O-L-D, at each occurrence, L is independently $(C_1-C_{10})$hydrocarbylene, at each occurrence, D is independently chosen from —N$((C_1-C_5)$alkyl$)_3$ and a $(C_1-C_{10})$alkyl-substituted cationic nitrogen-containing $(C_1-C_5)$heterocycle, and n is about 1 to about 100,000.

Embodiment 10 provides the method of Embodiment 9, wherein the compound has the structure:

$$T-R^2-(A^1-A^2)_n-R^3-T,$$

wherein
$R^2$ is chosen from a bond and

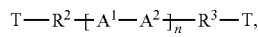

$R^3$ is chosen from a bond and

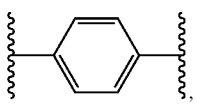

and
at each occurrence, T is independently chosen from —H, C(O)—O—$(C_1-C_{10})$alkyl, -phenyl, and —$R^1$.

Embodiment 11 provides the method of any one of Embodiments 9-10, wherein at each occurrence, L is independently chosen from methylene, ethylene, propylene, butylene, pentylene, and heptylene.

Embodiment 12 provides the method of any one of Embodiments 9-11, wherein the variable $A^1$ is chosen from a bond,

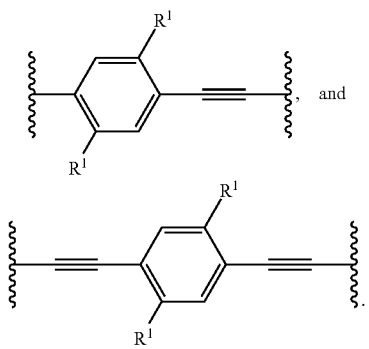, and

Embodiment 13 provides the method of any one of Embodiments 9-12, wherein at each occurrence, D is independently chosen from —N(CH$_3$)$_3$,

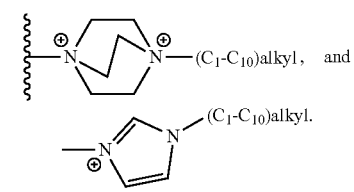

Embodiment 14 provides the method of any one of Embodiments 9-13, wherein at each occurrence, D is independently chosen from —N(CH$_3$)$_3$,

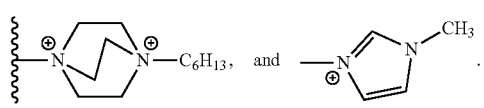

Embodiment 15 provides the method of any one of Embodiments 9-14, wherein C$^1$ is chosen from:

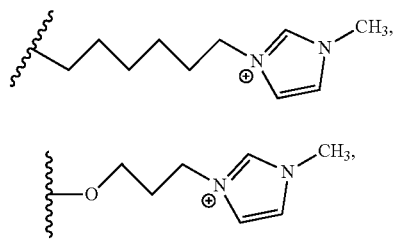

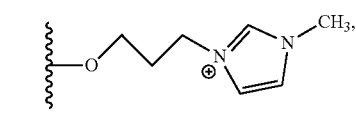

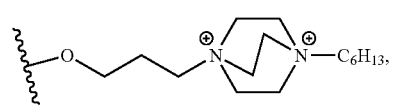

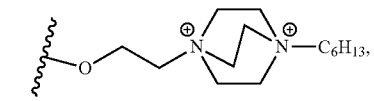

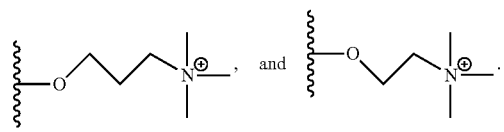

Embodiment 16 provides the method of any one of Embodiments 9-15, wherein at each occurrence, T is independently chosen from —H, C(O)—O-ethyl, -phenyl, and —R$^1$.

Embodiment 17 provides the method of any one of Embodiments 1-16, wherein the compound is:

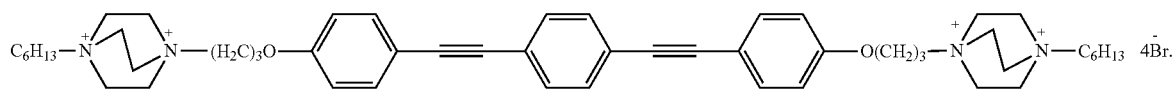

Embodiment 18 provides the method of any one of Embodiments 1-17, wherein the compound is a polymer comprising the repeating unit:

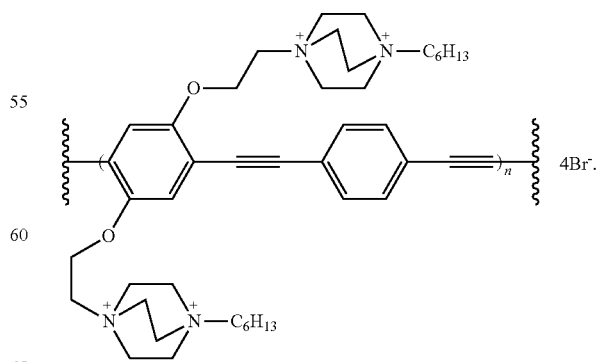

Embodiment 19 provides the method of Embodiment 18, wherein the polymer is a homopolymer.

Embodiment 20 provides the method of any one of Embodiments 1-19, wherein the compound is a polymer comprising the repeating unit:

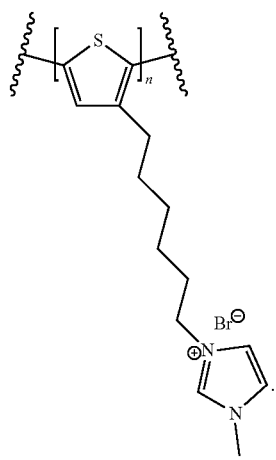

Embodiment 21 provides the method of Embodiment 20, wherein the polymer is a homopolymer.

Embodiment 22 provides the method of any one of Embodiments 1-21, wherein the compound is a polymer comprising the repeating group:

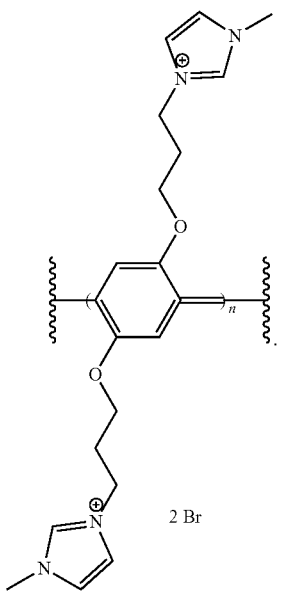

Embodiment 23 provides the method of Embodiment 22, wherein the polymer is a homopolymer.

Embodiment 24 provides the method of any one of Embodiments 1-23, wherein compound is a polymer comprising the repeating group:

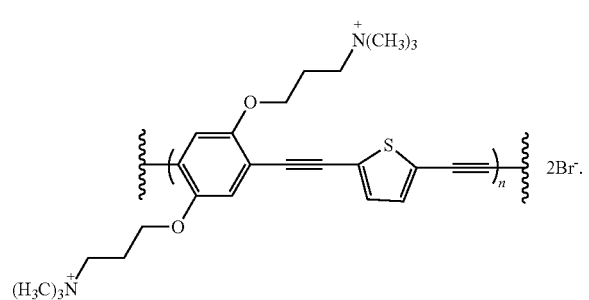

Embodiment 25 provides the method of Embodiment 24, wherein the polymer is a homopolymer.

Embodiment 26 provides the method of any one of Embodiments 1-25, wherein the compound is:

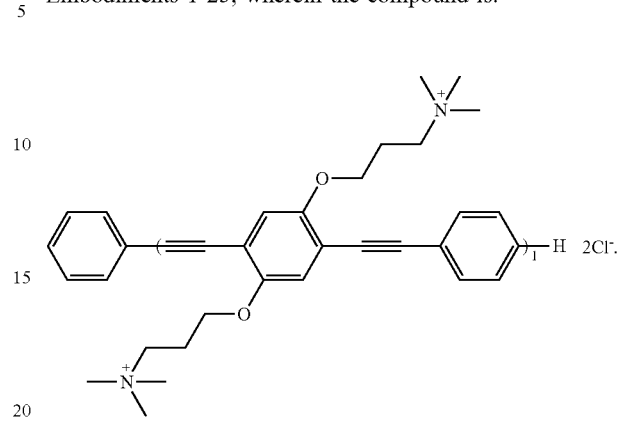

Embodiment 27 provides the method of any one of Embodiments 1-26, wherein the compound is:

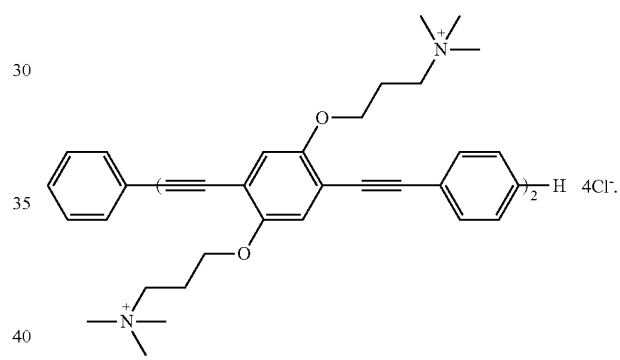

Embodiment 28 provides the method of any one of Embodiments 1-27, wherein the compound is:

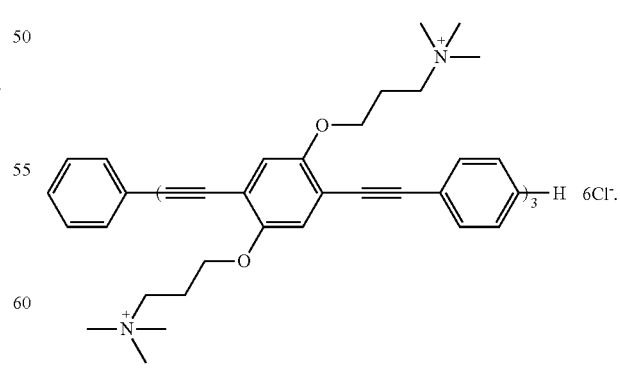

Embodiment 29 provides the method of any one of Embodiments 1-28, wherein the compound is:

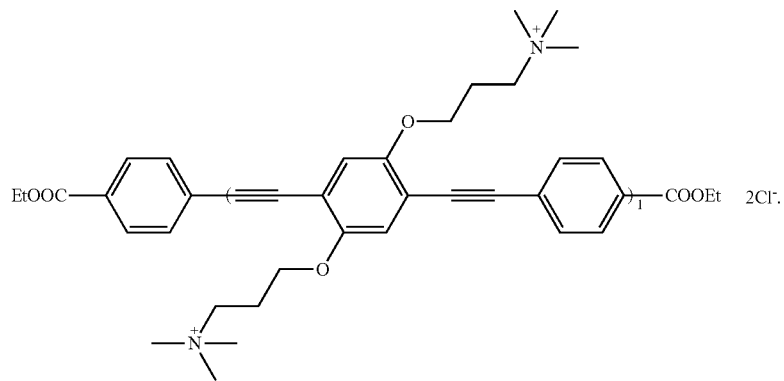
Embodiment 30 provides the method of any one of Embodiments 1-29, wherein the compound is:
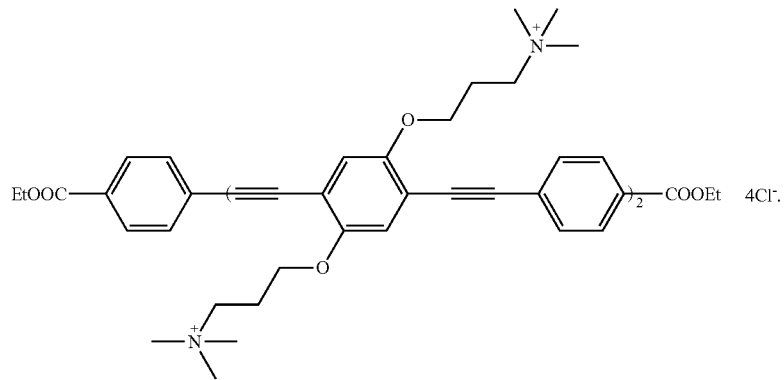
Embodiment 31 provides the method of any one of Embodiments 1-30, wherein the compound is:
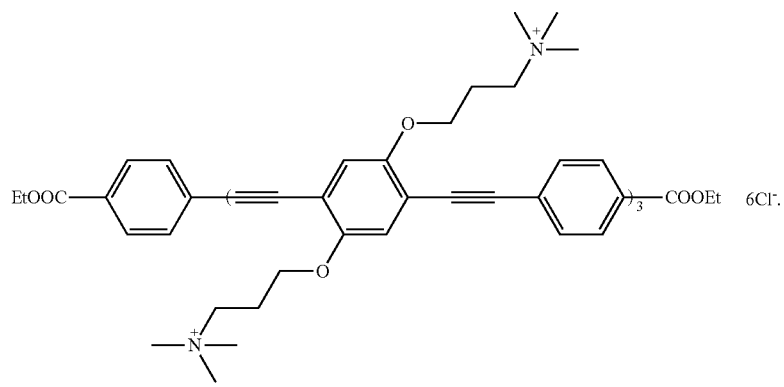
Embodiment 32 provides the method of any one of Embodiments 1-31, wherein the compound is:
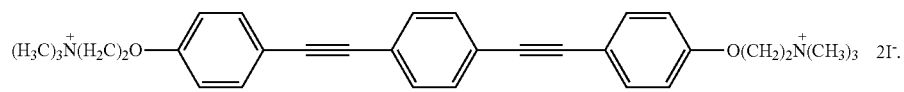

Embodiment 33 provides the method of any one of Embodiments 1-32, wherein the compound is:

$(H_3C)_3\overset{+}{N}(H_2C)_2O$—[phenyl]—≡—[phenyl]—≡—[phenyl]—$O(CH_2)_2\overset{+}{N}(CH_3)_3$  2I⁻.

Embodiment 34 provides e method of any one of Embodiments 1-33, wherein the compound is:

$(H_3C)_3\overset{+}{N}(H_2C)_2O$—[phenyl]—≡—[thiophene-S]—≡—[phenyl]—$O(CH_2)_2\overset{+}{N}(CH_3)_3$  2I⁻.

Embodiment 35 provides the method of any one of Embodiments 1-34, wherein the compound is:

$(H_3C)_3\overset{+}{N}(H_2C)_2O$—[phenyl]—≡—[thiophene-S]—≡—[phenyl]—$O(CH_2)_2\overset{+}{N}(CH_3)_3$  2I⁻.

Embodiment 36 provides a method of treating a fungal infection, the method comprising:

contacting a fungus comprising a β-glucan that is at least partially masked from immune system surveillance with a therapeutically effective amount of a compound that at least partially unmasks the β-glucan to increase immunogenicity of the fungus, wherein the compound comprises a unit having the structure:

$$\{-[A^1-A^2]_n-\},$$

wherein $A^1$ is chosen from a bond,

[phenyl with R¹ substituents and alkyne],

[alkyne-phenyl(R¹)-alkyne],

[phenyl], [thiophene with R¹], and

-continued

[thiophene-alkyne], $R^1$ is chosen from —H and $C^1$, wherein the compound comprises at least one $C^1$, at each occurrence, $C^1$ is independently chosen from -L-D and —O-L-D, at each occurrence, L is independently $(C_1-C_{10})$hydrocarbylene, at each occurrence, D is independently chosen from —N$((C_1-C_5)$alkyl$)_3$ and a $(C_1-C_{10})$alkyl-substituted cationic nitrogen-containing $(C_1-C_5)$heterocycle, and n is about 1 to about 100,000.

Embodiment 37 provides a method of preventing or reducing a fungal infection on a substrate, the method comprising:

treating the substrate with a therapeutically effective amount of a compound so that contact between the treated surface and a fungus comprising β-glucan that is at least partially masked from immune system detection is effective to at least partially unmask the (β-glucan thereby increasing immunogenicity of the fungus and preventing or reducing fungal infection on the substrate from the fungus.

Embodiment 38 provides a method of preventing or reducing a fungal infection on or in a device, the method comprising:

treating the device with a therapeutically effective amount of a compound so that contact between the compound and a fungus comprising β-glucan that is at least partially masked from immune system detection is effective to at least partially unmask the β-glucan thereby increasing immunogenicity of the fungus and preventing or reducing fungal infection on or in the device from the fungus.

Embodiment 39 provides an antifungal compound comprising a unit having the structure:

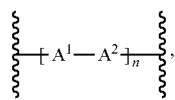

wherein

A[1] is chosen from a bond,

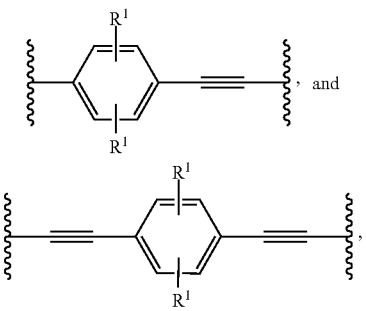

A[2] is chosen from a bond.

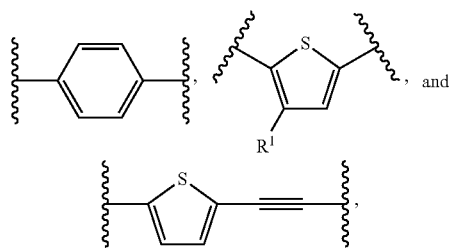

R[1] is chosen from —H and C[1], wherein the compound comprises at least one C[1], at each occurrence, C[1] is independently chosen from -L-D and —O-L-D, at each occurrence, L is independently $(C_1-C_{10})$hydrocarbylene, at each occurrence, D is independently chosen from —N(($C_1-C_5$)alkyl)$_3$ and a ($C_1-C_{10}$)alkyl-substituted cationic nitrogen-containing ($C_1-C_5$)heterocycle, and n is about 1 to about 100,000, wherein contact between a therapeutically effective amount of the compound and a fungus comprising β-glucan that is at least partially masked from immune system detection is effective to at least partially unmask the β-glucan thereby increasing immunogenicity of the fungus.

Embodiment 40 provides the method of Embodiment 39, wherein the compound has the structure:

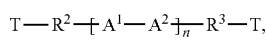

wherein

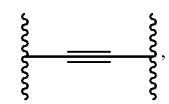

R[2] is chosen from a bond and

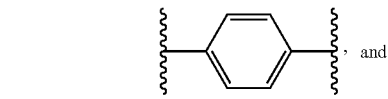

R[3] is chosen from a bond and at each occurrence, T is independently chosen from —H, C(O)—O—($C_1-C_{10}$)alkyl, -phenyl, and —R[1].

Embodiment 41 provides the method or compound of any one or any combination of Embodiments 1-40 optionally configured such that all elements or options recited are available to use or select from.

What is claimed is:

1. A method of treating a fungal infection, the method comprising:

contacting a fungus with an amount of a compound and exposing the contacted fungus to light, wherein the amount of the compound and the light are therapeutically effective to increase immunogenicity of the fungus, wherein the fungus is a *Candida* species fungus, an *Aspergillus* species fungus, or a *Histoplasma* species fungus, wherein the *Candida* species fungus is *Candida glabrata, Candida parapsilosis*, or a combination thereof, and the compound is a polycationic conjugated system comprising a repeating unit having the structure:

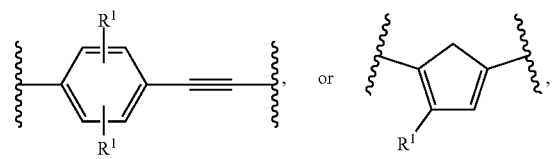

wherein

R[1] is independently chosen from —H and C[1], wherein the repeating unit comprises at least one C[1], at each occurrence, C[1] is independently chosen from -L-D and —O-L-D, at each occurrence, L is independently $(C_1-C_{10})$hydrocarbylene, and at each occurrence, D is independently chosen from —N(($C_1-C_5$)alkyl)$_3$ and a ($C_1-C_{10}$)alkyl-substituted cationic nitrogen-containing ($C_1-C_5$)heterocycle.

2. The method of claim 1, wherein the fungus comprises a β-glucan.

3. The method of claim 2, wherein the fungus comprises a β-(1,3;1,6)-glucan.

4. The method of claim 1, wherein the fungus is *Candida glabrata, Candida parapsilosis*, or a combination thereof.

5. The method of claim 1, wherein the fungus is in or on an indwelling medical device.

6. The method of claim 1, wherein the fungus is in or on a catheter.

7. The method of claim 1, wherein the compound comprises a unit having the structure:

wherein

A¹ is chosen from a bond,

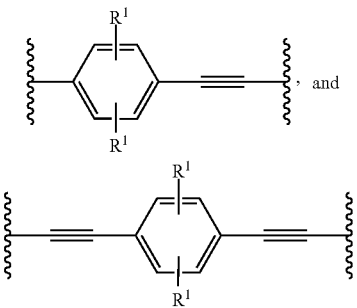, and

A² is chosen from a bond,

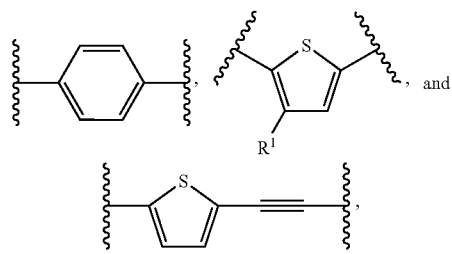, and at least one of A¹ and A² is other than a bond,

R¹ is chosen from —H and C¹, wherein the compound comprises at least one C¹, at each occurrence, C¹ is independently chosen from -L-D and —O-L-D, at each occurrence, L is independently $(C_1\text{-}C_{10})$hydrocarbylene, at each occurrence, D is independently chosen from —N$((C_1\text{-}C_5)$alkyl$)_3$ and a $(C_1\text{-}C_{10})$alkyl-substituted cationic nitrogen-containing $(C_1\text{-}C_5)$heterocycle, and n is about 1 to about 100,000.

8. The method of claim 7, wherein the compound has the structure:

$$T-R^2+A^1-A^2+_n R^3-T,$$

wherein

R² is chosen from a bond and

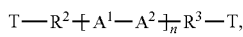,

R³ is chosen from a bond and

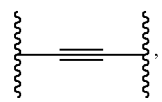, and at each occurrence, T is independently chosen from —H, C(O)—O—$(C_1\text{-}C_{10})$, -phenyl, and —R¹.

9. The method of claim 1, wherein at each occurrence, L is independently chosen from methylene, ethylene, propylene, butylene, pentylene, and heptylene.

10. The method of claim 7, wherein the variable A¹ is chosen from

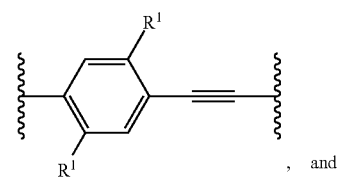, and

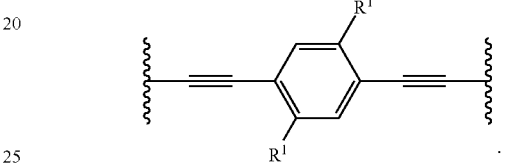

11. The method of claim 1, wherein at each occurrence, D is independently chosen from —N(CH₃)₃,

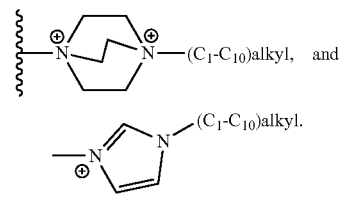

12. The method of claim 1, wherein C¹ is chosen from:

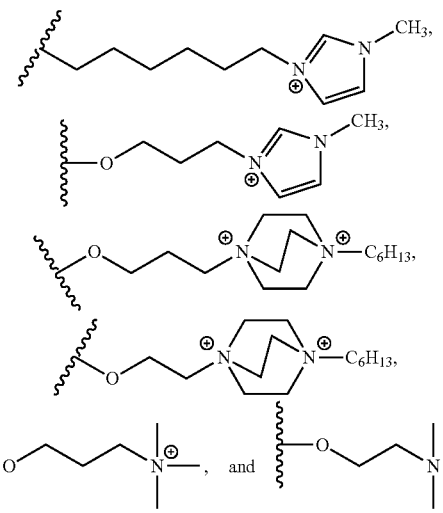

13. The method of claim 8, wherein at each occurrence, T is independently chosen from —H, —C(O)—O-ethyl, -phenyl, and —R¹.

14. The method of claim 1, wherein the compound is:
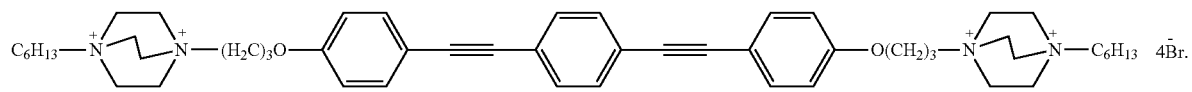
15. The method of claim 1, wherein the compound is a polymer comprising a repeating unit chosen from:
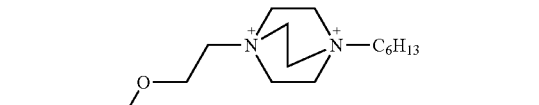
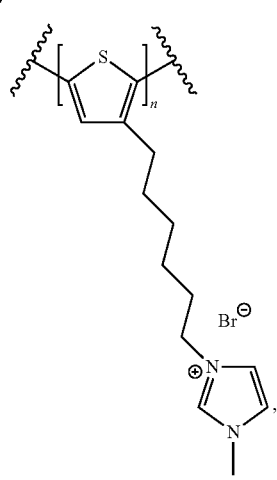
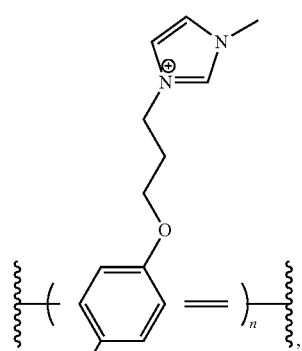
-continued
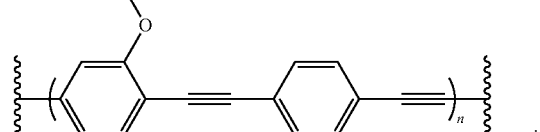
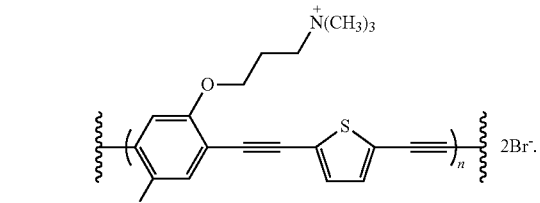
16. The method of claim 1, wherein the compound is chosen from:

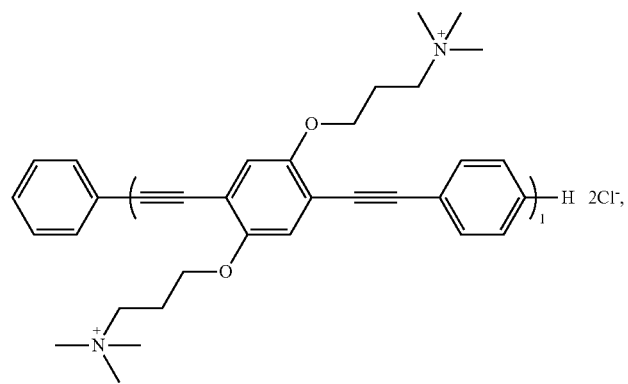
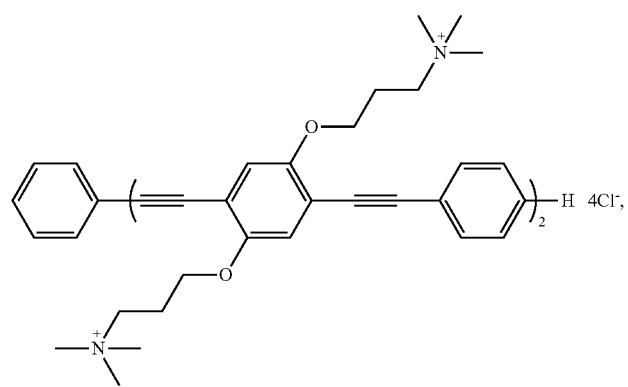
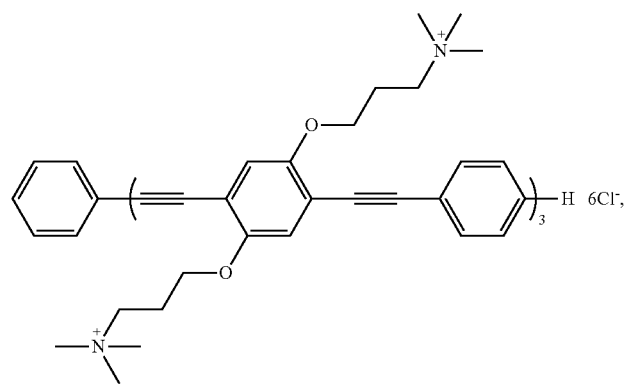
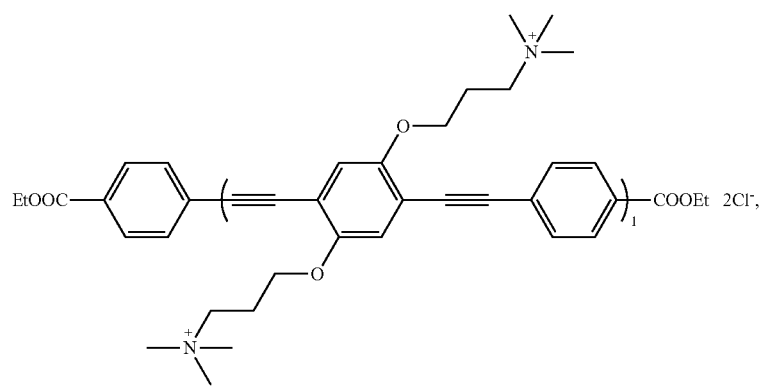

-continued
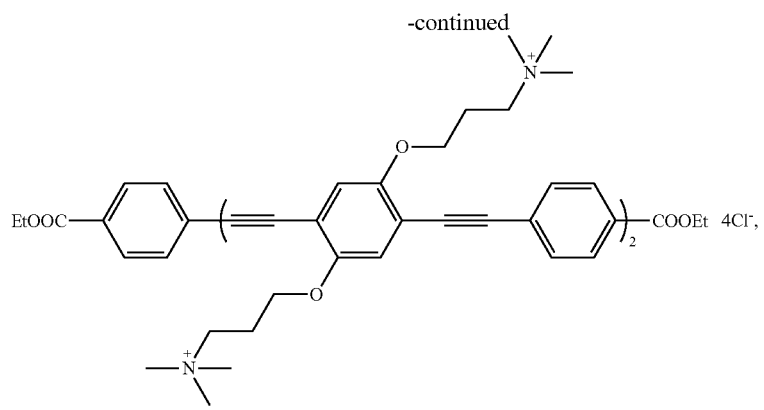
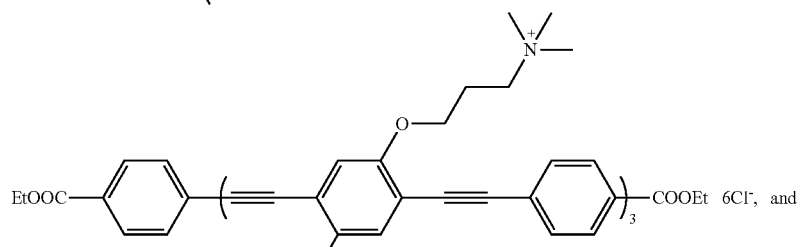
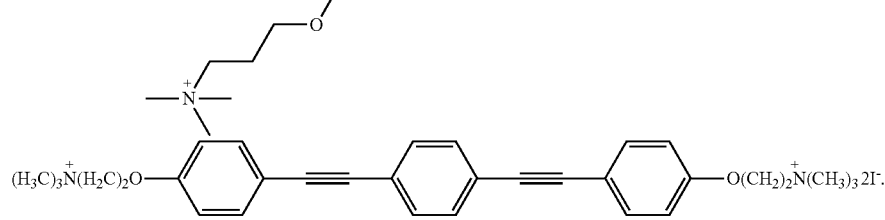
17. The method of claim 1, wherein the fungus is *Candida parapsilosis*.
18. The method of claim 1, wherein the fungus is an *Aspergillus* species fungus or a *Histoplasma* species fungus.
* * * * *